US011732043B2

(12) United States Patent
Geuijen et al.

(10) Patent No.: US 11,732,043 B2
(45) Date of Patent: Aug. 22, 2023

(54) ANTIBODIES THAT MODULATE A BIOLOGICAL ACTIVITY EXPRESSED BY A CELL

(71) Applicant: Merus N.V., Utrecht (NL)

(72) Inventors: Cecilia Anna Wilhelmina Geuijen, Utrecht (NL); Rinse Klooster, Utrecht (NL); Cornelis Adriaan De Kruif, Utrecht (NL); Paulus Johannes Tacken, Utrecht (NL); Mark Throsby, Utrecht (NL); Ton Logtenberg, Utrecht (NL)

(73) Assignee: MERUS N.V., Utrecht (NL)

( * ) Notice: Subject to any disclaimer, the term of this patent is extended or adjusted under 35 U.S.C. 154(b) by 23 days.

(21) Appl. No.: 16/628,939

(22) PCT Filed: Jul. 6, 2018

(86) PCT No.: PCT/NL2018/050451
§ 371 (c)(1),
(2) Date: Jan. 6, 2020

(87) PCT Pub. No.: WO2019/009728
PCT Pub. Date: Jan. 10, 2019

(65) Prior Publication Data
US 2020/0216540 A1    Jul. 9, 2020

(30) Foreign Application Priority Data
Jul. 6, 2017   (EP) .................................... 17180070

(51) Int. Cl.
*C07K 16/28* (2006.01)

(52) U.S. Cl.
CPC ...... *C07K 16/2818* (2013.01); *C07K 2317/31* (2013.01); *C07K 2317/526* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 9,248,181 B2 | 2/2016 | De Kruif et al. | |
| 9,358,286 B2 | 6/2016 | De Kruif et al. | |
| 9,701,749 B2 | 7/2017 | Shibayama et al. | |
| 2003/0078385 A1 | 4/2003 | Arathoon et al. | |
| 2017/0101472 A1 | 4/2017 | Ullman et al. | |
| 2017/0137517 A1* | 5/2017 | Bowman | C07K 16/2818 |
| 2020/0017595 A1* | 1/2020 | Geuijen | C07K 16/2878 |
| 2020/0216539 A1* | 7/2020 | Geuijen | C07K 16/2818 |
| 2020/0325227 A1* | 10/2020 | Geuijen | C07K 16/468 |
| 2022/0127375 A1* | 4/2022 | Doornbos | C07K 16/32 |

FOREIGN PATENT DOCUMENTS

| | | |
|---|---|---|
| CA | 2607147 A1 | 11/2006 |
| JP | 2015-532278 | 11/2015 |
| WO | WO-2004009618 A2 | 1/2004 |
| WO | 2006/121168 | 11/2006 |
| WO | WO-2009126920 A2 | 10/2009 |
| WO | WO-2009157771 A2 | 12/2009 |
| WO | WO-2010019570 A2 | 2/2010 |
| WO | 2010/029434 | 3/2010 |
| WO | 2010/029435 | 3/2010 |
| WO | 2012/145493 | 10/2012 |
| WO | WO-2013157953 A1 | 10/2013 |
| WO | WO-2013157954 A1 | 10/2013 |
| WO | 2014/051433 | 4/2014 |
| WO | WO-2015200119 A1 | 12/2015 |
| WO | 2016/011069 | 1/2016 |
| WO | WO-2016028672 A1 | 2/2016 |
| WO | WO-2016210129 A1 | 12/2016 |
| WO | WO-2017019846 A1 | 2/2017 |
| WO | WO-2017024515 A1 | 2/2017 |
| WO | 2017/049143 | 3/2017 |
| WO | WO-2017069628 A2 | 4/2017 |
| WO | 2018/053401 | 3/2018 |
| WO | 2018/053405 | 3/2018 |

(Continued)

OTHER PUBLICATIONS

LaMotte-Mohs R. et al. (2016) MGD013, a bispecific PD-1×LAG-3 Dual-Affinity Re-Targeting (DART®) protein with T-cell immunomodulatory activity for cancer treatment. Cancer Res (2016) 76 (14Suppl): Abstract 3217 (4 pages).*
LaMotte-Mohs R. et al. (2016) MGD013, a bispecific PD-1×LAG-3 Dual-Affinity Re-Targeting (DART®) protein with T-cell immunomodulatory activity for cancer treatment. Poster (1 page).*
Almagro J.C., et al., "Humanization of antibodies," Frontiers in bioscience 13:1619-1633, Frontiers in Bioscience Publications, United states (Jan. 2008).
Andreas L., et al., "31st Annual Meeting and Associated Programs of theSociety for Immunotherapy of Cancer (SITC 2016): Part one 1," Journal for Immunotherapy of Cancer. Biomed Central Ltd. London. UK, vol. 4(1), Nov. 16, 2016, pp. 1-106. XP021241440.
Armour, K.L., et al., "Recombinant Human IgG Molecules Lacking Fc gamma Receptor I Binding and Monocyte Triggering Activities," European Journal of Immunology 29(8):2613-2624, Wiley-VCH, Germany (Aug. 1999).

(Continued)

Primary Examiner — Ilia I Ouspenski
(74) Attorney, Agent, or Firm — Wenderoth, Lind & Ponack, L.L.P.

(57) ABSTRACT

The invention provides means and methods for interfering with Programmed Cell Death 1 protein (PD-1) and Lymphocyte activation 3 (LAG 3) mediated inhibition in a PD-1 and/or LAG3 positive cell. A method may comprise contacting said cell with an antibody or a functional part, derivative and/or analogue thereof that comprises a variable domain that can bind to an extracellular part of PD-1 and a variable domain that can bind to an extracellular part of LAG3, thereby inhibiting PD-1 and/or LAG3 mediated activity in said cell. The invention also provides antibodies or variants thereof that comprises a variable domain that can bind to an extracellular part of PD-1 and a variable domain that can bind to an extracellular part of LAG3.

22 Claims, 37 Drawing Sheets
Specification includes a Sequence Listing.

(56) References Cited

FOREIGN PATENT DOCUMENTS

| WO | WO-2018056821 A1 | 3/2018 |
|---|---|---|
| WO | WO-2018153340 A1 | 8/2018 |
| WO | WO-2018157953 A1 | 9/2018 |
| WO | WO-2018157954 A1 | 9/2018 |
| WO | 2021/243028 | 12/2021 |

OTHER PUBLICATIONS

De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).

Idusogie, E.E., et al., "Mapping of the C1q Binding Site on Rituxan, a Chimeric Antibody with a Human IgG1 Fc," The Journal of Immunology 164(8):4178-4184, American Association of Immunologists, United States (2000).

International Search Report and Written Opinion for Application No. PCT/NL2018/050451, dated Dec. 3, 2018, 27 pages.

Labrijn, A.F., et al., "Therapeutic IgG4 Antibodies Engage in Fab-arm Exchange with Endogenous Human IgG4 in Vivo," Nature Biotechnology 27(8):767-771, Nature America Publishing, United States (Aug. 2009).

Lundqvist A., et al., "31st Annual Meeting and Associated Programs of the Society for Immunotherapy of Cancer (SITC 2016): part one," Journal for Immunotherapy of Cancer 4(1):1-106, Biomed Central Ltd, United kingdom (Nov. 2016).

Marks, J.D., et al., "By-passing Immunization. Human Antibodies from V-gene Libraries Displayed on Phage," Journal of Molecular Biology 222(3):581-597, Academic Press Limited, United States (Dec. 1991).

Mohs, R.L., et al., "Mgd013, a Bispecific Pd-1 X Lag-3 Dual-affinity Re-targeting (Dart®) Protein With T-cell Immunomodulatory Activity for Cancer Treatment," Macrogenic, Apr. 20, 2016 (Apr. 20, 2016), XP055369262.

Mohs R.S., et al., "Abstract 3217: Mgd013, a Bispecific Pd-1 X Lag-3 Dual-affinity Re-targeting (Dart®) Protein With T-cell Immunomodulatory Activity for Cancer Treatment," Immunology 76(14), Cancer Research, (Jul. 2016).

Morrison, S.L., et al., "Two heads are better than one," Nature Biotechnology 25(11): 1233-1234, Nature Publishing Group, United Kingdom (2007).

Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).

\* cited by examiner

DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIK
RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC
(SEQ ID. NO: 28)

Figure 1B

```
gacatccagatgacccagtctccatcctccctgtctgcatctgtaggagacagagtcacc
 D   I   Q   M   T   Q   S   P   S   S   L   S   A   S   V   G   D   R   V   T
atcacttgccgggcaagtcagagcattagcagctacttaaattggtatcagcagaaacca
 I   T   C   R   A   S   Q   S   I   S   S   Y   L   N   W   Y   Q   Q   K   P
gggaaagcccctaagctcctgatctatgctgcatccagtttgcaaagtggggtcccatca
 G   K   A   P   K   L   L   I   Y   A   A   S   S   L   Q   S   G   V   P   S
aggttcagtggcagtggatctgggacagatttcactctcaccatcagcagtctgcaacct
 R   F   S   G   S   G   S   G   T   D   F   T   L   T   I   S   S   L   Q   P
gaagattttgcaacttactactgtcaacagagttacagtacccctccaacgttcggccaa
 E   D   F   A   T   Y   Y   C   Q   Q   S   Y   S   T   P   P   T   F   G   Q
gggaccaaggtggagatcaaa (SEQ ID. NO: 29)
 G   T   K   V   E   I   K (SEQ ID. NO: 30)
```

Figure 1C

```
cgaactgtggctgcaccatctgtcttcatcttcccgccatctgatgagcagttgaaatct
    R   T   V   A   A   P   S   V   F   I   F   P   P   S   D   E   Q   L   K   S
ggaactgcctctgttgtgtgcctgctgaataacttctatcccagagaggccaaagtacag
    G   T   A   S   V   V   C   L   L   N   N   F   Y   P   R   E   A   K   V   Q
tggaaggtggataacgccctccaatcgggtaactccaggagagtgtcacagagcaggac
    W   K   V   D   N   A   L   Q   S   G   N   S   Q   E   S   V   T   E   Q   D
agcaaggacagcacctacagcctcagcagcaccctgacgctgagcaaagcagactacgag
    S   K   D   S   T   Y   S   L   S   S   T   L   T   L   S   K   A   D   Y   E
aaacacaaagtctacgcctgcgaagtcacccatcagggcctgagctcgcccgtcacaaag
    K   H   K   V   Y   A   C   E   V   T   H   Q   G   L   S   S   P   V   T   K
agcttcaacaggggagagtgttag (SEQ ID. NO: 31)
    S   F   N   R   G   E   C   -  (SEQ ID. NO: 32)
```

Figure 1D

DIQMTQSPSSLSASVGDRVTITCRASQSISSYLNWYQQKPGKAPKLLIYAASSLQSGVPSRFSGSGSG
TDFTLTISSLQPEDFATYYCQQSYSTPPITFGQGTRLEIK (SEQ ID. NO: 33)

Figure 1E

DIQMTQSPSSLSASVGDRVTITCRASQSISSYLNWYQQKPGKAPKLLIYAASSLQSGVPSRFSGSGSG
TDFTLTISSLQPEDFATYYCQQSYSTP (SEQ ID. NO: 34)

VH: dependent on the MF (target): Figure 3.

Figure 2B

```
gctagcaccaagggcccatcggtcttccccctggcaccctcctccaagagcacctctggg
 A   S   T   K   G   P   S   V   F   P   L   A   P   S   S   K   S   T   S   G
ggcacagcggccctgggctgcctggtcaaggactacttccccgaaccggtgacggtgtcg
 G   T   A   A   L   G   C   L   V   K   D   Y   F   P   E   P   V   T   V   S
tggaactcaggcgccctgaccagcggcgtgcacaccttcccggctgtcctacagtcctca
 W   N   S   G   A   L   T   S   G   V   H   T   F   P   A   V   L   Q   S   S
ggactctactccctcagcagcgtcgtgaccgtgccctccagcagcttgggcacccagacc
 G   L   Y   S   L   S   S   V   V   T   V   P   S   S   S   L   G   T   Q   T
tacatctgcaacgtgaatcacaagcccagcaacaccaaggtggacaagagagtt (SEQ ID. NO: 35)
 Y   I   C   N   V   N   H   K   P   S   N   T   K   V   D   K   R   V (SEQ ID. NO: 36)
```

Figure 2C

```
gagcccaaatcttgtgacaaaactcacacatgcccaccgtgccca (SEQ ID. NO: 37)
 E   P   K   S   C   D   K   T   H   T   C   P   P   C   P (SEQ ID. NO: 38)
```

Figure 2D

```
gcacctgaactcctggggggaccgtcagtcttcctcttccccccaaaacccaaggacacc
 A   P   E   L   L   G   G   P   S   V   F   L   F   P   P   K   P   K   D   T
ctcatgatctcccggacccctgaggtcacatgcgtggtggtggacgtgagccacgaagac
 L   M   I   S   R   T   P   E   V   T   C   V   V   V   D   V   S   H   E   D
cctgaggtcaagttcaactggtacgtggacggcgtggaggtgcataatgccaagacaaag
 P   E   V   K   F   N   W   Y   V   D   G   V   E   V   H   N   A   K   T   K
ccgcgggaggagcagtacaacagcacgtaccgtgtggtcagcgtcctcaccgtcctgcac
 P   R   E   E   Q   Y   N   S   T   Y   R   V   V   S   V   L   T   V   L   H
caggactggctgaatggcaaggagtacaagtgcaaggtctccaacaaagccctcccagcc
 Q   D   W   L   N   G   K   E   Y   K   C   K   V   S   N   K   A   L   P   A
cccatcgagaaaaccatctccaaagccaaa (SEQ ID. NO: 39)
 P   I   E   K   T   I   S   K   A   K (SEQ ID. NO: 40)
```

Figure 2E

```
gcacctgaactcggcaggggaccgtcagtcttcctcttccccccaaaacccaaggacacc
 A  P  E  L  G  R  G  P  S  V  F  L  F  P  P  K  P  K  D  T
ctcatgatctcccggacccctgaggtcacatgcgtggtggtggacgtgagccacgaagac
 L  M  I  S  R  T  P  E  V  T  C  V  V  V  D  V  S  H  E  D
cctgaggtcaagttcaactggtacgtggacggcgtggaggtgcataatgccaagacaaag
 P  E  V  K  F  N  W  Y  V  D  G  V  E  V  H  N  A  K  T  K
ccgcgggaggagcagtacaacagcacgtaccgtgtggtcagcgtcctcaccgtcctgcac
 P  R  E  E  Q  Y  N  S  T  Y  R  V  V  S  V  L  T  V  L  H
caggactggctgaatggcaaggagtacaagtgcaaggtctccaacaaagccctcccagcc
 Q  D  W  L  N  G  K  E  Y  K  C  K  V  S  N  K  A  L  P  A
cccatcgagaaaaccatctccaaagccaaa (SEQ ID. NO: 41)
 P  I  E  K  T  I  S  K  A  K  (SEQ ID. NO: 42)
```

Figure 2F

```
gggcagccccgagaaccacaggtgtacaccaagcccccatcccgggaggagatgaccaag
 G  Q  P  R  E  P  Q  V  Y  T  K  P  P  S  R  E  E  M  T  K
aaccaggtcagcctgaagtgcctggtcaaaggcttctatcccagcgacatcgccgtggag
 N  Q  V  S  L  K  C  L  V  K  G  F  Y  P  S  D  I  A  V  E
tgggagagcaatgggcagccggagaacaactacaagaccacgcctcccgtgctggactcc
 W  E  S  N  G  Q  P  E  N  N  Y  K  T  T  P  P  V  L  D  S
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga (SEQ ID. NO: 43)
 L  S  L  S  P  G  -  (SEQ ID. NO: 44)
```

Figure 2G

```
gggcagccccgagaaccacaggtgtacaccgaccccccatcccgggaggagatgaccaag
 G  Q  P  R  E  P  Q  V  Y  T  D  P  P  S  R  E  E  M  T  K
aaccaggtcagcctgacctgcgaggtcaaaggcttctatcccagcgacatcgccgtggag
 N  Q  V  S  L  T  C  E  V  K  G  F  Y  P  S  D  I  A  V  E
tgggagagcaatgggcagccggagaacaactacaagaccacgcctcccgtgctggactcc
 W  E  S  N  G  Q  P  E  N  N  Y  K  T  T  P  P  V  L  D  S
gacggctccttcttcctctatagcaagctcaccgtggacaagagcaggtggcagcagggg
 D  G  S  F  F  L  Y  S  K  L  T  V  D  K  S  R  W  Q  Q  G
aacgtcttctcatgctccgtgatgcatgaggctctgcacaaccactacacgcagaagagc
 N  V  F  S  C  S  V  M  H  E  A  L  H  N  H  Y  T  Q  K  S
ctctccctgtctccgggttga (SEQ ID. NO: 45)
 L  S  L  S  P  G  -  (SEQ ID. NO: 46)
```

QVQLQESGPGLVKPSETLSLTCTVSTDSLG<u>FYFWS</u>WIRQPPGKGLEWIG<u>YIYYSGSAN
FNPSLKS</u>RVTMSIDTSNNQFSLKLRSVTAADTAVYFCAR<u>GGYTGYGGDWFDP</u>WGQG
TLVTVSS

MF6226

QVQLQESGPGLVKPSETLSLTCTVSGDSIG<u>YYFWS</u>WIRQPPGKGLEWIG<u>YVYYSGSNN
LNPSLKS</u>RVTLSVDTSKNQFSLRLNSMTAADTAVYYCAR<u>GGYSGYGGDSFDL</u>WGQGT
TVTVSS

MF6236

QVQLQESGPGLVKPSETLSLTCTVSGGSIG<u>YYFWS</u>WIRQPPGKGLEWIG<u>YIYYSGSTN
FNPSLKS</u>RVTMSVDTSKNQFSLNLRSVTTADTAVYYCAR<u>GGYTGHGGDWFDP</u>WGQG
TLVTVSS

MF6256

EVQLVQSGAEVKKPGSSMKVSCKASGGTFS<u>SYVIS</u>WVRQAPGQGLEWMG<u>MIIPVFDT
SSYEKKFQG</u>RITIADKSTSTVYLELSSLRSEDAAVYYCAR<u>GTVEATLLFDF</u>WGQGTLV
TVSS

MF6930

EVQLVQSGAEVKKPGSSMKVSCKASGGTFS<u>NYVIS</u>WVRQAPGQGLEWMG<u>MIIPVFET
ATYEKKFQG</u>RVTIADKSTSTVYMELSSLRSEDAAVYYCAR<u>GTVEATLLFDY</u>WGQGTL
VTVSS

MF6932

QVQLVQSGAEVKKPGSSVKVSCKASGGTFS<u>SYAIS</u>WVRQAPGQGLEWMG<u>MIIPFFDT
ANYAQKFQG</u>RVTITADKSTSTASMELRSLRSEDTAVYYCAR<u>GTVSATLVFDY</u>WGQGT
LVTVSS

QVQLVQSGAEVKKPGSSVKVSCKASGGTFS<u>SYVIS</u>WVRQAPGQGLEWMG<u>MIIPIFDT
ANYAQKFQG</u>RVTITADKSTSTASMELRSLRSEDTAVYYCAR<u>GTVSGTLVFDY</u>WGQGT
LVTVSS

MF6936

EVQLVQSGAEVKKPGSSVKVSCKASGDTFS<u>NYVIN</u>WVRQAPGQGLEWMG<u>MIIPVFDT
TSYERKFQG</u>RVTITADKSTSTAYMELTSLRSEDTAVYYCAR<u>GTVGATLLFDN</u>WGQGT
LVTVSS

MF6972

EVQLQESGPGLVKPSETLSLTCTVSGGSIS<u>TYFWS</u>WIRQPPGKGLEWIG<u>YIYSGSTNY
NPSLKS</u>RVTISVDTSKNQFSLKLSSVTAADTAVYYCAR<u>GGYSGYGGDDFDI</u>WGQGTM
VTVSS

MF6974

EVQLVESGGDLVQPGGSLRLSCAASGFTFN<u>SYAMS</u>WVRQAPGKGLEWVS<u>TISGGGA
NIYYADSVKG</u>RFTISRDNSKSTLYLQMNSLRAEDTAVYFCAS<u>PYGSGYFDV</u>WGQGTL
VTVSS

MF6982

EVQLVESGGDLVQPGGSLRLSCAASGFTFS<u>SYAMS</u>WVRQAPGKGLEWVS<u>TISGGGTN
IYYADSVKG</u>RFTISRDNSKNTLFLQMNSLRAGDTAVYYCAS<u>PYGSGYLDV</u>WGQGTLV
TVSS

EVQLVESGGGVVQPGRSLRLSCAASGFTFS<u>SYDTH</u>WVRQAPGKGLEWVA<u>VISYDGSN
KYYADSVKG</u>RFTISRDNSKNTLYLQMNSLRAEDTAMYYCAR<u>ERGWDVFDI</u>WGQGTL
VTVSS

MF7111

QVQLQESGPGLVKPSETLSLTCTVSDDSIS<u>DYYWS</u>WIRQPPGKGLEWIG<u>YIYYSGNTK
YNPSLKNR</u>VTISVDTSKSQFSLKLTSVTAADTAVYYCAR<u>IPLTGEFDY</u>WAQGTLVTVSS

MF7116

EVQLVESGGGVVQPGRSLRLSCAASGFTFS<u>SYGMH</u>WVRQAPGKGLEWVA<u>VISYHGS
DKYYADSVKG</u>RFTISRDNSKNTLYLQMNSLRAEDTAVYYCARD<u>GDNWDVFDI</u>WGQG
TLVTVSS

MF7118

EVQLVESGGGLVQPGGSLRLSCAASGFTFS<u>SYAMS</u>WVRQAPGKGLEWVS<u>SISGGGVS
TFYADSVKG</u>RFTISRDNSKNTLYLQMNSLRAEDTAVYYCAI<u>VPAAATPSGTYYWIFDL</u>
WGRGTLVTVSS

MF7134

EVQLVQSGSELKKPGASVKVSCKASGYTFT<u>TNALN</u>WVRQAPGQGLEWMG<u>WINTHTG
NPTYAQGFIGR</u>FVFSLDTSVSTAYLQIRSLKAEDTAVYYCAR<u>EPNWGVYFDY</u>WGQGT
LVTVSS

MF7136

EVQLVESGGGLVQPGGSLRLSCAASGFTFS<u>SYAMN</u>WVRQAPGKGLEWVS<u>AISGSGRS
TYYADSVKG</u>RFTISRDNSKNTLYLQMNSLRAEDTAVYYCAK<u>DSTYYYTSGSYSVFDY</u>
WGQGTLVTVSS

QVQLVQSGAEVKRPGASVKVSCKVSGYTLTELSMHWVRQAPGKGLEWMGGSDPEHGETVDAQKFQGRVTMTEDTSTDTAYMELSSLRSEDTAVYYCTTGGTYYYGSGSYYTLDFWGQGTLVTVSS

MF7142

QVQLVQSGAEVRKPGSSVMVSCKASGGTFNTYAINWVRQAPGQGLEWMGGIIPIFGTPYYGQRFQGRVTITADKSTNTVFMELSSLRSEDTAMYFCARERDIGSLYYFDSWGQGTLVTVSS

MF7146

EVQLVQSGAEVKKPGSSVKVSCKASGGTFNNYFITWVRQAPGQGLEWMGGIIPSFGTGNYAQKFQGRVAITADKSTNTAYMELSSLRSEDTAIYYCVRDREVGAIYYFDYWGQGTMVTVSS

MF7165

QVQLVQSGAEVRKPGASVKVSCKVSGYTLTELSIHWVRQAPGKGLEWMGAFDPEDGETIYAQKFQGRVTMTEDTSTDTAYMELSSLRSEDTAVYFCATGGTYYYGSGSYYTLDYWGQGTLVTVSS

MF7167

EVQLVESGGGLVQPGGSLRLSCAASGFTFSSYAMNWVRQAPGKGLEWVSTISGSGVSTYYADSVKGRFTISRDNSKNTLYLQMNTLRAEDTAVYYCAKDRGYDYSGSYHNWFDPWGQGTLVTVSS

MF7185

QVQLVQSGAEVKKPGSSVKVSCKTSGGTFSNYAFSWVRQAPGQGLEWMGGIIPIFGSTNYAQSFQGRVTITADKSTSTAYMELSSLRSEDTAVYYCARDREMGTLYFFDQWGQGTTVTVSS

EVQLLESGGGLVQPGGSLRLSCAASGFTFS<u>SYAMS</u>WVRQAPGKGLEWVS<u>AISGSGGS
TYYADSVKG</u>RFTISRDNSKNTLYLQMNSLRAEDTAVYYCAK<u>DTSTWQRGGYKAFDY</u>
WGQGTLVTVSS

MF7444

EVQLLESGGGLVQPGGSLRLSCAASGFTFS<u>SYAMS</u>WVRQAPGKGLEWVS<u>AISGSGGS
TYYADSVKG</u>RFTISRDNSKNTLYLQMNSLRAEDTAVYYCAK<u>DTGQSWSNYYHAFDY</u>
WGQGTLVTVSS

MF7515

QVQLVQSGAEVKKPGASVKVSCKASGYTFT<u>SYGIS</u>WVRQAPGQGLEWMG<u>WISAYSG
NTNYAQKLQG</u>RVTMTTDTSTSTAYMELRSLRSDDTAVYYCAR<u>RPGPALGDLDS</u>WGQ
GTLVTVSS

MF7518

QVQLVQSGAEVKKPGASVKVSCKASGYTFT<u>SYGIS</u>WVRQAPGQGLEWMG<u>WISAYSG
NTNYAQKLQG</u>RVTMTTDTSTSTAYMELRSLRSDDTAVYYCAR<u>DGSGWDDFDY</u>WGQ
GTLVTVSS

MF7096

QVQLQESGPGLVRPSETLSLTCTVSGGSIS<u>SYSWS</u>WIRQPPGKGLEWIG<u>YIDYSGSTNY
NPSLKS</u>RVTISVDTSKTQFSLKLSSVSAADTAVYYCAK<u>DLLYKWNYVEGFDI</u>WGQGTT
VTVSS

MF7097

QVQLQESGPGLVKPSETLSLTCTVSGGSIS<u>SYSWS</u>WIRQPPGKGLEWIG<u>YIDYSGTTN
FNPSLKS</u>RVTISVDTSKTQFSLKLSSVSAADTAVYYCAK<u>DLLYKWNYVEGFDI</u>WGQGT
MVTVSS

QVQLVQSGAEVKKPGSSVKVSCKASGGTFS<u>KYVVS</u>WVRQAPGQGFDWMG<u>GIIPMFG
TANYAQMFQG</u>RVTITADKSTSTVNMELSSLRSEDTAVYYCVR<u>DKAVAGLYYFDS</u>WGQ
GTLVTVSS

MF7120

QVQLVQSGAEVKKPGSSVKVSCKASGDTFS<u>TYAIN</u>WIRQAPGQGLEWMG<u>GIIPIFGTA
YYAQEFQD</u>RVTITADKSTSTGYMEMSSLISEDTAVYYCAR<u>ERELGALYAFDI</u>WGQGT
MVTVSS

MF7133

EVQLVQSGAEVKKPGSSVKVSCKASGGTFS<u>SHAIS</u>WVRQVPGQGLEWMG<u>GIIPLFDT
AKNAQKFQG</u>RVTITADKSTSTAYMELSSLRSEDTAVYYCAR<u>DRETGTLYYFDY</u>WGQG
TLVTVSS

MF7139

QVQLVQSGAEVKKPGSSVKVSCKASGGTFS<u>NFAFS</u>WVRQAPGQGLEWMG<u>GIIPMFD
TAKYAQKFQG</u>RVTIADKSTNTAYMDLNSLRSEDTAVYYCVR<u>DRAIGTLYYFDY</u>WGQ
GTLVTVSS

MF7144

QVQLVQSGAEVRKPGSSVMVSCKASGGTFS<u>TYAIN</u>WLRQAPGQGLEWMG<u>GIIPIFGT
PYYGQRFQG</u>RVTITADKSTNTVFMELSSLRSEDTAIYYCAR<u>DRDSGGLYYFDS</u>WGQG
TLVTVSS

MF7524

QVQLVQSGAEVKKPGASVKVSCKASGYTFT<u>SYGIS</u>WVRQAPGQGLEWMG<u>WISAYSG
NTNYAQKLQG</u>RVTMTTDTSTSTAYMELRSLRSDDTAVYYCAR<u>GSILAAQMWGDI</u>WG
QGTLVTVSS

FIGURE 8

EVQLVETGAEVKKPGASVKVSCKASDYIFTKYDINWVRQAPGQGLEWMGWMSANTGNIGYAQKFQGRVTMTRDTS
INTAYMELSSLTSGDTAVYFCARSSLFKTETAPYYHFALDVWGQGTTVTVSS (SEQ ID. NO: 82)

| Reporter | SEB donor 1 | SEB donor 2 | Sum | Average |
|---|---|---|---|---|
| MG6930C1873 | 3 | 0 | 3 | 1.0 |
| MG6076C1873 | 8 | 8 | 18 | 6.0 |
| MG6974C1873 | 6 | 10 | 24 | 8.0 |
| MG6973C1873 | 6 | 8 | 15 | 5.0 |
| MG6935C1873 | 0 | 1 | 4 | 1.3 |
| MG6227C1873 | 3 | 0 | 7 | 2.3 |
| MG6932C1873 | 0 | 0 | 1 | 0.3 |
| MG6983C1873 | 0 | 0 | 2 | 0.7 |
| MG6225C1873 | 0 | 0 | 0 | 0.0 |
| MG5743C1873 | 0 | 0 | 6 | 2.0 |

FIGURE 22

| | Reporter | SEB donor 1 | SEB donor 2 | Sum | Average | Ranking |
|---|---|---|---|---|---|---|
| MG7518C1624 | 2 | 1 | 2 | 5 | 1.7 | 7 |
| MG7116C1624 | 1 | 1 | 0 | 2 | 0.7 | |
| MG7111C1624 | 1 | 1 | 0 | 2 | 0.7 | |
| MG7137C1624 | 0 | 1 | 2 | 3 | 1.0 | |
| MG7100C1624 | 0 | 1 | 0 | 1 | 0.3 | |
| MG7096C1624 | 2 | 1 | 1 | 4 | 1.3 | 10 |
| MG7134C1624 | 2 | 1 | 0 | 3 | 1.0 | |
| MG7524C1624 | 4 | 2 | 3 | 9 | 3.0 | 2 |
| MG7142C1624 | 2 | 2 | 2 | 6 | 2.0 | 5 |
| MG7133C1624 | 4 | 2 | 2 | 8 | 2.7 | 3 |
| MG7097C1624 | 1 | 2 | 1 | 4 | 1.3 | 9 |
| MG7185C1624 | 1 | 2 | 3 | 6 | 2.0 | 6 |
| MG7139C1624 | 3 | 3 | 3 | 9 | 3.0 | 1 |
| MG7144C1624 | 2 | 3 | 2 | 7 | 2.3 | 4 |
| MG7106C1624 | 1 | 1 | 0 | 2 | 0.7 | |
| MG7120C1624 | 0 | 0 | 5 | 5 | 1.7 | 8 |
| MG7118C1624 | 0 | 2 | 1 | 3 | 1.0 | |
| MG7167C1624 | 0 | 1 | 0 | 1 | 0.3 | |

| | Reporter | SEB donor 1 | SEB donor 2 | Sum | Average |
|---|---|---|---|---|---|
| MG7518C1624 | 3 | 2 | 5 | 10 | 3.3 |
| MG7116C1624 | 3 | 1 | 1 | 5 | 1.7 |
| MG7111C1624 | 4 | 1 | 2 | 7 | 2.3 |
| MG7137C1624 | 0 | 1 | 2 | 3 | 1.0 |
| MG7100C1624 | 0 | 1 | 0 | 1 | 0.3 |
| MG7096C1624 | 2 | 2 | 2 | 6 | 2.0 |
| MG7134C1624 | 2 | 1 | 1 | 4 | 1.3 |
| MG7524C1624 | 5 | 2 | 4 | 11 | 3.7 |
| MG7142C1624 | 3 | 5 | 3 | 11 | 3.7 |
| MG7133C1624 | 5 | 5 | 3 | 13 | 4.3 |
| MG7097C1624 | 3 | 2 | 1 | 6 | 2.0 |
| MG7185C1624 | 2 | 3 | 4 | 9 | 3.0 |
| MG7139C1624 | 4 | 5 | 3 | 12 | 4.0 |
| MG7144C1624 | 4 | 3 | 3 | 10 | 3.3 |
| MG7106C1624 | 3 | 2 | 3 | 8 | 2.7 |
| MG7120C1624 | 2 | 2 | 5 | 9 | 3.0 |
| MG7118C1624 | 0 | 3 | 3 | 6 | 2.0 |
| MG7167C1624 | 0 | 4 | 0 | 4 | 1.3 |

FIGURE 23

| SEQ ID NOS: | Clone information | | | | Monospecific activity (as bivalent IgG) | Screening results | |
|---|---|---|---|---|---|---|---|
| | MF | CDR3 | CDR3 length | Germline | % AUC of pos cntrl | Ranking reporter | Ranking SEB assay |
| SEQ ID NO. 83 | MF6076 | GGYTGYGGDWFDP | 13 | IGHV4-59 | 49.2 | 1 | 2 |
| SEQ ID NO. 84 | MF6974 | PYGSGYFDV | 9 | IGHV3-23 | 46.5 | 2/3 | 1 |
| SEQ ID NO. 123 | MF6973 | PYGSGYFDV | 9 | IGHV3-23 | 39.1 | 2/3 | 3 |
| SEQ ID NO. 85 | MF6930 | GTVEATLLFDY | 11 | IGHV1-69 | 51.5 | 4 | |
| SEQ ID NO. 86 | MF6227 | GGYSGYGGDDFDI | 13 | IGHV4-59 | 21.5 | 5 | |
| SEQ ID NO. 87 | MF6935 | GTVSGTLVFDY | 11 | IGHV1-69 | 32.0 | | |
| SEQ ID NO. 88 | MF6932 | GTVSATLVFDY | 11 | IGHV1-69 | 15.9 | | |
| SEQ ID NO. 89 | MF6983 | PYDSGYFDV | 9 | IGHV3-23 | 11.1 | | |
| SEQ ID NO. 90 | MF6225 | GGYSGYGGDSMDV | 13 | IGHV4-59 | 7.7 | | |
| SEQ ID NO. 91 | MF5743 | AYCSGNSCYTDYFDY | 15 | IGHV3-13 | | | |

FIGURE 24

| SEQ ID NOS: | MF | CDR3 | Domain specificity | Activity bivalent (AUC, % of control) | T cell binding (AUC) monovalent | EC50 monovalent (ug/ml) | Ranking SEB and reporter |
|---|---|---|---|---|---|---|---|
| SEQ ID NO. 92 | MG7139 | DRAIGTLYYFDY | hu D2 | 20.00 | 2854 | 5.71 | 1 |
| SEQ ID NO. 93 | MG7524 | GSILAAQMWGDI | hu/mo cross-reactive – mo D1 | 29.41 | 5551 | 4.2 | 2 |
| SEQ ID NO. 94 | MG7133 | DRETGTLYYFDY | hu D2 | 26.67 | 4611 | 11.23 | 3 |
| SEQ ID NO. 95 | MG7144 | DRDSGGLYYFDS | hu D2 | 19.39 | 1896 | 10.19 | 4 |
| SEQ ID NO. 96 | MG7142 | ERDIGSLYYFDS | hu D2 | 27.62 | 5276 | 3.45 | 5 |
| SEQ ID NO. 97 | MG7185 | DREMGTLYFFDQ | hu D2 | 20.95 | 2796 | 4.49 | 6 |
| SEQ ID NO. 98 | MG7518 | DGSGWDDFDY | hu D1 + D4 | 64.71 | 12450 | 0.9 | 7 |
| SEQ ID NO. 99 | MG7120 | ERELGALYAFDI | hu D2 | 14.29 | 1597 | 66.19 | 8 |
| SEQ ID NO. 100 | MG7097 | DLLYKWNYVEGFDI | hu D1 | 21.43 | 5400 | 2.7 | 9 |
| SEQ ID NO. 101 | MG7096 | DLLYKWNYVEGFDI | hu D1 | 35.71 | 5950 | 1.66 | 10 |
| SEQ ID NO. 102 | MG7111 | IPLTGEFDY | hu D1 | 51.16 | 11445 | 1.52 | >10 |
| SEQ ID NO. 103 | MG7100 | ERGWDVFDI | hu D1 | 39.80 | 10615 | 1.14 | >10 |
| SEQ ID NO. 104 | MG7134 | EPNWGVYFDY | hu D1 | 34.29 | 10368 | 0.49 | >10 |
| SEQ ID NO. 105 | MG7116 | DGDNWDVFDI | hu D1 | 57.14 | 10307 | 0.68 | >10 |
| SEQ ID NO. 106 | MG7137 | GGTYYYGSGSYYTLDF | hu D1 | 51.16 | 8588 | 1.68 | >10 |
| SEQ ID NO. 107 | MG7106 | DKAVAGLYYFDS | hu D2 | 16.28 | 2883 | 26.52 | >10 |
| SEQ ID NO. 108 | MG7118 | VPAAATPSGTYYWIFDL | hu D3 | 2.04 | ND | ND | >10 |
| SEQ ID NO. 109 | MG7167 | DRGYDYSGSYHNWFDP | hu D4 | -1.33 | ND | ND | >10 |
| SEQ ID NO. 110 | MG7444 | DTGQSWSNYYHAFDY | hu/mo cross-reactive – mo D3 | -4.35 | ND | ND | ND |

ANTIBODIES THAT MODULATE A BIOLOGICAL ACTIVITY EXPRESSED BY A CELL

CROSS-REFERENCE TO RELATED APPLICATIONS

This application is a U.S. national stage filing of International Application No. PCT/NL2018/050451, filed Jul. 6, 2018; which claims priority to EP Application No. 17180070.9, filed Jul. 6, 2017. The entire contents of International Application No. PCT/NL2018/050451 are hereby incorporated herein by reference.

REFERENCE TO A SEQUENCE LISTING SUBMITTED ELECTRONICALLY VIA EFS-WEB

This application includes a Sequence Listing submitted electronically via EFS-Web (name: "4096_0300001_Seqlisting.txt"; size: 149,979 bytes; and created on: Mar. 29, 2022), which is hereby incorporated by reference in its entirety.

The invention relates to the field of antibodies. In particular it relates to the field of therapeutic antibodies for the treatment of diseases involving aberrant cells. More in particular it relates to antibodies that bind extracellular parts of two or more membrane associated proteins and thereby modulate biological activity expressed by a cell.

Cancer is still a major cause of death in the world, in spite of the many advances that have been made in the treatment of the disease and the increased knowledge of the molecular events that lead to cancer. Colorectal cancer (CRC), for instance, is the third most common cancer worldwide. In 2008, 1.23 million people were diagnosed with the disease. It is the second most common cancer in Europe, with around 447,000 new cases diagnosed in 2012 (13% of the total). Colorectal cancer is the fourth most common cause of cancer death, estimated to be responsible for 608,000 (EU 148,000) deaths per annum. While some new treatments have been advanced in CRC many have failed clinical testing; metastatic CRC is still largely incurable with conventional treatments. Melanoma is another example of a cancer that occurs very frequently. When detection is not early enough the cancer is likely to metastasize at which stage it is very hard to treatment. Immune-intervention treatments have been shown to be effective to at least some of the patients with metastasized melanoma. Non-small cell lung cancer is a cancer type that is rarely discovered at an early enough stage for surgery. Also these types of cancers have been successfully treatment with immune-intervention treatments.

Traditionally, most cancer drug discovery has focused on agents that block essential cell functions and kill dividing cells. However, in cases of advanced cancer, no matter how aggressively applied, even to the point where patients suffer life-threatening side-effects from the treatment, chemotherapy rarely results in a complete cure. In most cases the tumors in the patients stop growing or temporarily shrink (referred to as remission) only to start proliferating again, some times more rapidly (referred to as relapse), and become increasingly more difficult to treat. More recently the focus of cancer drug development has moved away from broadly cytotoxic chemotherapy to targeted cytostatic therapies with less toxicity. Treatment of advanced cancer has been validated clinically in leukemia and some other cancers. However, in a majority of carcinomas, targeted approaches are still proving not effective enough to completely abolish cancer in the majority of the patients.

Targeting of cancers has been achieved using a variety of different methods including for instance small molecules directed towards signaling proteins on which the cancer depends for survival and/or growth; vaccines with tumor specific proteins; cell therapies with immune cells that actively kill tumor cells and antibodies that target cytotoxic molecules to the tumor; interfere with signaling and/or that (re)direct the immune system of the host to the tumor cells.

The present invention provides novel means and methods for (re)directing immune system components. The invention also relates to means and methods for modulating a biological activity expressed by cells.

SUMMARY OF THE INVENTION

The invention provides a method for interfering with Programmed Cell Death 1 protein (PD-1) and Lymphocyte activation 3 (LAG3) mediated inhibition in a PD-1 and/or LAG3 positive cell, the method comprising contacting said cell with an antibody or a functional part, derivative and/or analogue thereof that comprises
  a variable domain that can bind to an extracellular part of PD-1 and
  a variable domain that can bind to an extracellular part of LAG3, thereby inhibiting PD-1 and/or LAG3 mediated activity in said cell.

The invention also provides a method for stimulating the formation, stability and/or activity of an immunological synapse comprising providing a system that comprises at least two cells capable of associating with each other via an immunological synapse and providing said system with an antibody or a functional part, derivative and/or analogue thereof that comprises
  a variable domain that can bind to an extracellular part of PD-1 and
  a variable domain that can bind to an extracellular part of LAG3,
  thereby stimulating the formation, stability and/or activity of an immunological synapse between said at least two cells.

Further provided is an antibody or variant thereof that comprises a variable domain that can bind to an extracellular part of PD-1 and a variable domain that can bind to an extracellular part of LAG3.

In a preferred embodiment of the invention the binding of said PD-1 binding variable domain to PD-1 blocks the binding of PD-1 to PD-L1 and/or PD-L2, preferably PD-L1. In a preferred embodiment of the invention the binding of said LAG3 binding variable domain to LAG3 blocks the binding of LAG3 to MHC class II.

The LAG-3 binding variable domain is preferably a variable domain that binds to LAG-3 extracellular domain 1, 2, 3 or 4, preferably domain 1 or domain 2.

Further provided is an antibody or variant thereof that comprises a variable domain that can bind to an extracellular part of PD-1 and a variable domain that can bind to an extracellular part of LAG3; wherein the variable domain that can bind PD-1 comprises a heavy chain variable region with a CDR3 region that comprises the amino acid sequence of the CDR3 of a variable heavy chain region of one of the VH depicted for MF6076; MF6226; MF6236; MF6256; MF6930; MF6932; MF6935; MF6936; MF6972; MF6974; or MF6982 in FIGS. 3A And 3B, preferably MF6256; MF6930; MF6076, MF6974 or MF6226, preferably MF6930, MF6076 or MF6974. In a preferred embodiment said variable domain that can bind PD-1 comprises a heavy chain variable region comprises a heavy chain variable region with a CDR1, CDR2 and CDR3 region that comprises the amino acid sequence of the CDR1, CDR2 and CDR3 of a variable heavy chain region of one of the VH depicted for MF6076; MF6226; MF6236; MF6256; MF6930; MF6932; MF6935; MF6936; MF6972; MF6974; or MF6982 in FIGS. 3A And 3B, preferably MF6256; MF6930; MF6076, MF6974 or MF6226, preferably MF6930, MF6076 or MF6974.

Further provided is an antibody or variant thereof that comprises a variable domain that can bind to an extracellular part of PD-1 and a variable domain that can bind to an extracellular part of LAG3; wherein the variable domain that can bind PD-1 comprises a heavy chain variable region that comprises the amino acid sequence of the variable heavy chain region as depicted for MF6076; MF6226; MF6236; MF6256; MF6930; MF6932; MF6935; MF6936; MF6972; MF6974; or MF6982 in FIGS. 3A And 3B, preferably MF6256; MF6930; MF6076, MF6974 or MF6226, preferably MF6930, MF6076 or MF6974, having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the VH as depicted for MF.

The variable domain that can bind to an extra-cellular part of LAG3 preferably comprises a heavy chain variable region with a CDR3 region that comprises the amino acid sequence of the CDR3 region of the variable heavy chain region as depicted for MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096. Preferably variable domain that can bind to an extra-cellular part of LAG3 and that comprises a heavy chain variable region with a CDR1, CDR2 and CDR3 region that comprises the amino acid sequence of the CDR1, CDR2 and CDR3 of a variable heavy chain region of one of the VH depicted for MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096.

The variable domain that can bind to an extra-cellular part of LAG3 preferably comprises a heavy chain variable region that comprises the amino acid sequence of the variable heavy chain region as depicted for MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the indicated MF.

An antibody of the invention preferably comprises a heavy chain variable region comprising an amino acid sequence of an MF as depicted in FIGS. 3A-3F. In a preferred embodiment the antibody further comprises a light chain variable region that comprises an amino acid sequence of a light chain variable region depicted in FIG. 1. In a preferred embodiment the light chain comprises an amino acid sequence as depicted in FIG. 1A. In a preferred embodiment the heavy chain comprises a constant region of an IgG1 antibody, preferably a human IgG1 antibody. In a preferred embodiment the CH2 region of said IgG1 constant region is engineered to reduce ADCC and/or CDC activity of the antibody. In a preferred embodiment the CH2 region comprises a sequence as depicted in FIG. 2E. In a preferred embodiment the CH3-region of the antibody is engineered to facilitate heterodimerization of the heavy chains. In a preferred embodiment one heavy chain comprises a sequence as depicted in FIG. 2F and another heavy chain comprises a sequence as depicted in FIG. 2G.

Further provided is a pharmaceutical composition that comprises one or more antibodies or variants thereof of the invention.

Also provided is a nucleic acid molecule or a collection of nucleic acid molecules that codes for a heavy chain(s) or a heavy chain variable region(s) of an antibody of the invention or a variant thereof.

Also provided is a nucleic acid molecule or collection of nucleic acid molecules that codes for an antibody of the invention.

Also provided is a cell comprising one or more nucleic acid molecules that alone or together code for an antibody or a variant thereof of the invention. Also provided are methods of producing an antibody or a variant thereof of the invention using a cell as described, preferably together with the harvesting of the antibody or variant thereof from a culture of the cells.

Further provided is a cell system that comprises an antibody or variant thereof of the invention.

Also provided is a method for the treatment of an individual that has a disease involving aberrant cells such as cancer or has a chronic infection with a virus or parasite, the method comprising administering an antibody or a variant thereof of the invention, preferably a bispecific antibody or variant thereof of the invention, to the individual in need thereof.

The invention further provides an antibody or variant thereof of the invention; preferably a bispecific antibody or variant thereof of the invention, for use in the treatment of an individual that has disease involving aberrant cells such as cancer, or a chronic infection with a virus or parasite.

Further provided is an antibody of the invention, or a variant thereof that maintains the binding specificity of said antibody, or a nucleic acid molecule or functional equivalent of the invention, for use as a medicament.

The invention further provides an antibody of the invention or a variant of said antibody that maintains the binding specificity of the antibody of the invention, for use in the treatment of an individual that has a disease that involves aberrant cells such as cancer, or that has an infection, preferably an infection with a virus or parasite.

Further provided is a use of an antibody or variant according to the invention for the preparation of a medicament for the treatment or prevention of cancer and/or an infection, preferably an infection with a virus or parasite.

In a preferred embodiment the parasite is an intracellular parasite.

Further provided is a method of stimulating an immune response in an individual against an aberrant cell in said individual, the method comprising providing (administering to) said individual with an antibody or a variant thereof, preferably a bispecific antibody or a variant thereof of the invention. The aberrant cell is preferably a cancer cell, a virus-infected cell, a parasite or a parasite infected cell. In a preferred embodiment the cell is a cancer cell or a neoplastic cell.

DETAILED DESCRIPTION OF THE INVENTION

T-cell exhaustion is mediated by several inhibitory receptors including programmed cell death protein 1 (PD1), T cell immunoglobulin and mucin domain 3 (TIM-3), and LAG3. LAG3's main ligand is MHC class II, to which it binds with higher affinity than CD4. The protein negatively regulates cellular proliferation, activation, and homeostasis of T cells, in a similar fashion to CTLA-4 and PD-1 and has been reported to play a role in Treg suppressive function. LAG3 reportedly also helps maintain CD8+ T cells in a tolerogenic state. LAG3 is known under a number of different names such as Lymphocyte Activating 3; Lymphocyte-Activation Gene 3; CD223 Antigen; Protein FDC; CD223; LAG-3; or FDC. External Ids for LAG3 are: HGNC: 6476; Entrez Gene: 3902; Ensembl: ENSG00000089692; OMIM: 153337; and UniProtKB: P18627. LAG-3 is closely related to CD4. LAG-3 is located on the human chromosome 12 (12p13.32) adjacent to the CD4 gene, and its sequence is approximately 20% identical to CD4. The LAG-3 protein binds a nonholomorphic region of major histocompatibility complex 2 (MHC class II) with greater affinity than CD4. LAG-3 is one of the various immune-checkpoint receptors that are coordinately upregulated on both regulatory T cells (Tregs) and anergic T cells. LAG-3 can negatively regulated T cell proliferation, activation and homeostasis.

Programmed Cell Death 1 protein (PD-1) is a cell surface receptor that belongs to the CD28 family of receptors and is expressed on T cells and pro-B cells. PD-1 is presently known to bind two ligands, PD-L1 and PD-L2. PD-1, functioning as an immune checkpoint, plays an important role in down regulating the immune system by inhibiting the activation of T-cells, which in turn reduces autoimmunity and promotes self-tolerance. The inhibitory effect of PD-1 is thought to be accomplished through a dual mechanism of promoting apoptosis (programmed cell death) in antigen specific T-cells in lymph nodes while simultaneously reducing apoptosis in regulatory T cells (suppressor T cells). PD-1 is also known under a number of different aliases such as PDCD1; Programmed Cell Death 1; Systemic Lupus Erythematosus Susceptibility 2; Protein PD-1; HPD-1; PD1; Programmed Cell Death 1 Protein; CD279 Antigen; CD279; HPD-L; HSLE1; SLEB2; and PD-1. External Ids for PD-1 are HGNC: 8760; Entrez Gene: 5133; Ensembl: ENSG00000188389; OMIM: 600244; and UniProtKB: Q15116. New classes of drugs that block the activity of PD-1, the PD-1 inhibitors, activate the immune system to attack tumors and are therefore used with success to treat some types of cancer.

PD-L1 is a type 1 transmembrane protein that plays a role in suppressing an immune response during particular events such as pregnancy, tissue allografts, autoimmune disease and other disease states such as hepatitis. The binding of PD-L1 to PD-1 or B7.1 (CD80) transmits an inhibitory signal which reduces the proliferation of the PD-1 expressing T cells. PD-1 is thought to be able to control the accumulation of foreign antigen specific T cells through apoptosis. PD-L1 is expressed by a variety of cancer cells and the expression thereof is thought to be at least in part responsible for a dampening of an immune response against the cancer cell. PD-L1 is a member of the B7-family of protein and is known under a variety of other names such as CD274 Molecule; CD274 Antigen; B7 Homolog 1; PDCD1 Ligand 1; PDCD1LG1; PDCD1L1; B7H1; PDL1; Programmed Cell Death 1 Ligand 1; Programmed Death Ligand 1; B7-H1; and B7-H. External Ids for CD274 are HGNC: 17635; Entrez Gene: 29126; Ensembl: ENSG00000120217; OMIM: 605402; UniProtKB: Q9NZQ7.

PD-L2 is a second ligand for PD-1. Engagement of PD-1 by PD-L2 inhibits T cell receptor (TCR)-mediated proliferation and cytokine production by CD4+ T cells. At low antigen concentrations, PD-L2/PD-1 binding inhibits B7-CD28 signals. At high antigen concentrations, PD-L2/PD-1 binding reduces cytokine production. PD-L expression is up-regulated on antigen-presenting cells by interferon gamma treatment. It is expressed in some normal tissues and a variety of tumors. PD-L1 and PD-L2 are thought to have overlapping functions and regulate T cell responses. The protein is known under a number of other names such as Programmed Cell Death 1 Ligand 2; B7 Dendritic Cell Molecule; Programmed Death Ligand 2; Butyrophilin B7-DC; PDCD1 Ligand 2; PD-1 Ligand 2; PDCD1L2; B7-DC; CD273; B7DC; PDL2; PD-1-Ligand 2; CD273 Antigen; BA574F11.2; and Btdc. External Ids for PD-L2 are HGNC: 18731; Entrez Gene: 80380; Ensembl: ENSG00000197646; OMIM: 605723; and UniProtKB: Q9BQ51.

Reference to sequence identifiers is done to identify which protein is targeted. An antibody of the invention also recognizes at least some variants thereof such as allelic variants, splice variants and mutant variants thereof as long as the epitope recognized by the respective variable domain of the antibody has not been affected. Some of the alternative names may or may not have also been used to refer to other proteins. The names are given for reference purposes only. An antibody of the invention binds to the protein as expressed on cells. It can also bind to variants of the protein as long as the epitope to which the antibody binds is available. Thus splicing variants or mutant proteins (if any) will also be bound as long as the epitope is available. The fact that the antibody binds to the indicated protein means that it can bind to protein as a property and does not imply that the antibody is actually bound to the target, although it can be. It also does not mean that the antibody does not bind to other proteins. The invention discloses an antibody or variant thereof, which is preferably a bispecific antibody or variant thereof, that binds an extracellular part of a member of the PD-1 (first membrane protein) and an extracellular part of LAG3 (second membrane protein). Such a (bispecific) antibody is further also referred to as "an antibody or bispecific antibody of the invention". Also provided are compositions and kits of parts comprising two or more (bispecific) antibodies as described herein.

Antibodies typically bind their target via the so-called antigen binding site. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain comprises a heavy chain variable region (VH) and a light chain variable region (VL). The antigen-binding site can be present in the combined VH/VL variable domain, or in only the VH region or only the VL region. When the antigen-binding site is present in one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

A protein of the invention such as an antibody typically does not bind to other proteins than the specified target protein on the membrane of cells in a post-natal, preferably adult human.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Preferably, the affinity of the separate arms of the antibodies according to the invention is in the nanomolar range. Antibodies such as the bispecific antibodies of the present invention typically comprise the constant domains (Fc part) of a natural antibody, which may be engineered as described elsewhere herein to, for instance reduce ADCC and/or CDC activity. An antibody of the invention is typically a bispecific full length antibody, preferably of the human IgG subclass.

A variable domain is composed of the variable region of a heavy chain and a variable region of a light chain. The variable region of a heavy chain is typically formed by a rearranged VDJ region. A variable region of a light chain is typically formed by a rearranged VJ region. The VDJ/VJ regions can now also be artificially produced using for instance the large body of sequence information that is available of functional antibodies.

An antibody of the invention is preferably a "full length" antibody. The term 'full length' according to the invention is defined as comprising an essentially complete antibody, without one or more artificially added moieties which a size of larger than 20 amino acid residues, such as for instance additional antigen binding sites or additional activation sites or additional ligands or additional ligand-binding moieties. A full length antibody, however, does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH for the heavy chain, and CL, VL for the light chain. The domains of the heavy chains are preferably present in the order of a natural antibody (VH-CH1-CH2-CH3, meaning that the VH domain is adjacent to the CH1 domain, followed by a CH2 domain and subsequently followed by a CH3 domain). The domains of the light chains are also preferably present in the order of a natural antibody (VL-CL: meaning that the VL domain is adjacent to the CL domain). An antibody binds to antigen via the variable domains contained in the Fab fragment portion. The antibody can interact with molecules and cells of the immune system through the constant domains, mostly through the Fc portion.

In some embodiments, an antibody of the invention is an IgG, preferably a full length IgG. Full length IgG antibodies are preferred because of their typically favorable half-life and the desire to stay as close to fully autologous (human) molecules for reasons of immunogenicity. In some embodiments, an antibody of the invention is a full length IgG1, a full length IgG2, a full length IgG3 or a full length IgG4 antibody.

Full length antibodies according to the invention encompass antibodies wherein mutations may be present that provide desired characteristics or are just alternatives to the ones in the original chain. Such mutations should not be deletions of substantial portions of any of the regions. However, antibodies wherein one or several amino acid residues are acid inserted, deleted, substituted or a combination thereof, without essentially altering the antigen binding characteristics of the resulting antibody are embraced within the term "full length antibody". For instance, an IgG antibody can have 1-20 amino acid residue insertions, substitutions, deletions or a combination thereof in the constant region.

An antibody or a functional part, derivative and/or analogue thereof of the invention is preferably a bispecific antibody or a functional part, derivative and/or analogue thereof. In a preferred embodiment it is a bispecific IgG antibody with reduced effector function. In a preferred embodiment an antibody of the invention is a bispecific full length antibody. An antibody of the invention is preferably a bispecific full length IgG antibody, preferably mutated in the CH2/lower hinge region to reduce effector function. IgG1 which is mutated in the CH2/lower hinge region to reduce effector function is favored based on its long circulatory half-life in man. In order to prevent any immunogenicity in humans it is preferred that the bispecific antibody according to the invention is a human antibody.

The term 'bispecific' (bs) means that one part of the antibody (as defined above) binds to one epitope on an antigen whereas a second part binds to a different epitope on either the same antigen, or a different antigen. The different epitopes are typically present on different antigens. The different epitopes can, however, also be present on the same antigen. According to the present invention, said first and second antigens are in fact two different proteins. A preferred bispecific antibody is an antibody that comprises parts of two different monoclonal antibodies and consequently can bind to two different epitopes, preferably on two different antigens. Dependent on the expression level, (sub-)cellular localization and stoichiometry of the two antigens recognized by a bispecific antibody, both Fab arms of the antibody may or may not simultaneously bind their epitope.

One arm of the bispecific antibody typically contains the variable domain of one antibody and the other arm contains the variable domain of another antibody (i.e. one arm of the bispecific antibody is formed by one heavy chain paired with one light chain whereas the other arm is formed by a different heavy chain paired with a light chain). The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same or a common, light chain variable region is also referred to as a bispecific antibody with a common light chain variable region (cLcv). It is preferred that the light chain constant region is also the same. Such bispecific antibodies are referred to as having a common light chain (cLc). Further provided is therefore a bispecific antibody according to the invention, wherein both arms comprise a common light chain.

Bispecific antibodies as described herein preferably comprise a common light chain variable domain, preferably a common light chain. The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common LC', 'cLC', 'single light chain' with or without the addition of the term 'rearranged' are all used herein interchangeably. The terms 'common light chain variable region', 'common VL', 'common LCv', 'cLCv', 'single VL' with or without the addition of the term 'rearranged' are all used herein interchangeably. It is a preferred aspect of the present invention that a bispecific antibody has a common light chain (variable region) that can combine with at least two, and preferably a plurality of heavy chains (variable regions) of different binding specificity to form antibodies with functional antigen binding domains (WO2009/157771). The common light chain (variable region) is preferably a human light chain (variable region). A common light chain (variable region) preferably has a germline sequence. A preferred germline sequence is a light chain variable region that is frequently used in the human repertoire and has good thermodynamic stability, yield and solubility. A preferred germline light chain is O12. A common light chain is preferably the rearranged germline human kappa light chain IgVκ1-39*01/IGJκ1*01 (FIG. 1A). The common light chain variable region is preferably the variable region of the rearranged germline human kappa light chain IgVκ1-39*01/IGJκ1*01. A common light chain preferably comprises a light chain variable region as depicted in FIG. 1B, or 1D with 0-5 amino acid insertions, deletions, substitutions, additions or a combination thereof. The common light preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

In a preferred embodiment the light chain comprises a light chain region comprising the amino acid sequence of an O12/IgVκ1-39*01 gene segment as depicted in FIG. 1A with 0-10, preferably 0-5 amino acid insertions, deletions, substitutions, additions or a combination thereof. The phrase "O12 light chain" will be used throughout the specification as short for "a light chain comprising a light chain variable region comprising the amino acid sequence of an O12/IgVκ1-39*01 gene segment as depicted in FIG. 1A with 0-10, preferably 0-5 amino acid insertions, deletions, substitutions, additions or a combination thereof. IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 1E. This lists the sequence of the V-region. The V-region can be combined with one of five J-regions. FIGS. 1B and 1D describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

It is preferred that the O12/IgVκ1-39*01 comprising light chain variable region is a germline sequence. It is further preferred that the IGJκ1*01 or/IGJκ5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline O12/IgVκ1-39*01. In a preferred embodiment the light chain variable region comprises the kappa light chain IgVκ1-39*01/IGJκ1*01 or IgVκ1-39*01/IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01, preferably a germline IgVκ1-39*01/IGJκ1*01.

Mature B-cells that produce an antibody with an O12 light chain often produce a light chain that has undergone one or more mutations with respect to the germline sequence, i.e. the normal sequence in non-lymphoid cells of the organism. The process that is responsible for these mutations is often referred to as somatic (hyper)mutation. The resulting light chain is referred to as an affinity matured light chain. Such light chains, when derived from an O12 germline sequence are O12-derived light chains. In this specification, the phrase "O12 light chains" will include O12-derived light chains, The mutations that are introduced by somatic hypermutation can of course also be introduced artificially in the lab. In the lab also other mutations can be introduced without affecting the properties of the light chain in kind, not necessarily in amount. A light chain is at least an O12 light chain if it comprises a sequence as depicted in FIG. 1A, FIG. 1; FIG. 1D or FIG. 1E with 0-10, preferably 0-5 amino acid insertions, deletions, substitutions, additions or a combination thereof. In a preferred embodiment the O12 light chain is a light chain comprising a sequence as depicted in FIG. 1A; 1B; 1D or 1E with 0-9, 0-8, 0-7, 0-6, 0-5, 0-4 amino acid insertions, deletions, substitutions, additions or a combination thereof. In a preferred embodiment the O12 light chain is a light chain comprising a sequence as depicted in FIG. 1A, FIG. 1; FIG. 1D or FIG. 1E with 0-5, preferably 0-4, more preferably 0-3 amino acid insertions, deletions, substitutions, additions or a combination thereof. In a preferred embodiment the O12 light chain is a light chain comprising a sequence as depicted in FIG. 1A, FIG. 1; FIG. 1D or FIG. 1E with 0-2, more preferably 0-1, most preferably 0 amino acid insertions, deletions, substitutions, additions or a combination thereof. In a preferred embodiment the O12 light chain is a light chain comprising a sequence as depicted in FIG. 1A or FIG. 1B with the mentioned amino acid insertions, deletions, substitutions, additions or a combination thereof. In a preferred embodiment the light chain comprises the sequence of FIG. 1A. In a preferred embodiment the light chain variable region comprises the sequence of FIG. 1.

The common light chain (variable region) can be a lambda light chain and this is therefore also provided in the context of the invention, however a kappa light chain is preferred. The constant part of a common light chain of the invention can be a constant region of a kappa or a lambda light chain. It is preferably a constant region of a kappa light chain, preferably wherein said common light chain is a germline light chain, preferably a rearranged germline human kappa light chain comprising the IgVK1-39 gene segment, most preferably the rearranged germline human kappa light chain IgVK1-39*01/IGJK1*01 (FIG. 1). The terms rearranged germline human kappa light chain IgVκ1-39*01/IGJκ1*01, IGKV1-39/IGKJ1, huVκ1-39 light chain or in short huVκ1-39, or simply 1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not influence the formation of functional binding regions.

IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 1. This lists the sequence of the V-region. The V-region can be combined with one of five J-regions. FIG. 1 describes two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

A common light chain variable region is preferably linked to a kappa light chain constant region. In a preferred embodiment the light chain comprises the kappa light chain IgVκ1-39*01/IGJκ1*01 or IgVκ1-39*01/IGJκ5*01. In a preferred embodiment a IgVκ1-39*01/IGJκ1*01.

A cell that produces a common light chain can produce for instance rearranged germline human kappa light chain IgVκ1-39*01/IGJκ1*01 and a light chain comprising the variable region of the mentioned light chain fused to a lambda constant region.

Bispecific antibodies or variants thereof as described herein preferably have one heavy chain variable region/light chain variable region (VH/VL) combination that binds an extracellular part of PD-1 and a second VH/VL combination that binds an extracellular part of LAG3. In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds an extracellular part of PD-1 and one H/L chain combination that binds an extracellular part of LAG3. In a preferred embodiment the light chain in said first H/L chain combination is similar to the light chain in said second H/L chain combination. In a more preferred embodiment, the light chains in the first and second H/L chain combinations are identical.

Several methods have been published to favor the production of the bispecific antibody or vice versa, the monospecific antibodies. In the present invention it is preferred that the cell favors the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two mono-specific, bivalent antibodies, and AB is a designation for the bispecific antibody. To increase the percentage of the desired bispecific product (AB) CH3 engineering can be employed, or in other words, one can use heavy chains with compatible heterodimerization domains, as defined hereunder. The art describes various ways in which such hetero-dimerization of heavy chains can be achieved. One way is to generate 'knob into hole' bispecific antibodies. See US Patent Application 20030078385 (Arathoon et al.).

The term 'compatible hetero-dimerization domains' as used herein refers to protein domains that are engineered such that engineered domain A' will preferentially form heterodimers with engineered domain B' and vice versa, homo-dimerization between A'-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286) and PCT/NL2013/050294 (published as WO2013/157954); incorporated herein by reference) methods and means are disclosed for producing bispecific antibodies using compatible heterodimerization domains. These means and methods can also be favorably employed in the present invention. Specifically, a bispecific antibody of the invention preferably comprises mutations to produce essentially only bispecific full length IgG molecules. Preferred mutations are the amino acid substitutions L351K and T366K (EU numbering) in the first CH3 domain (the 'KK-variant' heavy chain) and the amino acid substitutions L351D and L368E in the second domain (the 'DE-variant' heavy chain), or vice versa. It was previously demonstrated in our U.S. Pat. Nos. 9,248,181 and 9,358,286 patents as well as the WO2013/157954 PCT application that the DE-variant and KK-variant preferentially pair to form heterodimers (so-called 'DEKK' bispecific molecules). Homodimerization of DE-variant heavy chains (DEDE homodimers) hardly occurs due to repulsion between the charged residues in the CH3-CH3 interface between identical heavy chains.

Bispecific antibodies can be generated by (transient) transfection of a plasmid encoding a light chain and two different heavy chains that are CH3 engineered to ensure efficient hetero-dimerization and formation of the bispecific antibodies. The production of these chains in a single cell leads to the favored formation of bispecific antibodies over the formation of monospecific antibodies. Preferred mutations to produce essentially only bispecific full length IgG1 molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa.

The Fc region mediates effector functions of an antibody, such as complement-dependent cytotoxicity (CDC), antibody-dependent cellular cytotoxicity (ADCC) and antibody-dependent cell phagocytosis (ADCP). Depending on the therapeutic antibody or Fc fusion protein application, it may be desired to either reduce or increase the effector function. Reduced effector functions are preferred in the present invention. Reduced effector function can be desired when an immune response is to be activated, enhanced or stimulated as in some of the embodiments of the invention. Antibodies with reduced effector functions can be used to target cell-surface molecules of immune cells, among others.

Binding of IgG to the FcγRs or C1q was found to require residues located in the hinge region and the CH2 domain. Two regions of the CH2 domain (FIG. 2D) are relevant for FcγRs and C1q binding. Substitutions into human IgG1 of IgG2 residues at positions 233-236 and IgG4 residues at positions 327, 330 and 331 were shown to greatly reduce ADCC and CDC (Armour et al., 1999. Eur J Immunol. 29(8):2613-24; Shields et al., 2001. J Biol Chem. 276(9): 6591-604). Furthermore, Idusogie et al. demonstrated that alanine substitution at different positions, including K322, significantly reduced complement activation (Idusogie et al., 2000. J Immunol. 164(8):4178-84.

Due to their reduced effector functions, IgG4 antibodies represent an IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation is an example of a mutation that ensures reduced capacity to Fab-arm exchange. (Labrijn. et al., 2009. Nat Biotechnol. 27(8):767-71.

Antibodies with reduced effector functions are preferably IgG antibodies comprising a modified CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to a Fc-gamma receptor is reduced. An antibody comprising a mutant CH2 region is preferably an IgG1 antibody. Such a mutant IgG1 CH2 and/or lower hinge domain preferably comprise an amino substitution at position 235 and/or 236 (numbering according to EU numbering), preferably an L235G and/or G236R substitution (FIG. 2E).

A variant of an antibody or bispecific antibody as described herein comprises a functional part, derivative and/or analogue of the antibody or bispecific antibody. The variant maintains the binding specificity of the (bispecific) antibody. The functional part, derivative and/or analogue maintains the binding specificity of the (bispecific) antibody. Binding specificity is defined by capacity to bind an extracellular part of PD-1 and LAG3 as described herein.

A functional part of an antibody, or preferably a functional part of a bispecific antibody as described herein is a part comprising a variable domain that binds an extracellular part of PD-1 and a variable domain that binds an extracellular part of LAG3. A suitable part is for instance an F(ab')2 fragment as created by digestion of a bispecific antibody with pepsin. Other parts comprising said variable domains are included in the present invention.

A functional derivative of an antibody, or preferably a functional derivative of a bispecific antibody as described herein is a protein comprising a variable domain that binds an extracellular part of PD-1 and a variable domain that an extracellular part of LAG3 that are linked by a linker. The variable domains may be variable domains as such, or Fab fragments or variable domain like molecules such as single chain Fv fragments comprising a VH and a VL linked together via a linker. Other examples of variable domain like molecules are so-called single domain antibody fragment. A single-domain antibody fragment (sdAb) is an antibody fragment with a single monomeric variable antibody region. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. Other non-limiting examples of variable domain-like molecules are VHH, Human Domain Antibodies (dAbs) and Unibodies. Preferred functional parts are parts that comprise variable domains comprising a heavy chain variable region and a light chain variable region. Non-limiting examples of such variable domains are F(ab)-fragments and Single chain Fv fragments. Bispecific formats for variable domain(-like) linkage are for instance Human Serum Albumine (HSA) bound to two different scFv; bispecific mini-antibodies comprising two different scFv bound together via a dimerization motifs or self-associating secondary structures such as helix bundles or coiled coils to bring about dimerization of the scFv fragments (Morrison (2007) Nat. Biotechnol 25:1233-34). Examples of suitable HSA linkers and method for coupling scFv to the linker are described in WO2009/126920.

An antibody or functional part, derivative and/or analogue thereof or preferably a bispecific antibody or functional part, derivative and/or analogue thereof of the present invention is preferably used in humans. To this end an antibody or functional part, derivative and/or analogue thereof of the invention is preferably a human or humanized antibody. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention preferably comprises a human heavy chain constant region, preferably comprising a sequence as depicted in FIG. 2; and a human light chain constant region, preferably comprising a sequence as depicted in FIG. 1C. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from common light chain mice immunized with the respective target as described in WO2009/157771. Various antibodies produced herein are derived from a human antibody variable domain library. As such these variable domains are human. The unique CDR regions may be derived from humans, be synthetic or derived from another organism. The variable region is at least a human variable region when it has with the exception of the CDR regions, an amino acid sequence that is identical to an amino acid sequence of the variable region of a naturally occurring human antibody. In such embodiments the VH of a variable domain of an antibody that binds an extracellular part of PD-1 or LAG3, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; de-immunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

De-immunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

An antibody or bispecific antibody or functional part, derivative and/or analogue thereof according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG constant regions, i.e. selected from the group consisting of IgG1, IgG2, IgG3 and IgG4. Preferably said constant region is preferably an IgG4 or IgG1 constant region (FIG. 2), more preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region. The constant region may be mutated as indicated herein for enabling efficient heterodimerization, for reducing effector function or for other reasons including half-life, stability and the like.

Rational methods have evolved toward minimizing the content of non-human residues in the human context. Various methods are available to successfully graft the antigen-binding property of an antibody onto another antibody. The binding properties of antibodies may rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagro1 and J. Fransson (2008) Frontiers in Bioscience 13, 1619-1633, which is included by reference herein.

The light chain variable region of a variable domain comprising a variable heavy chain sequence as depicted in FIGS. 3A-3F, is preferably a germline light chain of or based on O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain. A preferred sequence for the common light chain is depicted in FIG. 1.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. The two essentially identical light chains can be light chains with essentially the same light chain variable regions and different light chain constant regions or, preferably, two essentially identical light chain constant regions. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two essentially different light chains. The ratio of bispecific antibody that is produced by the cell can be further improved by stimulating the pairing of two different heavy chains with each other over the pairing of two identical heavy chains. The art describes various ways in which such hetero-dimerization of heavy chains can be achieved. A preferred method is described in U.S. provisional application 61/635,935, which has been followed up by U.S. regular application Ser. No. 13/866,747 and PCT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell. The host cell comprises at least one light chain, and preferably a common light chain.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that can bind to an extracellular part of PD-1 and that contains a 1st CH3 domain, and b) a second nucleic acid molecule encoding a heavy chain comprising an antigen-binding site that can bind to an extracellular part of LAG3 and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it is the rearranged germline human kappa light chain IgVκ1 39*01/IGJκ1*01, as described above. Means for preferential pairing of said 1st and said 2nd CH3 domain are preferably the corresponding mutations in the CH3 domain of the heavy chain coding regions. The preferred mutations to produce essentially only bispecific antibodies are the amino acid substitutions L351K and T366K (numbering according to EU numbering) in the first CH3 domain and the amino acid substitutions L351D and L368E in the second CH3 domain, or vice versa (FIG. 2). Further provided is therefore a method according to the invention for producing a bispecific antibody, wherein said first CH3 domain comprises the amino acid substitutions L351K and T366K (numbering according to EU numbering) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH3 domain comprises the amino acid substitutions L351D and L368E (numbering according to EU numbering) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

A variable domain that "blocks" the binding of PD-1 to PD-L1 and/or PD-L2 interferes with binding of PD-1 to PD-L1 and/or PD-L2. Such a variable domain can bind PD-1. Such a blocking variable domain can bind an epitope on PD-1 and competes with PD-L1 and/or PD-L2 for binding to the epitope. Such a blocking variable domain and PD-L1 and/or PD-L2 can also bind to different epitopes on PD-1. In such cases the blocking activity can for instance be due to diminished binding of the PD-L1 and/or PD-L2, displacement of PD-L1 and/or PD-L2 when it is already bound to PD-1 or can prevent binding to PD-1 through steric hindrance. All these and other mechanisms can, at least partially, prevent that said binding partner binds to said first membrane protein.

A variable domain that "blocks" the binding of LAG3 to MHC class II interferes with binding of LAG3 to MHC class II. Such a variable domain binds LAG3. Such a blocking variable domain binds an epitope on LAG3 and competes with MHC class II for binding to the epitope. Such a blocking variable domain and MHC class II can also bind to different epitopes on LAG3. In such cases the blocking activity can be due to diminished binding of the PD-L1 and/or PD-L2, displacement of MHC class II when it is already bound to LAG3 or prevent binding to LAG3 through steric hindrance. All these and other mechanisms can, at least partially, prevent that said binding partner bind to said first membrane protein.

The LAG3 ectodomain is composed of four Ig-like domains (D1-D4). The first two N-terminal domains of LAG-3 (D1 and D2) are capable of binding MHC class II. In the present invention it was found that an antibody comprising a variable domain that binds an extracellular part of PD-1 as specified herein and a variable domain that binds an extracellular part of LAG-3 is effective in stimulating an immune response and/or stimulating the formation, stability and/or activity of an immunological synapse. This is so when the variable domain that binds LAG-3 binds extracellular domain 1, extracellular domain 2, extracellular domain 3 or extracellular domain 4 of LAG-3. It is preferred that the variable domain that binds LAG-3 binds extracellular domain 1 or extracellular domain 2. Such variable domains are more effective in the context of an antibody as described herein. In one embodiment the variable domain that binds LAG-3 binds extracellular domain 2 of LAG-3.

A variable domain that blocks the binding of a specific binding pair (i.e. PD-1/PD-L1; PD-1/PD-L2 or LAG3/MHC class II) as described herein typically reduces binding of the pair when compared to the binding in the absence of the variable domain. This is preferably measured in an in vitro assay. Typically this is done by incubating the variable domain with the membrane protein that it can bind to and subsequently incubating the mixture with the other member of the pair. The binding of the pair is then compared with the binding of the pair in the absence of the variable domain. A variable domain can completely prevent the binding of the first membrane protein to a binding partner thereof. It can also partially prevent the binding of the binding pair. A variable domain that blocks the binding of a specific binding pair of membrane proteins preferably reduces binding of the pair by at least 50%, preferably at least 60%, preferably at least 70%, preferably at least 80%, and more preferably at least 90% when compared to the binding in the absence of the variable domain. Blocking of binding by a variable domain is defined herein as the blocking obtained using a bivalent monoclonal antibody comprising said two of the same of said variable domains. The variable domain of course also blocks the binding when present in an antibody comprising said variable domain and a variable domain that binds a second membrane protein.

Specific variable domains that can bind an extracellular part of PD-1 and that at least partially block the binding of PD-1 to PD-L1 and/or PD-L2 are variable domains that comprise the amino acid sequence of the VH of: MF6076; MF6226; MF6236; MF6256; MF6930; MF6932; MF6935; MF6936; MF6972; MF6974; or MF6982 in FIGS. 3A and 3B, preferably MF6256; MF6930; MF6076, MF6974 or MF6226, preferably MF6930, MF6076 or MF6974. Specific variable domains that can bind an extracellular domain of LAG3 and that block the binding of LAG3 to MHC class II are variable domains that comprise the amino acid sequence of the VH of MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096.

The invention also provides a method of engaging and/or activating T-cells comprising providing a system comprising a T-cell and a cell (second cell) to which said T-cell is to be engaged or activated, and providing said system with at least one antibody, preferably at least one bispecific antibody, that comprises a variable domain that can bind PD-1 and a variable domain that can bind LAG3 and incubating said system under conditions that are permissive for the T-cell to become engaged and/or activated. In some embodiments, said method is an in vitro method. The cell to which said T-cell is to be engaged or activated is preferably an immune cell, for example an antigen presenting cell, a macrophage, a neoplastic cell, a virus infected cell, or an intracellular parasite infected cell. Engaging and/or activating T-cells directs T-cells to a specific target. Activating a T-cell is activating the T-cell receptor of said T-cell. Engaging a T-cell typically is activating a T-cell. Engagement can also direct an already activated T-cell to a target specified by the antibody. Conditions that are permissive for said T-cell to become engaged and/or activated are typically culture conditions but can also be incubation in a non-human animal. The conditions are such that the T-cell is not engaged in the absence of the antibody. If collections of T-cells are measured some of these can be already engaged or activated provided that the collection contains sufficient T-cells that are not engaged or activated.

An antibody of the invention can bring two cells together in close proximity that allows the interactions between the cells mediated by proteins other than the PD-1 and LAG3 bound by the antibody of the invention. One such interaction is an interaction of a T-cell receptor of one cell and MHC on the other cell.

In one aspect the invention provides a method for interfering with PD-1 and/or LAG3 mediated inhibition in a PD-1 and/or LAG3 positive cell, the method comprising contacting said cell with an antibody or a functional part, derivative and/or analogue thereof that comprises a variable domain that can bind to an extracellular part of PD-1 and a variable domain thereof that can bind to an extracellular part of LAG3, thereby inhibiting PD-1 and/or LAG3 mediated activity in said cell.

A LAG3 or PD-1 positive cell expresses the membrane protein on the cell membrane in amounts that can be detected, typically by means of immune fluorescence with a monoclonal antibody specific for the membrane protein. The PD-1 positive cell is a T-cell. The LAG3 cell is preferably a T-cell, more preferably a so-called exhausted T-cell. T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. An antibody of the invention interferes with PD-1 and LAG3 mediated inhibition by binding to the respective membrane proteins and preventing stimulation of the proteins by the respective binding partners of the protein. Known binding partners for PD-1 are PD-L1 and PD-L2. A known binding partner of LAG3 is MHC class II. The antibody blocks the interaction of PD-1 with PD-L1 and/or PD-L2; and/or LAG3 and MHC class II and thereby at least in part prevents the inhibitory activity of the PD-1 in the PD-1 positive cell; and/or the inhibitory activity of LAG3 in a LAG3 positive cell. In a preferred embodiment of the invention the binding of said PD-1 binding variable domain to PD-1 blocks the binding of PD-1 to PD-L1 and/or PD-L2, preferably PD-L1. In a preferred embodiment of the invention the binding of said LAG3 binding variable domain to LAG3 blocks the binding of LAG3 to MHC class II. Inhibition of the PD-1 and/or LAG3 mediated activity in said cell can be measured in various ways. Typically, though not necessarily, the activity is measured by measuring activation of CD4+ or CD8+ T cells. This can be done by using healthy CD4+ or CD8+ T cells, but an effect on exhaustion is typically best measured on exhausted T-cells. Such T-cells are, for instance, positive for LAG3. Activity is preferably measured in HIV-specific T-cells, preferably collected from subjects with progressive disease. Proliferation is a suitable parameter. Proliferation rates can be determined in the presence and the absence of the antibody. Differences in proliferation rates are a measure for the level of inhibition of the activity of LAG3 and or PD-1 in these cells. Other examples of suitable T-cells are TIL collected from subjects with non-small-cell lung carcinoma (NSCLC). Interferon-gamma production is a suitable parameter. Interferon-gamma production can be determined in the presence and the absence of the antibody. Differences in Interferon-gamma production are a measure for the level of inhibition of the activity of LAG3 and or PD-1 in these cells. An increase in the proliferation and/or interferon-gamma production is indicative for inhibition of the activity of LAG3 and or PD-1 in these cells. In a preferred embodiment the increase is an increase of at least 10%, preferably at least 20% more preferably at least 40% more preferably at least 80% over the level or rate detected in the absence of the antibody.

The invention further provides a method for stimulating the formation, stability and/or activity of an immunological synapse comprising providing a system that comprises at least two cells capable of associating with each other via an immunological synapse and providing said system with an antibody or a functional part, derivative and/or analogue thereof that comprises
  a variable domain that can bind to an extracellular part of PD-1 and
  a variable domain that can bind to an extracellular part of LAG3,
  thereby stimulating the formation, stability and/or activity of an immunological synapse between said at least two cells.

The antibody facilitates the formation, stability and/or activity of an immunological synapse by binding to PD-1 and/or LAG3 on a cell that contains the PD-1 or LAG3 on the cell membrane. The binding inhibits the activity of PD-1 and/or LAG3. This has the effect that the formation, stability and/or activity of an immunological synapse is stimulated. The variable domain that can bind PD-1 preferably blocks the binding of PD-1 to PD-L1 and/or PD-L2, preferably PD-L1. The variable domain that can bind LAG3 preferably blocks the binding of LAG3 to MHC class II. Said two cells are cells that are capable of forming an immunological synapse. At least one of the cells is a T-cell receptor positive cell. The other cell is typically, though not necessarily an antigen presenting cell. An immunological synapse forms as a result of the tight apposition of a T cell with an antigen-presenting cell (APC) and it is the site where the T-cell receptor (TCR) is triggered by its antigen ligand, the peptide-MHC complex present in the APC membrane. The immunological synapse in the T-cell membrane typically has three concentric rings of membrane receptors and their underlying cytoskeletal and signaling proteins. The inner circle, or central supramolecular activation cluster (cSMAC), concentrates most of the TCR and CD28, and it is surrounded by the peripheral SMAC that is formed by integrins. Finally, the most external ring or distal SMAC (dSMAC) is where proteins with large ectodomains are located, such as CD43 and CD45, far from the cSMAC.

The invention further provides an antibody or variant thereof that comprises a variable domain that can bind to an extracellular part of PD-1 and a variable domain that can bind to an extracellular part of LAG3.

In a preferred embodiment of a method, antibody (or variant thereof) or use of the invention the variable domain that binds PD-1 blocks the binding of PD-1 to PD-L1 and/or PD-L2. The variable domain that binds LAG3 preferably blocks the binding of LAG3 to MHC class II. Preferably both variable domains block the binding of the respective binding partners.

The variable domain that binds an extracellular part of PD-1 is preferably defined as a variable domain that when in a bivalent monospecific antibody format that comprises two of said variable domains that bind PD-1, inhibits PD-1/PD-L1 mediated inhibition of T cell receptor mediated activation of a Jurkat cell in a range of 20-150% when compared to the inhibition obtained with the antibody Nivolumab on a Jurkat cell.

The inhibition of PD-1 inhibition of TCR mediated activation of the Jurkat cell is preferably in the range of 50-150%, preferably 80-150%, more preferably 100-150% when compared to the inhibition obtained with the antibody Nivolumab on said Jurkat cell. In a preferred embodiment the inhibition is at least 100% when compared to the inhibition obtained with the antibody Nivolumab on said Jurkat cell. PD-1 inhibition of TCR mediated activation of Jurkat cells is preferably measured by measuring an immune dampening effect of PD-1/PD-L1 binding in Jurkat cells that are incubated under conditions that would, but for the presence of the antibody or functional part, derivative and/or analogue thereof, be activated via the T-cell receptor.

The invention further provides a composition or kit of parts comprising two or more antibodies or functional parts, derivatives and/or analogues thereof, that comprise a variable domain that can bind to an extracellular part of PD-1 and a variable domain that can bind to an extracellular part of a LAG3;
  wherein a first and a second of said antibodies or functional parts, derivatives and/or analogues thereof bind
    different epitopes on PD-1;
    different epitopes on LAG3; or
    different epitopes on PD-1 and LAG3. Embodiments comprising a method, a use, a composition or kit of parts involving two or more antibodies or functional parts, derivatives and/or analogues thereof that have variable domains that bind PD-1 and LAG3 as specified in this paragraph are also referred to as "Oligoclonics" embodiments. Examples of such Oligoclonics embodiments are embodiments with said first and second antibody. 'Oligoclonics' is a registered trademark. General methods for making such Oligoclonics® products are disclosed in WO 2013/157953 and WO2004/009618 and are incorporated here by reference.

In Oligoclonics embodiments the first and second antibody comprise variable domains that bind PD-1 and LAG3. Antibodies that have variable domains that bind the same PD-1 or LAG3 can bind the same individual protein, but this is not necessarily so. An antibody of the invention that binds to PD-1 or LAG3 binds an epitope on said protein. An epitope is the part of an antigen, in this case the membrane protein that is recognized by the antibody. First and second antibodies that bind different epitopes on a membrane protein can bind the same individual protein on the membrane. To this end the different epitopes are preferably non-overlapping epitopes. In other words the different epitopes are sufficiently separated on the membrane protein that two antibodies can bind simultaneously to the same individual protein. It was surprisingly found that Oligoclonics (a combination of a first and second or more antibodies) can be more effective than the same amount of each of the antibodies alone.

Preferably at least one of the two or more antibodies or functional parts, derivatives and/or analogues comprises a PD-1 binding variable domain that blocks the binding of PD-1 to PD-L1 and/or PD-L2, preferably PD-L1. In a preferred embodiment at least two of the two or more antibodies or functional parts, derivatives and/or analogues comprise a PD-1 binding variable domain that blocks the binding of PD-1 to PD-L1 and/or PD-L2, preferably PD-L1.

Preferably at least one of the two or more antibodies or functional parts, derivatives and/or analogues comprises a LAG3 binding variable domain that blocks the binding of LAG3 to MHC class II. In a preferred embodiment at least two of the two or more antibodies or functional parts, derivatives and/or analogues comprise a LAG3 binding variable domain that blocks the binding of LAG3 to MHC class II.

Preferably at least one of the two or more antibodies or functional parts, derivatives and/or analogues comprises a PD-1 binding variable domain that blocks the binding of PD-1 to PD-L1 and/or PD-L2, preferably PD-L1 and a LAG3 binding variable domain that blocks the binding of LAG3 to MHC class II. Preferably at least two of the two or more antibodies or functional parts, derivatives and/or analogues comprise a PD-1 binding variable domain that blocks the binding of PD-1 to PD-L1 and/or PD-L2, preferably PD-L1 and a LAG3 binding variable domain that blocks the binding of LAG3 to MHC class II.

In one aspect the invention provides methods and uses as described herein wherein two or more antibodies or functional parts, derivatives and/or analogues thereof are used and wherein the two or more antibodies or functional parts, derivatives and/or analogues thereof comprise a variable domain that can bind to an extracellular part of PD-1 and a variable domain that can bind to an extracellular part of a LAG3;

wherein a first and a second of said antibodies or functional parts, derivatives and/or analogues thereof bind
different epitopes on PD-1;
different epitopes on LAG3; or
different epitopes on PD-1 and LAG3. The preference for blocking binding of PD-L1 and/or PD-L1 by the variable domains that bind PD-1; and the blocking of binding of LAG3 to MHC class II by the variable domains that bind LAG3 are the same as a described in the Oligoclonics embodiments.

An antibody or a part, derivative, or analogue thereof, preferably comprises two variable domains as described. Such an antibody is preferably a bispecific antibody or a functional part derivative or analogue thereof. Two or more antibodies or functional parts, derivatives and/or analogues thereof can be linked together. Various methods are known in the art. A suitable method is conjugation. In addition, the technology of making multi-specific antibodies has progressed to also include bispecific antibodies that have the same overall structure as a normal mono-specific antibody but wherein the two arms of the antibody each bind a different target. The bispecific antibody or functional part, derivative and/or analogue thereof preferably has two heavy chains with compatible heterodimerization domains. The light chain is preferably a common light chain. The antibody is preferably a full length bispecific antibody that consists of two heavy chains with compatible heterodimerization domains. The light chain is preferably a common light chain.

As used herein, the term "conjugate" refers to two or more molecules that have been covalently joined, optionally by a linking region. For example, in some embodiments, a conjugate is a first protein or non-protein moiety joined to a second protein or non-protein moiety by a linking region. For example, in some embodiments of a binding molecule of the invention it comprises or consists of two or more antibodies that have been covalently joined. A conjugate is not limited to a first and second moiety but in some embodiments may also have a third, fourth or more moieties joined by further linking regions. As described elsewhere in this application, examples of protein moieties include, but are not limited to: a polypeptide, a peptidomimetic or an antibody (or antibody part, derivative, or analogue, as described elsewhere in the application). Examples of non-protein moieties include, but are not limited to aptamers. Numerous types of linker can be used, and the linker will be selected to be appropriate according to the molecule types in the conjugate and on the desired properties of the linker (length, flexibility, resistance to protease activity and other similar characteristics). Such linkers may comprise nucleotides, polypeptides, or a suitable synthetic material. For example, a linker may be a flexible peptide linker. In certain embodiments, the linker may be a cleavable linker, allowing the parts of the conjugate to be separated from each other. In other embodiments, a peptide linker might be a helical linker. Various examples and kits for linking proteins and other molecules are well known in the art. As used herein, the term "fusion protein" refers to a protein that comprises two or more polypeptides or proteins that have been joined at the DNA level by recombination and are expressed together as a single polypeptide. A fusion protein may also comprise a peptide linking region also encoded by the DNA and expressed together with the fusion protein. A peptide linker that is part of a fusion protein may be designed to have particular characteristics such as flexibility, hydrophilicity, protease-resistance, cleavability etc. All these properties can be designed within the DNA sequence and methods for designing linkers are well known in the art. For example, antibodies can be linked together by methods well-known in the art, and as described herein, to form bispecific or multi-targeting antibodies. Furthermore, bispecific antibodies can be constructed by various methods known in the art, for example, by using technology such as Biclonics® (see for instance WO2013/157954). A bispecific monoclonal antibody (BsMAb, BsAb) typically comprises binding domains of two different monoclonal antibodies and consequently binds to two different epitopes. Biclonics® molecules, but also other full length IgG bispecific antibodies have two different antigen binding specificities encoded by two different variable regions of a full length IgG molecule of a Fab of a scFv. Biclonics® can be produced by co-transfection of individual cells with genetic constructs encoding two different common light chain (cLC) antibodies as detailed elsewhere herein. CH3 engineering ensures efficient hetero-dimerization and formation of essentially pure bispecific antibodies.

An antibody of the present invention is preferably a bispecific antibody. Antibodies typically bind their target via the so-called antigen binding site. An unmodified antigen-binding site is typically formed by and present in a variable domain of the antibody. A variable domain contains the antigen-binding site. A variable domain that can bind an antigen is a variable domain comprising an antigen-binding site that can bind to an antigen.

An antibody variable domain typically comprises a heavy chain variable region (VH) and a light chain variable region (VL). The antigen-binding site can be present in the combined VH/VL variable domain, or in only the VH region or only the VL region. When the antigen-binding site is present in one of the two regions of the variable domain, the counterpart variable region can contribute to the folding and/or stability of the binding variable region, but does not significantly contribute to the binding of the antigen itself. As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

An antibody typically does not bind to other proteins than the specified target protein on the membrane of cells in a post-natal, preferably adult human.

A variable domain in an antibody or a functional part, derivative and/or analogue thereof of the invention that can bind an extracellular part of PD-1 binds to PD-1 and, under otherwise identical conditions, at least 100-fold lower to the extracellular part of another member of the CD28 family of the same species. A variable domain of an antibody or a functional part, derivative and/or analogue thereof that binds PD-1 binds to PD-1 and, under otherwise identical conditions, at least a 100-fold lower to the CD28, CTLA4, ICOS, BTLA, NKp30 and TMIGD2 of the same species. Considering that PD-1 is a cell surface protein, the binding is typically assessed on cells that express a member on a cell surface.

A variable domain in an antibody or a functional part, derivative and/or analogue thereof of the invention that can bind an extracellular part of LAG3 binds to LAG3 and, under otherwise identical conditions, at least 100-fold lower to the extracellular part of CD4 of the same species. Considering that LAG3 is a cell surface protein, the binding is typically assessed on cells that express a member on a cell surface.

The invention also provides a method for the treatment of an individual that has a cancer, the method comprising administering an antibody or a functional part, derivative and/or analogue of the invention or a bispecific antibody of the invention to the individual in need thereof. The individual is preferably an individual that has a cancer. In some embodiments, the cancer is a cancer that comprises cancer cells that express a membrane protein. In a preferred embodiment the cancer is a cancer that comprises cancer cells that express PD-L1 and/or PD-L2. The cancer is preferably an adenocarcinoma. Preferred cancers are colorectal cancer; pancreatic cancer; lung cancer; breast cancer; liver cancer; prostate cancer; ovarian cancer; cervical cancer; endometrial cancer; head and neck cancer; melanoma; testis cancer; urothelial cancer; renal cancer; stomach cancer; or carcinoid cancer. In a preferred embodiment the cancer is colorectal cancer; pancreatic cancer; lung cancer; breast cancer; liver cancer; prostate cancer; ovarian cancer; cervical cancer; endometrial cancer; head and neck cancer; or melanoma. In a particularly preferred embodiment the cancer is colorectal cancer; pancreatic cancer; lung cancer; breast cancer; or liver cancer. In a particularly preferred embodiment the cancer is a gastrointestinal cancer. In a preferred embodiment the cancer is colorectal cancer. In this embodiment the antibody or functional part, derivative and/or analogue thereof is preferably an antibody with a variable domain that can bind PD-1 and a variable domain that can bind LAG3. A PD-1 binding variable domain preferably blocks the binding of PD-1 to PD-L1 and/or PD-L2, preferably PD-L1. A LAG3 binding variable domain preferably blocks the binding of LAG3 to MHC class II. Preferably the method comprises two or more of said antibodies or functional parts thereof, as described for an Oligoclonics embodiment.

Further provided is a method for stimulating an immune response in an individual against an aberrant cell in said individual, the method comprising providing said individual with an antibody or a functional part, derivative and/or analogue thereof of the invention. The aberrant cell is preferably a cancer cell, a virus-infected cell, a parasite or a parasite infected cell. In a preferred embodiment the cell is a cancer cell or a neoplastic cell. In this embodiment the antibody or functional part, derivative and/or analogue thereof is preferably an antibody with a variable domain that can bind PD-1 and a variable domain that can bind LAG3. In this embodiment a PD-1 binding variable domain preferably blocks the binding of PD-1 to PD-L1 and/or PD-L2, preferably PD-L1. A LAG3 binding variable domain preferably blocks the binding of LAG3 to MHC class II. Preferably the method comprises two or more of said antibodies or functional parts thereof, as described for an Oligoclonics embodiment.

A neoplasm is an abnormal growth of tissue and when it also forms a mass is commonly referred to as a tumor. A neoplasm in the present invention typically forms a mass. A neoplastic cell is a cell from a neoplasm that has formed a mass. The World Health Organization (WHO) classifies neoplasms into four main groups: benign neoplasms, in situ neoplasms, malignant neoplasms, and neoplasms of uncertain or unknown behavior. Malignant neoplasms are also simply known as cancers.

Stimulating an immune response encompasses inducing an immune response and enhancing an already existing immune response. The immune response in an individual can be measured by measuring where applicable; the tumor load of the individual; the virus load of the individual; the parasite load of the individual.

Said virus-infected cell is preferably a cell infected with an immune-deficiency virus, a herpes virus, preferably a herpes simplex virus, a varicella-zostervirus, a cytomegalovirus or an Epstein-Barr virus, a papilloma virus, a hepatis virus, preferably a hepatitis A, B or C virus, a measles virus or an adenoviruses. The virus is preferably a virus known to be able to persist in an individual. Persistent infections are characterized as those in which the virus is not cleared but remains in specific cells of infected individuals. Persistent infections may involve stages of both silent and productive infection without rapidly killing or even producing excessive damage of the host cells. Persistent virus-host interaction may be a latent, a chronic and/or a slow infection.

A parasite-infected cell is a cell that is infected with an intracellular parasite. Such parasites are parasitic microorganisms that are capable of growing and reproducing inside the cells of a host. Some intracellular parasites can also live outside a cell. Such parasites are so-called facultative intracellular parasites. Non-limiting examples are *Listeria monocytogenes, Legionella*, certain species of *mycobacterium* and *Cryptococcus neoformans*. Preferred intracellular parasites are parasites that cannot grow outside host cells, preferred examples are *Chlamydia*, and closely related species, certain species of *mycobacterium* such as *Mycobacterium leprae*, certain protozoa, including: Apicomplexans (*Plasmodium* spp., *Toxoplasma gondii* and *Cryptosporidium parvum* and trypanosomatids.

The invention also provides a nucleic acid molecule that encodes an antibody heavy chain variable region according to the invention. The nucleic acid molecule (typically an in vitro, isolated or recombinant nucleic acid molecule) preferably encodes any one of the heavy chain variable regions as depicted in FIGS. 3A-3B or a heavy chain variable region as depicted in FIGS. 3A-3B having 1, 2, 3, 4 or 5 amino acid insertions, deletions, substitutions or combination thereof. In a preferred embodiment the nucleic acid molecule comprises a sequence as depicted in FIGS. 3A-3F. The nucleic acid molecule preferably uses codons that are optimized for expression in the antibody producing cell that is to be used. Preferably the nucleic acid encoding a heavy chain variable region as depicted in FIGS. 3A-3F or a heavy chain variable region as depicted in FIGS. 3A-3F having 1, 2, 3, 4 or 5 amino acid insertions, deletions, substitutions or combination thereof is codon optimized for expression in a human cell preferably Per.C6TM; or a Chinese hamster, preferably CHO. The invention further provides a nucleic acid molecule that codes for the mentioned heavy chain variable region together with a heavy chain constant region of FIG. 2.

A nucleic acid molecule as used in the invention is typically but not exclusively a ribonucleic acid (RNA) or a deoxyribonucleic acid (DNA). Alternative nucleic acids are available for a person skilled in the art. A nucleic acid molecule according to the invention is for instance comprised in a cell. When said nucleic acid molecule is expressed in said cell, said cell can produce an antibody according to the invention. Therefore, the invention in one embodiment provides a cell comprising an antibody according to the invention and/or a nucleic acid molecule according to the invention. An antibody is produced when said cell produces a heavy chain and a light chain. Provided is a cell that can produce an antibody of the invention. The cell preferably comprises a nucleic acid molecule that encodes an antibody heavy chain that comprises an antibody heavy chain variable region that, when combined with a common light chain, can bind said first membrane protein. Said cell preferably further comprises a nucleic acid molecule that encodes an antibody heavy chain that comprises an antibody heavy chain variable region that, when combined with a common light chain, can bind said second membrane protein. Said cell preferably further comprises a nucleic acid molecule that codes for a common light chain. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Also provided is a cell that comprises one or more nucleic acid molecules that alone or together encode an antibody of the invention. The one or more nucleic acid molecules are expressible nucleic acid molecules meaning that they contain the in cis required signals for RNA transcription and translation of protein coding domains. Preferably said cell (typically an in vitro, isolated or recombinant cell) produces said antibody. In a preferred embodiment said cell is a hybridoma cell, a Chinese hamster ovary (CHO) cell, an NS0 cell or a PER-C6TM cell. In a particularly preferred embodiment said cell is a CHO cell. Further provided is a cell culture that comprises a cell according to the invention. Various institutions and companies have developed cell lines for the large scale production of antibodies, for instance for clinical use. Non-limiting examples of such cell lines are CHO cells, NS0 cells or PER.C6TM cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIGS. 3, 1 and 2. Preferably said nucleic acid molecule comprises a sequence as depicted in FIGS. 1 and 2.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or any other cell type known in the art for its suitability for antibody production for clinical purposes, in particular for the production of antibodies used for administration in humans. In a particularly preferred embodiment said cell is a human cell, preferably a cell that is transformed by an adenovirus E1 region or a functional equivalent thereof. A preferred example of such a cell line is the PER.C6TM cell line or equivalent thereof. In a particularly preferred embodiment said cell is a CHO cell or a variant thereof, preferably a variant that makes use of a Glutamine synthetase (GS) vector system for expression of an antibody.

The invention further provides a pharmaceutical composition comprising one or more antibodies or variants thereof according to the invention. The pharmaceutical composition preferably comprises a preferably pharmaceutically acceptable excipient or carrier. An antibody or variant thereof of the invention may further comprise a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebr.).

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regimen of Nivolumab. The dosage can also be lower.

An antibody or variant thereof and in particular a bispecific antibody or a variant thereof according to the invention may have fewer side effects than a combination of bivalent monospecific antibodies with the variable domains. Combinations of antibodies that block inhibitory and/or costimulatory molecules benefit patients that do not respond to existing immunotherapies. However, dual blockade of immuno-modulatory receptors (iMODs) has been shown to increase immune-related toxicity. An antibody or variant thereof and in particular a bispecific antibody or a variant thereof according to the invention is suited to address dual blockade of iMODs, as they can exert functional activities that cannot be reproduced by monoclonal antibody combinations, and can more selectively target specific cell populations, which reduces safety liabilities in patients.

In view of the above, a bispecific antibody according to the present invention, or a functional part, derivative and/or analogue thereof, is preferred for therapeutic applications.

The antibodies were produced as bispecific antibodies by cloning them into complementary expression vectors that contain mutations in the CH3 region that drives heterodimerization of heavy chains. Many bispecific antibodies were produced at small scale and tested in binding and functional assays on cancer cell lines. An antibody of the invention, particularly a bispecific antibody of the invention can combine low toxicity profiles with high efficacy. An antibody of the invention can be useful in various types and lines of immune targeted therapies. An antibody of the invention can have an increased therapeutic window when compared to an antibody that binds the same antigen(s) with both arms.

Further provided is a use of a bispecific antibody according to the invention or a functional part, derivative and/or analogue thereof, for the preparation of a medicament for the treatment or prevention of aberrant cells, a tumor and/or the formation of metastases. The tumor from which said metastases originate is preferably a tumor that is positive for PD-L1 and/or PD-L2.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1.

For the purpose of clarity and a concise description features are described herein as part of the same or separate embodiments, however, it will be appreciated that the scope of the invention may include embodiments having combinations of all or some of the features described.

Also provided is a method for the treatment of an individual that has a cancer, the method comprising administering a protein of the invention or a bispecific antibody of the invention to the individual in need thereof.

The invention further provides a protein of the invention or a bispecific antibody of the invention, for use in the treatment of an individual that has cancer.

The antibody or variant thereof of the invention preferably comprises a variable domain that can bind to an extra cellular part of PD-1 and comprises a heavy chain variable region with a CDR3 region that comprises the amino acid sequence of the CDR3 of a variable heavy chain region of one of the VH depicted for MF6076; MF6226; MF6236; MF6256; MF6930; MF6932; MF6935; MF6936; MF6972; MF6974; or MF6982 in FIGS. 3A and 3B, preferably MF6256; MF6930; MF6076, MF6974 or MF6226, preferably MF6930, MF6076, or MF6974. Said variable domain that binds PD-1 preferably comprises a heavy chain variable region comprises a heavy chain variable region with a CDR1, CDR2 and CDR3 region that comprises the amino acid sequence of the CDR1, CDR2 and CDR3 of a variable heavy chain region of one of the VH depicted for MF6076; MF6226; MF6236; MF6256; MF6930; MF6932; MF6935; MF6936; MF6972; MF6974; or MF6982 in FIGS. 3A and 3B, preferably MF6256; MF6930; MF6076, MF6974 or MF6226, preferably MF6930, MF6076, or MF6974.

The antibody or variant thereof preferably comprises a variable domain that can bind to an extra cellular part of PD-1 and comprises a heavy chain variable region that comprises the amino acid sequence of the variable heavy chain region as depicted for MF6076; MF6226; MF6236; MF6256; MF6930; MF6932; MF6935; MF6936; MF6972; MF6974; or MF6982 FIGS. 3A and 3B, preferably MF6256; MF6930; MF6076, MF6974 or MF6226, preferably MF6930, MF6076 or MF6974 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the VH as depicted for MF.

The antibody or variant thereof preferably comprises a variable domain that can bind to an extra-cellular part of LAG3 and that comprises a heavy chain variable region with a CDR3 region that comprises the amino acid sequence of the CDR3 region of the variable heavy chain region as depicted for MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096. Said variable domain that binds LAG3 preferably comprises a heavy chain variable region comprises a heavy chain variable region with a CDR1, CDR2 and CDR3 region that comprises the amino acid sequence of the CDR1, CDR2 and CDR3 of a variable heavy chain region of one of the VH depicted for MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096.

The antibody or variant thereof preferably comprises a variable domain that can bind to an extra cellular part of LAG3 and comprises a heavy chain variable region that comprises the amino acid sequence of the variable heavy chain region as depicted for MF7100; MF7111; MF7116; MF7118; MF7134; MF7136; MF7137; MF7142; MF7146; MF7165; MF7167; MF7185; MF7443; MF7444; MF7515; MF7518; MF7096; MF7097; MF7106; MF7120; MF7133; MF7139; MF7144; or MF7524 of FIGS. 3C-3F, preferably MF7518; MF7165; MF7116; MF7096; MF7133; MF7139; MF7524 or MF7137, preferably MF7139; MF7524, MF7133, MF7518 or MF7096 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect the amino acid sequence of the indicated MF.

The invention is further explained in the following examples. These examples do not limit the scope of the invention, but merely serve to clarify the invention.

BRIEF DESCRIPTION OF THE DRAWINGS

FIG. 1. Common light chain used in mono- and bispecific IgG. FIG. 1A: Common light chain amino acid sequence.

FIG. 1: Common light chain variable domain DNA sequence and translation (IGKV1-39/jk1). FIG. 1C: Common light chain constant region DNA sequence and translation. FIG. 1D: IGKV1-39/jk5 common light chain variable domain translation. FIG. 1E: V-region IGKV1-39A FIG. 2. IgG heavy chains for the generation of bispecific molecules. FIG. 2A: VH gene. FIG. 2B: CH1 region. FIG. 2C: hinge region. FIG. 2D: CH2 region. FIG. 2E: CH2 region containing L235G and G236R silencing substitutions. FIG. 2F: CH3 domain containing substitutions L351K and T366K (KK). FIG. 2G; CH3 domain containing substitutions L351D and L368E (DE)

FIG. 2A VH: dependent on the MF (target): FIGS. 3A-3F.

FIG. 2B CH1:

FIG. 2C Hinge:

FIG. 2D CH2:

FIG. 2E CH2 containing L235G and G236R silencing substitutions:

FIG. 2F CH3: KK of DEKK

FIG. 2G CH3: DE of DEKK

FIGS. 3A-3F. Amino acid sequences of heavy chain variable regions:

FIG. 3A and 3B heavy chain variable regions of PD-1 specific clones

FIG. 3C-3F heavy chain variable regions of LAG-3 specific clones

The notation MF refers to a fab containing a heavy chain variable region as depicted and a common light chain. The amino acid sequence of the light chain is indicated in FIG. 1A. The underlined sequences indicate per amino acid sequence respectively the CDR1, the CDR2 and the CDR3 region.

Figure 4:
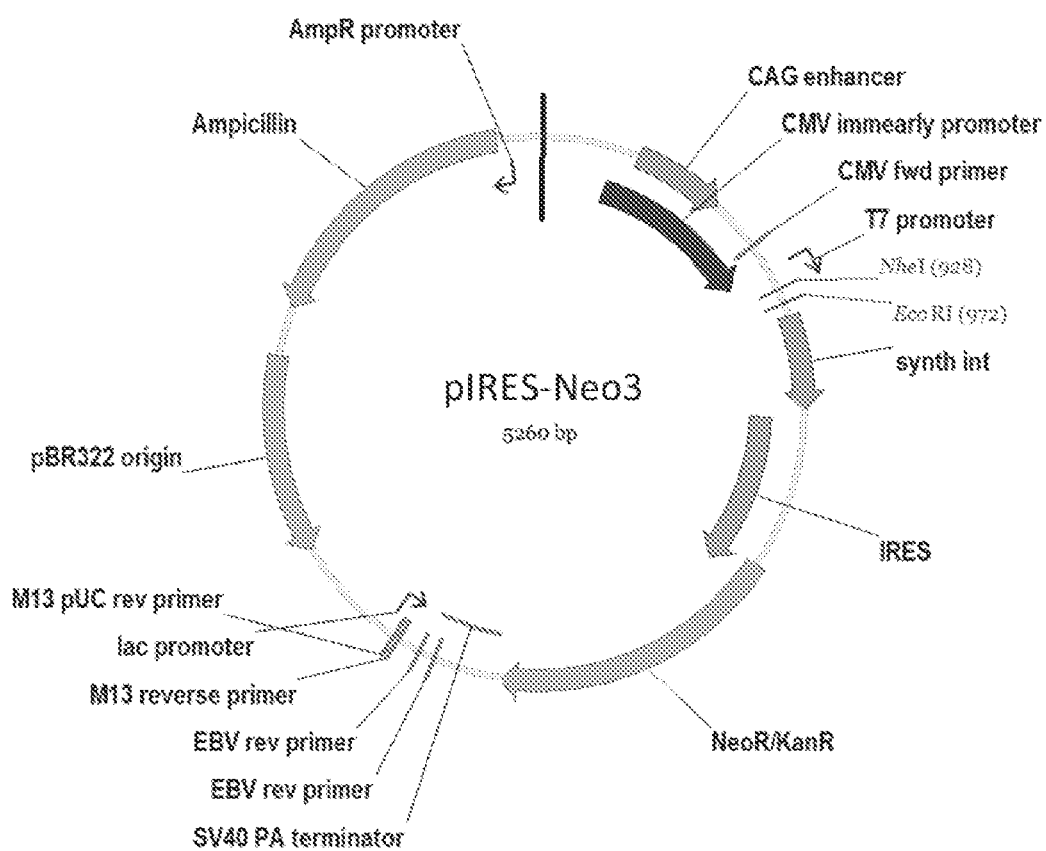

FIG. 4. Vector map and features of pIRES-Neo3 (MV1363).

Figure 5:
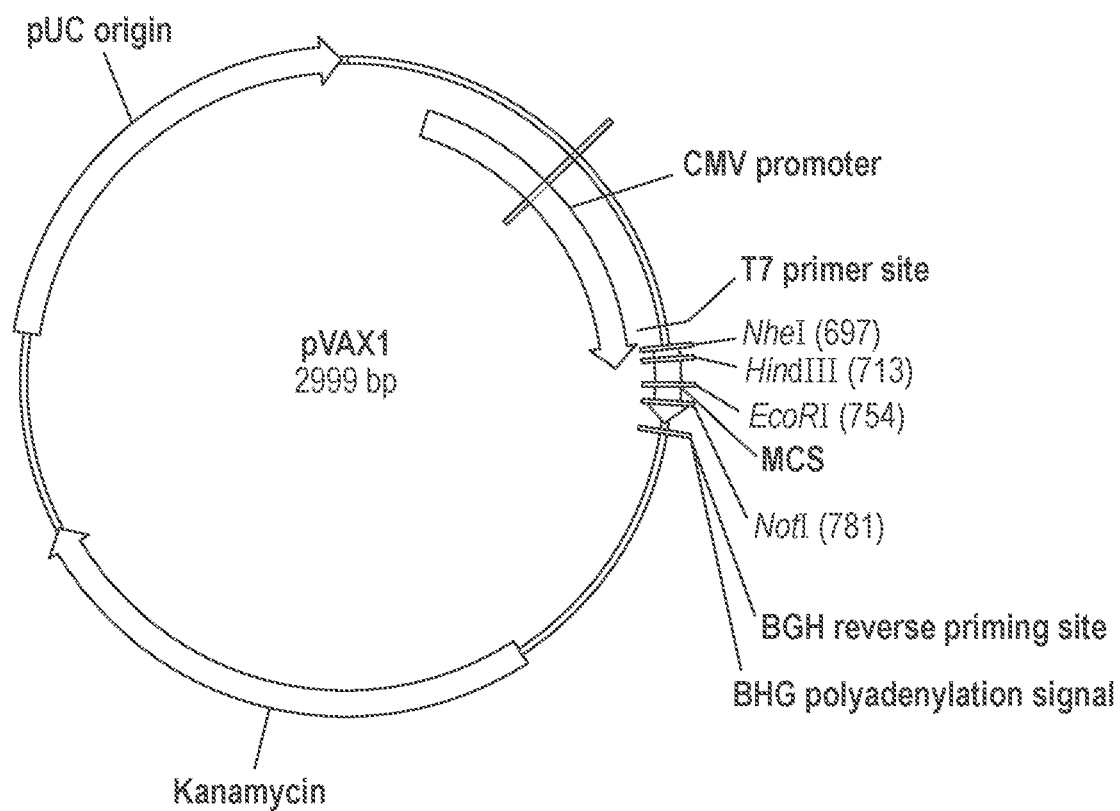

FIG. 5. Vector map and features of pVAX1.

Figure 6:
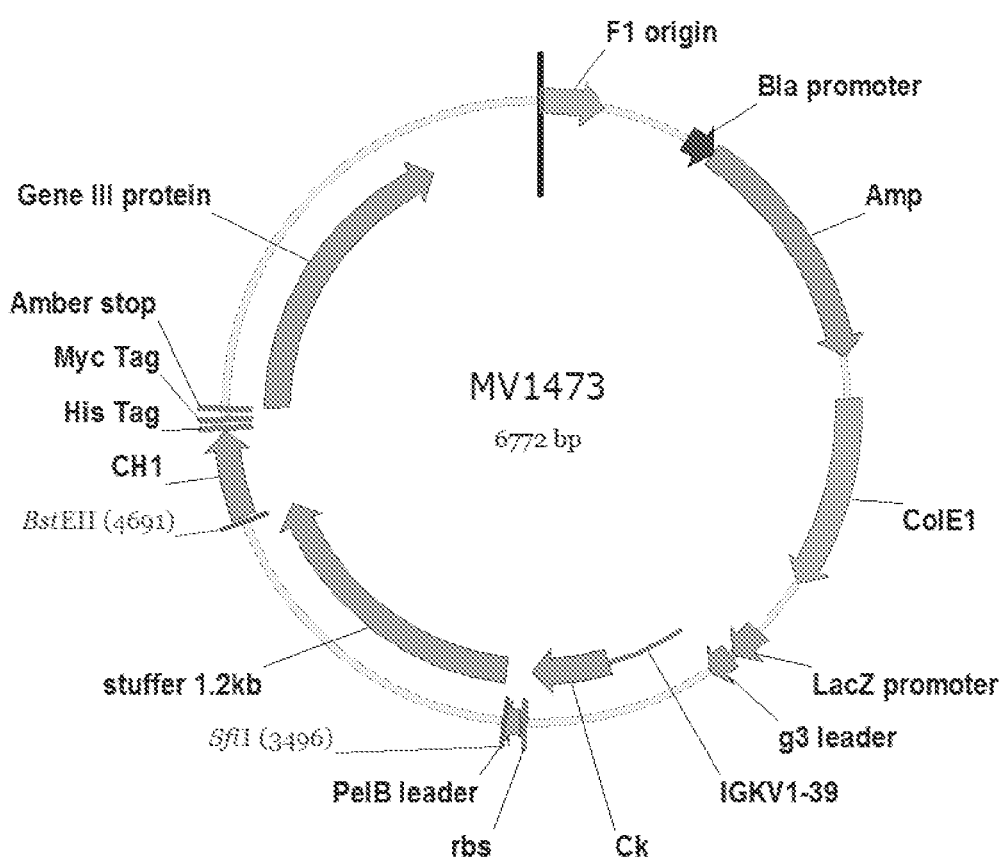

FIG. 6. Vector map and features of the phagemid vector MV1473 used to generate 'immune' phage display libraries.

Figure 7:
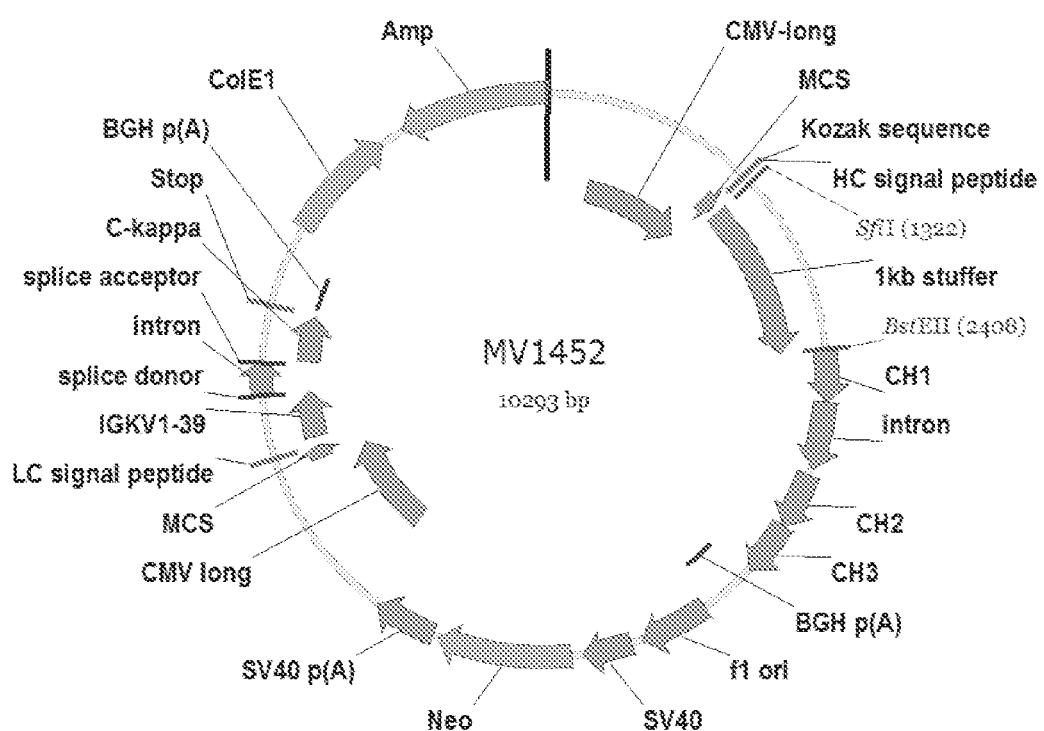

FIG. 7. Vector map and features of the IgG expression vector MV1452, that was used for expression of the PD-1 and PD-L1 specific Fab arms in the KK-variant heavy chain for bispecific IgG generation.

FIG. 8. Amino acid sequence of the VH gene that is tetanus toxin specific when combined with the common light chain as MF1337, and that is present in the DE-variant heavy chain that was used to generate PD-L1×TT and PD-1×TT bispecific IgG molecules. The underlined sequences indicate per amino acid sequence respectively the CDR1, the CDR2 and the CDR3 region.

Figure 9:
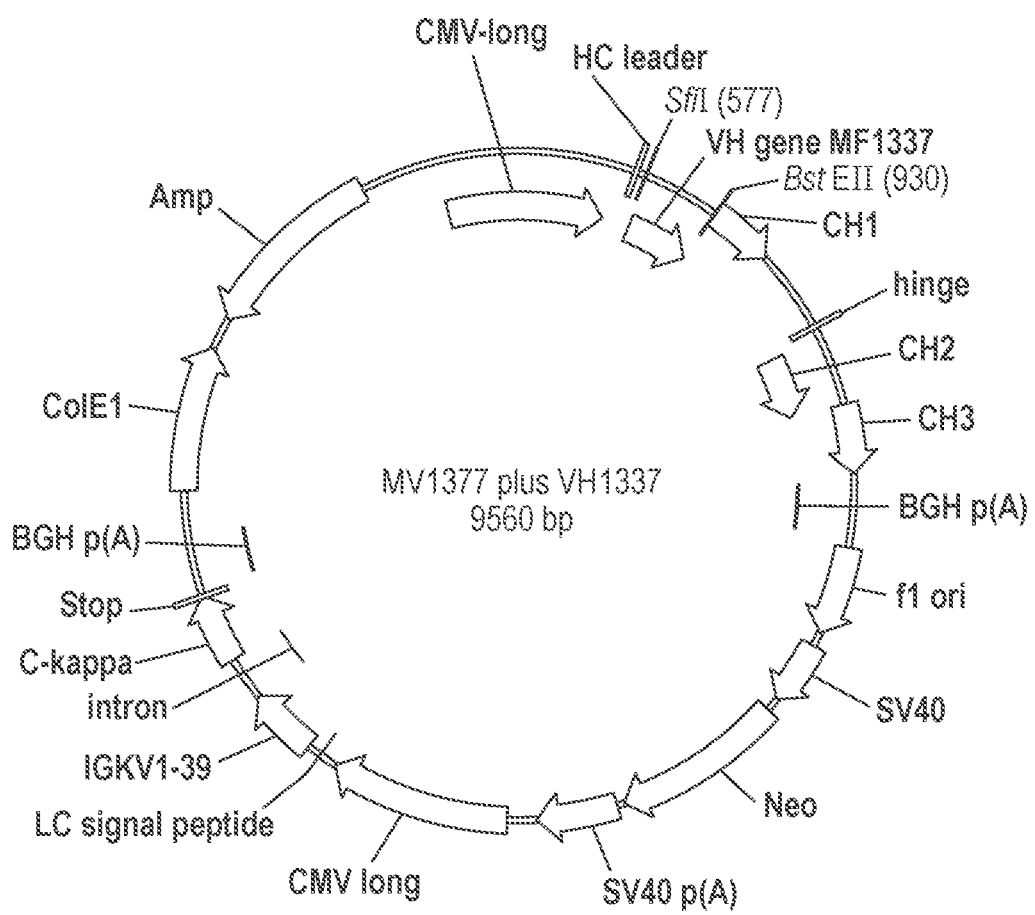

FIG. 9. Vector map and features of the IgG expression vector MV1377, that was used for expression of the TT specific Fab arm MF1337 in the DE-variant heavy chain for bispecific IgG generation.

Figure 10:
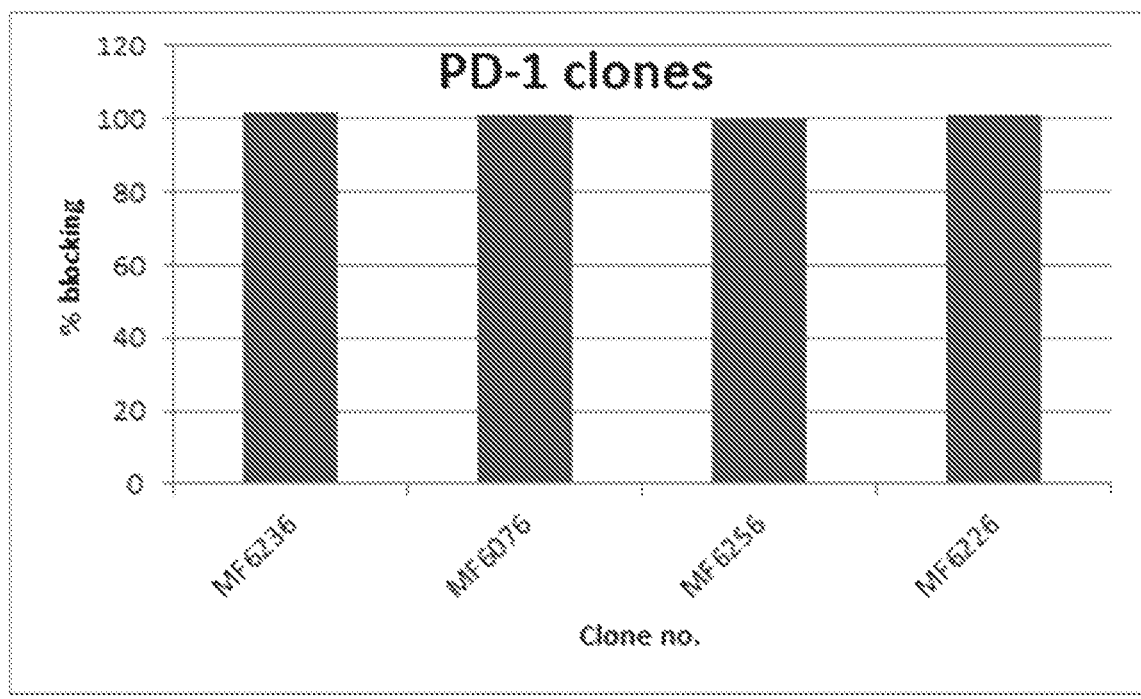

FIG. 10. PD-1/PD-L1 blocking assay

Assessment of the capacity of the anti-PD-1 antibody panel to block the interaction of PD-L1 to coated PD-1 at a concentration of 10 µg/ml bispecific IgG. Data are normalized to data obtained with the bivalent benchmark PD-L1 antibody MPDL3280A at a concentration of 10 µg/ml (100% blocking). A representative example is shown of the PD-1 panel. Maximum binding (normalized to 0% blocking) was established by incubation with a non-PD-1/PD-L1 specific human isotype antibody. All PD-1 variable domains comprising MF sequences depicted in FIGS. 3A-3F and not represented here block the PD-1/PD-L1 interaction >70%.

FIG. 11

LAG-3 functional activity of a panel of antibodies in a dose titration in the LAG-3 blockade reporter assay. The relation between domain mapping and LAG-3 blocking activity is shown in the LAG-3 is schematically drawn in the right panel.

FIG. 12

Stimulation index of IL-2 production of LAG-3×PD-1 antibodies in comparison to their parental bivalent LAG-3 antibody. Each IL-2 value is compared to the negative control antibody (not shown) to determine the SI.

FIG. 13

SEB-stimulation of IL-2 production in healthy donor blood cells is enhanced by anti-LAG-3×PD-1 bispecific antibodies in comparison to the parental PD-1 bivalent antibody and 25F7 LAG-3 reference antibody.

FIG. 14

Comparator anti-LAG-3 antibodies. PG1337P300 is a control antibody that is not expected to bind to the cells and binds tetanus toxoid.

Left hand panel shows binding of the indicated antibodies to 293FF-LAG-3 cells that express LAG-3 on the cell membrane. Right hand panel shows activated human T-cells. Binding of antibody to the cells was detected with PE-labelled anti-IgG F(ab')2. 25F7*, determined affinity ~0.2 nM.

FIG. 15

FACS-based LAG-3 panel characterization. Nineteen LAG-3 specific antibodies were expressed in monovalent (PB LAG-3×TT) and bivalent (PG) format. Antibody binding was tested on activated T cells and 293FF-LAG-3 stable cell lines. The two panels show an example of MF7116 and MF7431 (25F7*) mono- and bivalent binding on 293FF-LAG-3 cells. Monovalent binding was determined with a bispecific antibody (PB) where one arm has a VH (indicated by the letters MF) of the indicated LAG-3 antibody. The other arm of the antibody has a VH specific for tetanus toxoid (MF1337). Differences in binding were observed between some bivalent/monovalent formats of LAG-3 panel, but not of 25F7*.

FIG. 16

LAG-3×PD-1 reporter assay validation: bispecific antibodies show activity in LAG-3×PD-1 reporter assay.

FIG. 17

PD-1+LAG-3 reporter assay screening. Panel A, LAG-3×PD-1 with functional LAG-3 and PD-1 arms. Panel B, LAG-3×PD-1 with non-functional PD-1 arm with MF5374. Panel C, LAG-3×PD-1 with non-functional LAG-3 arms with MF7118 and MF7167. * indicates surrogate arms.

FIG. 18

Figure 18:
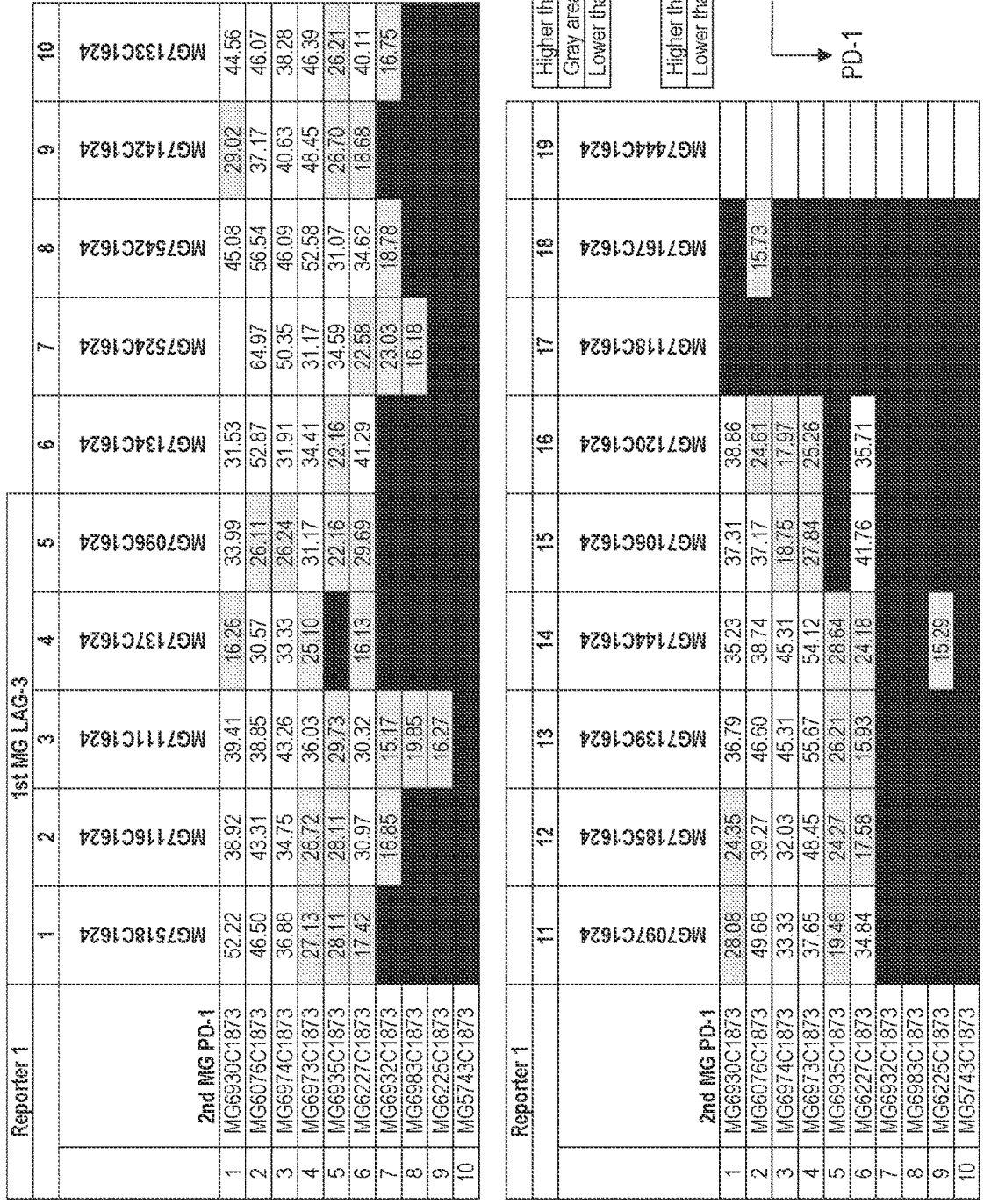

Summary of the results reporter assay screening set out in FIG. 18. The four digit number immediately following the letters MG indicates the MF number of the heavy chain variable region of the variable domain of the bispecific antibody. For example, the bispecific antibody with the result 52,22 in the upper left hand corner of the table has one arm with the MF6930 and one arm with MF7518. Values are area under the curve (AUC) as % of control.

FIG. 19

SEB assay screening: example IL-2 production. Panel A, LAG-3×PD-1 with functional PD-1 and LAG-3 arms. Panel B, LAG-3×PD-1 with non-functional PD-1 arm with VH MF5374. Panel C, LAG-3×PD-1 with non-functional LAG-3 arms with VH MF7118 and MF7167. * indicates a surrogate antibody.

FIGS. 20A-20C

Screening results reporter and SEB assays. Arms ranked on (high to low) functionality as bivalent antibodies in reporter assay. Top in each of the columns a LAG-3 arm, Left in each of the rows a PD-1 arm. As indicated for FIG.

19, the four digit number immediately following the letters MG indicates the MF number of the heavy chain variable region of the variable domain of the bispecific antibody. Values are AUC as % of control: White=Top 15%: Grey=Middle 43%: Black=Lowest 43%.

FIG. 21

Ranking LAG-3×PD-1; PD-1 arms. Matrix files were used to define the Top 15% of bispecific antibodies based on AUC as compared to positive control in: 1) Reporter assay; 2) SEB screening donor 1 (IL-2 data); 3) SEB screening donor 2 (IL-2 data). Next, it was scored how many bispecific antibodies carrying a specific PD-1 Fab arm were present in this top 15%. Clones with PD-1 arms having a variable domain with a VH of MF6974 or a VH of MF6076 performed best in combination with most of the LAG-3 arms in the reporter and SEB assays. Color/Grey coding, darker indicates higher rank.

FIG. 22

Ranking LAG-3×PD-1; LAG-3 arms. Matrix file was used to define the Top 15% (left) and top 25% (right) of Bispecifics based on AUC as compared to positive control in: 1) Reporter assay; 2) SEB screening donor 1 based on IL-2 data; 3) SEB screening donor 2 based on IL-2 data. Next, it was scored how many bispecific antibodies carrying a specific LAG-3 Fab arm were present in this top 15%. Fab arms with same score in Top 15% were further ranked by using Top 25% scores. Color/Grey coding, darker indicates higher rank.

FIG. 23

Ranking of PD1 arms. PD-1 arms (left hand column) based on ranking, sequence diversity and binding affinity.

FIG. 24

Ranking of LAG-3 arms. LAG-3 arms (left hand column) based on ranking, sequence diversity and binding affinity.

FIG. 25.

Effect of test antibodies on IFN-γ production in allogeneic mMLR.Mo-DCs were prepared from CD14+ monocytes cultured for 7 days. Immature DCs were used on day 7 and mature DCs were generated by culturing for a further 3 days in maturation medium before being cultured together with T cells isolated by negative selection and test antibody for 4 days (mMLR). IFN-y was measured in culture supernatants by ELISA. Data are normalized to vehicle control. Four separate MLRs were performed.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of FIG. 1A, typically 1B. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The variable region of the heavy chains differs and typically also the CH3 region, wherein one of the heavy chains has a KK mutation of its CH3 domain and the other has the complementing DE mutation of its CH3 domain (see for reference PCT/NL2013/050294 (published as WO2013/157954).

Example: 1

Generation of Materials for Selection and Screening
Culturing of Cell Lines

Freestyle 293F cells (cat. no. p/n51-0029) were obtained from Invitrogen and routinely maintained in 293 FreeStyle medium. HEK293T (cat. no. ATCC-CRL-11268) cells were purchased from ATCC and routinely maintained in DMEM/F12 (Gibco) supplemented with L-Glutamine (Gibco) and FBS (Lonza), and CHO-S (cat. no. 11619-012) cell lines were purchased from Gibco and routinely maintained in Freestyle CHO expression medium (Invitrogen) supplemented with L-glutamine.

Generation of PD-1 and LAG-3 Expression Vectors for Immunization, and for Generation of Stable Cell Lines and Transient Transfections Full length cDNA of each target including unique restriction sites for cloning and kozak consensus sequence for efficient translation was either synthetized, or obtained via PCR amplification on a commercially available expression construct, containing the target cDNA, with specific primers that introduced unique restriction sites for cloning and kozak consensus sequence for efficient translation. The cDNA of each target was cloned into a eukaryotic expression construct such as pIRES-Neo3 (Clontech; FIG. 4) or pVAX1 (Thermo Fisher Scientific; FIG. 5) via NheI/EcoRI, resulting in pIRES-Neo3_[TARGET_NAME] and pVAX1_[TARGET_NAME], respectively. The insert sequences were verified by comparison with NCBI Reference amino acid sequences. The pIRES-Neo3 constructs were used for generation of stable cell lines and transient transfections. The pVAX1 constructs were used for immunization purposes. See TABLE 1 for an overview of the names of the resulting constructs.

Amino acid sequence full length huPD-1 insert (both in pIRES-Neo3 and pVAX1) for expression on the cell surface (Identical to GenBank: NP_005009.2):

(SEQ ID NO: 1)
MQIPQAPWPVVWAVLQLGWRPGWFLDSPDRPWNPPTFSPALLVVTEG

DNATFTCSFSNTSESFVLNWYRMSPSNQTDKLAAFPEDRSQPGQDCR

FRVTQLPNGRDFHMSVVRARRNDSGTYLCGAISLAPKAQIKESLRAE

LRVTERRAEVPTAHPSPSPRPAGQFQTLVVGVVGGLLGSLVLLVWVL

AVICSRAARGTIGARRTGQPLKEDPSAVPVFSVDYGELDFQWREKTP

EPPVPCVPEQTEYATIVFPSGMGTSSPARRGSADGPRSAQPLRPEDG

HCSWPL

Of which:
(SEQ ID NO: 125)
MQIPQAPWPVVWAVLQLGWR:
signal peptide.

(SEQ ID NO: 126)
PGWFLDSPDRPWNPPTFSPALLVVTEGDNATFTCSFSNTSESFVLNW

YRMSPSNQTDKLAAFPEDRSQPGQDCRFRVTQLPNGRDFHMSVVRAR

RNDSGTYLCGAISLAPKAQIKESLRAELRVTERRAEVPTAHPSPSPR

PAGQFQTLV:
ECD of huPD-1.

(SEQ ID NO: 127)
VGVVGGLLGSLVLLVWVLAVI:
Predicted TM region.

(SEQ ID NO: 128)
CSRAARGTIGARRTGQPLKEDPSAVPVFSVDYGELDFQWREKTPEPP
VPCVPEQTEYATIVFPSGMGTSSPARRGSADGPRSAQPLRPEDGHCS
WPL:
Intracellular tail.

Amino acid sequence full length macaque (*Macaca fascicularis*) PD-1 insert (both in pIRES-Neo3 and pVAX1) for expression on the cell surface (Identical to GenBank: ABR15751.1):

(SEQ ID NO: 2)
MQIPQAPWPVVWAVLQLGWRPGWFLESPDRPWNAPTFSPALLLVTEG
DNATFTCSFSNASESFVLNWYRMSPSNQTDKLAAFPEDRSQPGQDCR
FRVTRLPNGRDFHMSVVRARRNDSGTYLCGAISLAPKAQIKESLRAE
LRVTERRAEVPTAHPSPSPRPAGQFQALVVGVVGGLLGSLVLLVWVL
AVICSRAAQGTIEARRTGQPLKEDPSAVPVFSVDYGELDFQWREKTP
EPPAPCVPEQTEYATIVFPSGLGTSSPARRGSADGPRSPRPLRPEDG
HCSWPL

Of which:
(SEQ ID NO: 125)
MQIPQAPWPVVWAVLQLGWR:
signal peptide.

(SEQ ID NO: 129)
PGWFLESPDRPWNAPTFSPALLLVTEGDNATFTCSFSNASESFVLNW
YRMSPSNQTDKLAAFPEDRSQPGQDCRFRVTRLPNGRDFHMSVVRAR
RNDSGTYLCGAISLAPKAQIKESLRAELRVTERRAEVPTAHPSPSPR
PAGQFQALV:
ECD of maPD-1.

(SEQ ID NO: 127)
VGVVGGLLGSLVLLVWVLAVI:
Predicted TM region.

(SEQ ID NO: 130)
CSRAAQGTIEARRTGQPLKEDPSAVPVFSVDYGELDFQWREKTPEPP
APCVPEQTEYATIVFPSGLGTSSPARRGSADGPRSPRPLRPEDGHCS
WPL:
Intracellular tail.

(SEQ ID NO: 3)
MWEAQFLGLLFLQPLWVAPVKPLQPGAEVPVVWAQEGAPAQLPCSPT
IPLQDLSLLRRAGYTWQHQPDSGPPAAAPGHPLAPGPHPAAPSSWGP
RPRRYTVLSVGPGGLRSGRLPLQPRVQLDERGRQRGDFSLWLRPARR
ADAGEYRAAVHLRDRALSCRLRLRGQASMTASPPGSLRASDWVILN
CSFSRPDRPASVHWFRNRGQGRVPVRESPHHHLAESFLFLPQVSPMD
SGPWGCILTYRDGFNVSIMYNLTVLGLEPPTPLTVYAGAGSRVGLPC

RLPAGVGTRSFLTAKWTPPGGGPDLLVTGDNGDFTLRLEDVSQAQAG
TYTCHIHLQEQQLNATVTLAIITVTPKSFGSPGSLGKLLCEVTPVSG
QERFVWSSLDTPSQRSFSGPWLEAQEAQLLSQPWQCQLYQGERLLGA
AVYFTELSSPGAQRSGRAPGALPAGHLLLFLILGVLSLLLLVTGAFG
FHLWRRQWRPRRFSALEQGIHPPQAQSKIEELEQEPEPEPEPEPEPE
PEPEPEQL

Of which:
(SEQ ID NO: 131)
MWEAQFLGLLFLQPLWVAPVKP:
signal peptide.

(SEQ ID NO: 132)
LQPGAEVPVVWAQEGAPAQLPCSPTIPLQDLSLLRRAGVTWQHQPDS
GPPAAAPGHPLAPGPHPAAPSSWGPRPRRYTVLSVGPGGLRSGRLPL
QPRVQLDERGRQRGDFSLWLRPARRADAGEYRAAVHLRDRALSCRLR
LRLGQASMTASPPGSLRASDWVILNCSFSRPDRPASVHWFRNRGQGR
VPVRESPHHHLAESFLFLPQVSPMDSGPWGCILTYRDGFNVSIMYNL
TVLGLEPPTPLTVYAGAGSRVGLPCRLPAGVGTRSFLTAKWTPPGGG
PDLLVTGDNGDFTLRLEDVSQAQAGTYTCHIHLQEQQLNATVTLAII
TVTPKSFGSPGSLGKLLCEVTPVSGQERFVWSSLDTPSQRSFSGPWL
EAQEAQLLSQPWQCQLYQGERLLGAAVYFTELSSTGAQRSGRAPGAL
PAGHL:
ECD.

(SEQ ID NO: 133)
LLFLILGVLSLLLLVTGAFGF:
Predicted TM region.

(SEQ ID NO: 134)
HLWRRQWRPRRFSALEQGIHPPQAQSKIEELEQEPEPEPEPEPEPEP
EPEPEQL:
Intracellular tail.

Amino acid sequence full length rat (*Rattus norvegicus*) LAG-3 insert (both in pIRES-Neo3 and pVAX1) for expression on the cell surface (Identical to GenBank: NP_997678.2):

(SEQ ID NO: 4)
MRQDLFLDLLLLQLLWEAPVVSSGPGKELSVVWAQEGAPVHLPCSLE
FPHLDPNFLRRGWVTWQHRPDSDQPASIPALDLLQGMPSTRRHPPHR
YTVLSVAPGGLRSGRQPLLSHVQLEKRGPQRGDFSLWLRPATRKDAG
EYHAFVRLPDRDFSCSLRLRVGQASMIASPPGTLKPSDWVILNCSFS
RPDRPVSVHWFQGQSRVPVHNSPRHYLAESFLLLPQVSPLDSGTWGC
VLTYRDGFNVSITYNLKVQGLEPVAPLTVYAAEGSRVELPCHLPPVV
GTPSLLIAKWTPPGGGPELPVTGKSGNFTLQLENVGRAQAGTYTCSI
HLQGRQLSAAVTLAVITVTPKSFGLPGSPQKLLCEVVPASGEGRFVW
RPLSDLSRSSLGPVLELQEAKLLAEQWQCQLYEGQKLLGATVYTAES
SSGAWSAKRISGDLKGGHLFLSLILGALALFLLVTGAFGFHLWRRQL

-continued

LRRRFSALEHGIRPPPVQSKIEELEREPETEMEPETEPDPEPQPEPE

LEPESRQL

Of which:

(SEQ ID NO: 135)
MRQDLFLDLLLLQLLWEAPVVSS:
signal peptide.

(SEQ ID NO: 136)
GPGKELSVVWAQEGAPVHLPCSLEFPHLDPNFLRRGWVTWQHRPDSD

QPASIPALDLLQGMPSTRRHPPHRYTVLSVAPGGLRSGRQPLLSHVQ

LEKRGPQRGDFSLWLRPATRKDAGEYHAFVRLPDRDFSCSLRLRVGQ

ASMIASPPGTLKPSDWVILNCSFSRPDRPVSVHWFQGQSRVPVHNSP

RHYLAESFLLLPQVSPLDSGTWGCVLTYRDGFNVSITYNLKVQGLEP

VAPLTVYAAEGSRVELPCHLPPVVGTPSLLIAKWTPPGGGPELPVTG

KSGNFTLQLENVGRAQAGTYTCSIHLQGRQLSAAVTLAVITVTPKSF

GLPGSPQKLLCEVVPASGEGRFVWRPLSDLSRSSLGPVLELQEAKLL

AEQWQCQLYEGQKLLGATVYTAESSSGAWSAKRISGDLKGGHL:
ECD.

(SEQ ID NO: 137)
FLSLILGALALFLLVTGAFGF:
Predicted TM region.

(SEQ ID NO: 138)
HLWRRQLLRRRFSALEHGIRPPPVQSKIEELEREPETEMEPETEDP

EPQPEPELEPESRQL:
Intracellular tail.

Amino acid sequence full length macaque (*Macaca mulatta*) LAG-3 insert (both in pIRES-Neo3 and pVAX1) for expression on the cell surface (Identical to GenBank: *Macaca mulatta*):

(SEQ ID NO: 5)
MWEAQFLGLLFLQPLWVAPVKPPQPGAEISVVWAQEGAPAQLPCSPT

IPLQDLSLLRRAGVTWQHQPDSGPPAPAPGHPPAPGHRPAAPYSWGP

RPRRYTVLSVGPGGLRSGRLPLQPRVQLDERGRQRGDFSLWLRPARR

ADAGEYRATVHLRDRALSCRLRLRVGQASMTASPPGSLRTSDWVILN

CSFSRPDRPASVHWFRSRGQGRVPVQGSPHHHLAESFLFLPHVGPMD

SGLWGCILTYRDGFNVSIMYNLTVLGLEPATPLTVYAGAGSRVELPC

RLPPAVGTQSFLTAKWAPPGGGPDLLVAGDNGDFTLRLEDVSQAQAG

TYICHIRLQGQQLNATVTLAIITVTPKSFGSPGSLGKLLCEVTPASG

QEHFVWSPLNTPSQRSFSGPWLEAQEAQLLSQPWQCQLHQGETLLGA

AVYFTELSSPGAQRSGRAPGALRAGHLPLFLILGVLFLLLLVTGAFG

FHLWRRQWRPRRFSALEQGIHPPQAQSKIEELEQEPELEPEPELERE

LGPEPEPGPEPEPEQL

Of which:

(SEQ ID NO: 131)
MWEAQFLGLLFLQPLWVAPVKP:
signal peptide.

(SEQ ID NO: 139)
PQPGAEISVVWAQEGAPAQLPCSPTIPLQDLSLLRRAGVTWQHQPDS

GPPAPAPGHPPAPGHRPAAPYSWGPRPRRYTVLSVGPGGLRSGRLPL

QPRVQLDERGRQRGDFSLWLRPARRADAGEYRATVHLRDRALSCRLR

LRVGQASMTASPPGSLRTSDWVILNCSFSRPDRPASVHWFRSRGQGR

VPVQGSPHHHLAESFLFLPHVGPMDSGLWGCILTYRDGFNVSIMYNL

TVLGLEPATPLTVYAGAGSRVELPCRLPPAVGTQSFLTAKWAPPGGG

PDLLVAGDNGDFTLRLEDVSQAQAGTYICHIRLQGQQLNATVTLAII

TVTPKSFGSPGSLGKLLCEVTPASGQEHFVWSPLNTPSQRSFSGPWL

EAQEAQLLSQPWQCQLHQGETLLGAAVYFTELSSPGAQRSGRAPGAL

RAGHL:
ECD.

(SEQ ID NO: 140)
PLFLILGVLFLLLLVTGAFGF:
Predicted TM region.

(SEQ ID NO: 141)
HLWRRQWRPRRFSALEQGIHPPQAQSKIEELEQEPELEPEPELEREL

GPEPEPGPEPEPEQL:
Intracellular tail.

Generation of Stable Cell Lines Expressing PD-1 or LAG-3 pIRES-Neo3_[TARGET_NAME] expression constructs (TABLE 1) were used to generate CHO-S or Freestyle 293F clones stably expressing the respective proteins. Constructs were transiently transfected in CHO-S and Freestyle 293F cells using lipofectamine transfection, and screened by FACS using antibodies reacting with the respective proteins. After confirmation of expression, transiently transfected cells were seeded in limiting dilution and cultured under selection pressure relevant for the used expression construct to obtain stable cell clones. After 2-3 weeks of selection, clones were screened by FACS. The selected clones were expanded by serial passage, retested in FACS and frozen to −150° C. The names of clones that stably express the heterologous proteins are CHO-S_[TARGET_NAME] cells or Freestyle 293F_[TARGET_NAME] cells. See TABLE 1 for an overview of the constructs used to generate the stable cell lines and their resulting name.

Example 2

Immunization, Selection and Screening
Mice Used for Immunizations

For generation of human antibodies binding to huPD-1 and huLAG-3, mice transgenic for the human VK1-39 light chain (common light chain mice, see WO2009/157771) and for a human heavy chain (HG) minilocus (comprising a selection of human V gene segments, all human Ds and all human Js) were immunized. These mice are referred to as 'MeMo®' mice. Mice were immunized with either recombinant protein antigen, or DNA encoding the protein antigen as briefly described below.
Protein Immunizations 'MeMo®' mice were immunized by subcutaneous injections with recombinant protein and Gerbu adjuvant MM (Gerbu Biotechnik; cat. no. 3001). Recombinant huPD-1-Fc (R&D; cat. no. 1086-PD) and huLAG-3-His (Abcam; cat. no. Ab184729) were used for immunizations. Mice were immunized with 40 μg recombinant protein in PBS mixed with 40 μl of adjuvant in a total volume of 100 μl. Subsequently mice were boosted on day 14 and 28 with 20 μg of recombinant protein in PBS together with 20 μl of adjuvant in a total volume of 50 μl. Mouse serum was collected at day 35 to determine serum titers. Mice with low serum reactivity against the human and/or macaque target received additional cycles of booster immunizations with recombinant human or macaque protein antigen and serum analyses. Each cycle consisted of two weekly immunizations using to 20 µg of recombinant protein in 50 µl PBS followed one week later by serum collection for titer analysis. Mice showing high serum titers against the human and macaque target received a final boost immunization consisting of daily injections with 20 µg of recombinant protein in 50 µl PBS on three consecutive days. One day after the final injection mouse lymphoid tissue was collected.

DNA Immunizations

MeMo®' mice were immunized by DNA tattooing using a micropigmentation device. DNA tattoo immunizations were performed with 20 µg plasmid DNA encoding the target antigen (pVAX1_[TARGET_NAME], TABLE 1). Mice were immunized with DNA encoding the human target only (PD-1 and LAG-3) or by alternating immunizations with DNA encoding the human and rat (LAG-3) target to obtain species cross-reactive antibodies. Mice were immunized at day 0, 3, 6, 14, 17, 28 and 31. Mouse serum was collected at day 35 to determine serum titers. Mice with low serum reactivity against the human and/or macaque target received additional cycles of booster immunizations with human DNA antigen, and serum analyses. Each cycle consisted of two weekly DNA immunizations followed one week later by serum collection for titer analysis. Mice showing strong serum reactivity against cells expressing the human and macaque target received a final boost immunization followed after 3 days by collection of lymphoid tissue.

Determination of Serum Titers

Serum titers were determined by FACS analysis using cell lines expressing the human and macaque target antigens.

Generation of Synthetic Phage Fab Libraries

Synthetic libraries were constructed based on a repertoire of germline human VH genes that were selected for frequent use in natural repertoires and canonical sequence diversity. Synthetic HCDR3 regions were added to these VH genes using PCR. This was done using forward primers that anneal to framework 1 of the VH genes and include a SfI restriction site for cloning. Reverse primers included sequences to anneal to framework 3 of the VH genes, followed by randomized sequences to encode HCDR3 diversity and a framework 4 encoding sequence also containing a BstEII and XhoI restriction site for cloning. Synthetic CDR3 regions were either completely random or encoded a more restricted diversity based on the frequency of use of amino acid residues at certain positions within the HCDR3. PCR products encoding the VH genes were cloned into phage display vectors in fusion with phage M13 gene 3 protein using aforementioned restriction enzymes and also containing a common light chain encoding gene. Large scale ligation and transformation of E'coli TG1 resulted in large libraries of synthetic Fab fragments displayed on phage which were used for panning on antigens or cells to identify antigen-specific Fab fragments.

Generation of 'Immune' Phage Fab Libraries by RT-PCR from Tissues of Immunized Mice Spleen and draining lymph nodes were removed from mice for which a significant humoral response was observed against the respective target proteins. Single cell suspensions were generated from both spleen and inguinal lymph nodes and subsequently these tissues were lysed in Trizol LS Reagent (Thermo Scientific c #10296028) and stored at −80° C. until use.

From successfully immunized mice, the inguinal lymph nodes were used for the construction of 'immune' phage antibody repertoires. RNA was extracted from the single cell suspensions of the lymphoid tissue. 1 µg of total RNA was used in a RT reaction using an IgG-CH1 specific primer. The resulting cDNA was then used to amplify the polyclonal pool of VH-encoding cDNA using in-house adapted VH-specific primers essentially as described in Marks et al. (J Mol Biol. 1991 Dec. 5; 222(3):581-97). The resulting PCR product was then cloned in a phagemid vector (FIG. 6) for the display of Fab fragments on phage, as described in de Haard et al. (J Biol Chem. 1999 Jun. 25; 274(26):18218-30) with the exception that the light chain (FIGS. 1A and 1B) was the same for every antibody and was encoded by the vector. After ligation, the phagemids were used to transform E. coli TG1 bacteria and transformed bacteria were plated onto LB-agar plates containing ampicillin and glucose. All phage libraries contained >4×10$^5$ transformants and had an insert frequency of >90%. Bacteria were harvested after overnight growth and used to prepare phage according to established protocols (de Haard et al., J Biol Chem. 1999 Jun. 25; 274(26):18218-30).

Selection of Phage Carrying Fab Fragments Specifically Binding to Human Target Protein from Synthetic and 'Immune' Phage Fab Libraries Using Recombinant Proteins The phage Fab libraries that were generated were used to select target specific Fabs using phage display on directly coated recombinant proteins. For PD-1, huPD-1-Fc (R&D; cat. no. 1086-PD) and huPD-1 biotin (BPS bioscience; cat. no. 71109) were used. For LAG-3, huLAG-3-Fc (R&D; cat. no. 2319-L3), huLAG-3-Fc (Enzo; cat. no. ALX-522-078), huLAG-3-His (Abcam; cat. no. Ab184729) and ratLAG-3 His (SinoBiological; cat. no. 80367-R08H) were used.

For selections with non-biotinylated recombinant protein ('panning selections'), proteins were coated onto the wells of a MAXISORP™ ELISA plate. The MAXISORP™ ELISA plates were blocked with 4% dried skimmed milk (Marvel) in PBS. Phage Fab libraries were also blocked with 4% Marvel and, when Fc tagged recombinant protein was used, also with excess of human IgG to deplete for Fc region binders prior to the addition of the phage library to the coated antigen.

Incubation of the phage library with the coated protein was performed for 1.5 hrs at room temperature under shaking conditions. Plates or tubes were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

For selections with biotinylated protein ('in-solution selections'), neutravidin was coated onto the well of a MAXISORP™ ELISA plate. The MAXISORP™ ELISA plates were blocked with 1% casein in PBS. In parallel, biotinylated protein and phage Fab libraries were blocked for 30 minutes in 0.5% casein in PBS, containing an excess of human IgG, in separate Eppendorf tubes. Thereafter, the blocked phage and biotinylated protein were mixed and incubated for 2 hours at room temperature. The mixture was thereafter added to the neutravidin coated wells for 20 minutes to capture the phage Fab particles that were bound to biotinylated protein. Plates were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

The eluates of both selection strategies ('panning and in-solution') were added to E. coli TG-1 and incubated at 37° C. for phage infection. Subsequently infected bacteria were plated on agar plates containing Ampicillin and glucose, and incubated at 37° C. overnight. Single clones from the selection outputs were screened for target binding in ELISA or FACS depending on the target.

For selections with synthetic phage Fab libraries, a second round selection was performed after rescue of the first round selection output using the same protocol as outlined above for the first round selection. The same selection antigen that was used in the first round was also used in the second round, with exception of first round raLAG-3-His selections that were followed by a second round selection with huLAG-3-His.

Selection of Phage Carrying Fab Fragments Specifically Binding to Human Target from 'Immune' Phage Fab Libraries Using Cells Stably Expressing the Target Protein Phage Fab libraries that were generated from target immunized mice were selected using phage display on cells expressing the respective target. The stable cell lines expressing PD-1 or LAG-3 (Table 1) were used for $1^{st}$ round selections. Cells were blocked with 10% FBS in PBS. After blocking, the rescued phage were incubated with blocked cells. Cells plus phage were incubated for 1 hr at 4° C. Washing the cells (5 times) was performed using 1 ml of 10% FBS in PBS. Bound phage were eluted using trypsin for 20 minutes, after which trypsin was neutralized with AEBSF trypsin inhibitor (Sigma). The eluate was added to E. coli TG-1 and incubated at 37° C. for phage infection. Subsequently, phage-infected bacteria were plated on agar plates containing ampicillin and glucose, and incubated at 37° C. overnight.

Screening for Target Specific Fab Clones in ELISA

Of single clones, soluble Fab or phage were prepared (J Mol Biol. 1991 Dec. 5; 222(3):581-97; J Biol Chem. 1999 Jun. 25; 274(26):18218-30). Obtained soluble Fab or phage samples were diluted (1:5 or 1:10, respectively) in 4% dried skimmed milk (Marvel) in PBS (blockbuffer) and tested for binding in ELISA to wells coated with the same antigen as was used for selection, or with huLAG-3-His (Abcam; cat. no. Ab184729) for all selection outputs performed with ratLAG-3 His (SinoBiological; cat. no. 80367-R08H).

Bound Fabs were detected by staining with an anti-myc antibody (Roche; cat. no. 11667203001) diluted 1:1000 in blockbuffer, followed by a HRP-conjugated anti-mouse IgG antibody (Jackson Immunoresearch; cat. no. 715-035-150) diluted 1:5000 in blockbuffer. Bound phage were detected by staining with a HRP-conjugated monoclonal anti-M13 antibody (GE healthcare; cat. no. 27-9421-01) diluted 1:5000 in blockbuffer.

After each antibody staining, wells were washed with PBS-T (PBS-0.05% v/v Tween 20). Bound secondary antibody was visualized by TMB/$H_2O_2$ staining and staining was quantified by means of $OD_{450\ nm}$ measurement. Clones were considered to bind the target when the OD450 nm was at least three times above the background signal obtained with a negative control Fab.

The VH-encoding cDNA's of all target-specific clones were sequenced. A selection of unique clones based on sequence identity and cluster analysis was then analyzed in FACS on binding to PD-L1 expressed on cells as described below for the clones obtained from the cell selection outputs.

Screening for Target Specific Fab Clones in FACS

Of single clones, selected on cells expressing the respective target, soluble Fab or phage were prepared as described (J Mol Biol. 1991 Dec. 5; 222(3):581-97; J Biol Chem. 1999 Jun. 25; 274(26):18218-30). Fab samples were tested for binding in FACS to cells expressing the human and macaque target (Table 1) by incubation with a mix of 1:5 diluted Fab sample with 1:1000 diluted anti-myc antibody (Gentaur; cat. no. 04-CMYC-9E10) in FACS buffer (0.5% HI-FBS in PBS). Bound Fab/anti-myc complexes were detected by incubation with an APC-conjugated goat anti-mouse IgG antibody (BD Bioscience; cat. no. 550826) diluted 1:500 in FACS buffer.

Phage samples were tested for binding in FACS by diluting the phage samples 1:3 in blockbuffer and incubation with target expressing cells for 1 hour. Bound phage were detected by staining with a biotinylated anti-M13 antibody (Fitzgerald, cat. nr. 61R-M101ABTB62-FEZ, 1:125 in FACS buffer, 30 minutes on ice) and PE-labeled streptavidin (Invitrogen, cat. nr. SA1004-4; 1:400 in FACS buffer for 15 minutes on ice). After each antibody incubation, wells were washed three times with FACS buffer. Stained cells were analysed using a FACS Accuri C6 instrument (Becton and Dickinson). Clones were considered positive when the mean fluorescence intensity was at least three times above the background signal obtained with a negative control Fab.

Example 3

Characterization huLAG-3 and huPD-1 Specific Fab Clones in IgG Format

Recloning Human LAG-3 and PD-1 Specific Fab to IgG Format

A selection of unique clones, based on CDR3 sequence and VH germline differences, that bound human and macaque target protein expressed on cells, was then re-cloned to an IgG expression plasmid such as MV1452 (FIG. 7), which contained the common light chain (FIG. 1), using Sfi1-BstEII digestion and ligation of the pool of digested cDNA's according to standardized molecular biological techniques.

Expression of Bispecific IgG Containing a Human LAG-3 or Human PD-1 Specific Fab and a Tetanus Toxin Specific Fab Bispecific antibodies were generated by transient co-transfection of two plasmids encoding IgG with different VH domains, using a proprietary CH3 engineering technology to ensure efficient hetero-dimerisation and formation of bispecific antibodies. The common light chain present on both plasmids containing the heavy chain is also co-transfected in the same cell. In our co-pending applications (e.g. WO2013/157954 and WO2013/157953; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa (FIG. 2). It was previously demonstrated in our co-pending applications that the negatively charged DE-variant heavy chain and positively charged KK-variant heavy chain preferentially pair to form heterodimers (so-called 'DEKK' bispecific molecules). Homodimerization of DE-variant heavy chains (DE-DE homodimers) or KK-variant heavy chains (KK-KK homodimers) hardly occurs due to strong repulsion between the charged residues in the CH3-CH3 interface between identical heavy chains.

VH genes encoding the antibodies binding human LAG-3 and PD-1 described above were cloned into the MV1452 IgG expression vector encoding the positively charged CH3 domain. A tetanus toxin (TT) targeting antibody (FIG. 8) was cloned into the MV1377 IgG expression vector (FIG. 9) encoding the negatively charged CH3 domain. For expression of the LAG-3 and PD-1 antibody panel in IgG format, the entire panel was also cloned into the negatively charged CH3 domain vector to be able to produce bivalent LAG-3 or PD-1 IgG. Suspension growth-adapted 293F Freestyle cells were cultivated in T125 flasks on a shaker plateau until a density of $3.0 \times 10^6$ cells/ml. Cells were seeded at a density of $0.3-0.5 \times 10^6$ viable cells/ml in each well of a 24-deep well plate. The cells were transiently transfected with a mix of two plasmids encoding different antibodies, cloned into the proprietary vector system. Seven days after transfection, the cellular supernatant was harvested and filtered through a 0.22 μM filter (Sartorius). The sterile supernatant was stored at 4° C. until purification of the antibodies.

Purification of Bispecific IgG

Purification of IgG was performed on a small scale (<500 μg), using protein-A affinity chromatography. Small scale purifications were performed under sterile conditions in 24 well filter plates using filtration. First, the pH of the medium was adjusted to pH 8.0 and subsequently, IgG-containing supernatants were incubated with protein A Sepharose CL-4B beads (50% v/v) (Pierce) for 2 hrs at 25° C. on a shaking platform at 600 rpm. Next, the beads were harvested by filtration. Beads were washed twice with PBS pH 7.4. Bound IgG was then eluted at pH 3.0 with 0.1 M citrate buffer and the eluate was immediately neutralized using Tris pH 8.0. Buffer exchange was performed by centrifugation using multiscreen Ultracel 10 multiplates (Millipore). The samples were finally harvested in PBS pH7.4. The IgG concentration was measured using Octet. Protein samples were stored at 4° C.

IgG Quantification Using Octet

To determine the amount of IgG purified, the concentration of antibody was determined by means of Octet analysis using protein-A biosensors (Forte-Bio, according to the supplier's recommendations) using total human IgG (Sigma Aldrich, cat. nr. 14506) as standard.

Specificity Analysis huLAG-3 and huPD-1 IgG

The antibodies (bivalent LAG-3 antibodies and bispecific PD-1×TT antibodies) were tested for binding in FACS to the stable cell lines expressing the relevant human and macaque orthologs (Table 1) and the wt cells. Therefore, cells were harvested and diluted to $10^6$ cells/ml in FACS buffer (PBS/0.5% BSA/0.5 mM EDTA). $1-2 \times 10^5$ cells were added to each well in a U-bottom 96 well plate. Cells were centrifuged for 2 minutes at 300 g at 4° C. Supernatant was discarded by inverting the plate(s). 50 μl of each IgG sample at a concentration of 10 μg/ml was added and incubated for 1H on ice. Cells were centrifuged once, supernatant was removed and cells were washed twice with 150 μl of FACS buffer. 50 μl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Binning huPD-1 Specific Fab Arms Present in the PD-1×TT Bispecific IgG on Ligand Blocking Ability huPD-1 binding clones were tested for their ability to block the interaction of PD-L1 with PD-1. Therefore PD1-Fc (R&D systems; cat. no. 1086-PD) was coated to a maxisorp plate at 1 μg/ml. Coated wells were blocked with 4% BSA in PBS. Thereafter, 0.55 μg/ml biotinylated PD-L1 (BPS bioscience; cat. no. 71105) was added in the presence or absence of IgG in the range of 0.15 to 20 μg/ml. Bound biotinylated PD-L1 was detected with HRP-conjugated streptavidin (BD bioscience: cat. no. 554066) diluted 1:2000 in block buffer. After each incubation step, the ELISA plate was washed three times with PBS-T (PBS-0.05% v/v Tween 20). Bound streptavidin was visualized by $TMB/H_2O_2$ staining and staining was quantified by means of $OD_{450\ nm}$ measurement. Clones were considered to block the interaction of PD-1 with PD-L1 when the ELISA signal was reduced more than 70% at an IgG (PD-1×TT) concentration of 10 μg/ml, compared to a control in which a TT specific competition antibody was added. See FIG. 10 for the results obtained with a representative selection of the PD-1 antibody panel tested as PD-1×TT bispecific molecules.

Affinity Ranking huLAG-3 and huPD-1 Specific Fab Arms Present in the LAG-3×TT and PD-1×TT Bispecific IgG Bispecific antibodies that were shown to bind the respective human and macaque orthologs in FACS were ranked on apparent affinity for both orthologs in FACS. Therefore, the stable cell lines expressing the respective orthologs (Table 1) were harvested and diluted to $10^6$ cells/ml in FACS buffer (PBS/0.5% BSA/0.5 mM EDTA). Cells were centrifuged for 2 minutes at 300 g at 4° C. Supernatant was discarded by inverting the plate(s). 50 μl of each IgG sample, in a 11-step, 2-fold dilution series ranging from 10 to 0.01 μg/ml, was added and incubated for 1H on ice. Cells were centrifuged once, supernatant was removed and cells were washed twice with 150 μl of FACS buffer. 50 μl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Binning huLAG-3 specific Fab arms present in LAG-3×LAG-3 bivalent IgG on domain specificity huLAG-3 binding clones in bivalent IgG format were tested for domain specificity in FACS on HEK293T cells that were transiently transfected with five different pIRES-Neo3 mouse/human LAG-3 hybrid expression constructs, a FL mouse LAG-3 pIRES-Neo3 expression construct (see amino acid insert sequences below) or the pIRES-Neo3_huLAG-3 expression construct used for generation of stable huLAG-3 expressing Freestyle 293F cells (Table 1). The same FACS protocol was used as described above during specificity analysis of the antibody panel. For generation of the hybrid constructs the extracellular domain of mouse and human LAG-3 was divided in 5 domains; 4 Ig-like domains based on Uniprot reference sequences P18627 (huLAG-3) and Q61790 (moLAG-3) and 1 hinge domain from end of Ig-like domain 4 to the transmembrane domain. The following amino acid insert sequences were cloned into pIRES-Neo3 (FIG. 4) via NheI/EcoRI; Text in bold is the signal peptide. Underscored text is the sequence identical to human LAG-3. Text in Italics represent the transmembrane and intracellular domain sequences.

Amino acid sequence full length mouse LAG-3 insert.
(SEQ ID NO: 6)
MREDLLLGFLLLGLLWEAPVVSSGPGKELPVVWAQEGAPVHLPCSLK
SPNLDPNFLRRGGVIWQHQPDSGQPTPIPALDLHQGMPSPRQPAPGR
YTVLSVAPGGLRSGRQPLHPHVQLEERGIARGDFSLWLRPALRTDAG
EYHATVRLPNRALSCSLRLRVGQASMIASPSGVLKLSDWVLLNCSFS
RPDRPVSVHWFQGQNRVPVYNSPRHFLAETFLLLPQVSPLDSGTWGC
VLTYRDGFNVSITYNLKVLGLEPVAPLTVYAAEGSRVELPCHLPPGV
GTPSLLIAKWTPPGGGPELPVAGKSGNFTLHLEAVGLAQAGTYTCSI
HLQGQQLNATVTLAVITVTPKSFGLPGSRGKLLCEVTPASGKERFVW
RPLNNLSRSCPGPVLEIQEARLLAERWQCQLYEGQRLLGATVYAAES
SSGAHSARRISGDLKGGHL*VLVLILGALSLFLLVAGAFGFHWWRKQL*
*LLRRFSALEHGIQPFPAQRKIEELERELETEMGQEPEPEPEPQLEPE*
*PRQL*

Amino acid sequence mo/huLAG-3 chimeric insert A (Full length mouse LAG-3 sequence in which the mouse signal peptide and Ig-like domain 1 is replaced by the human signal peptide and Ig-like domain 1).
(SEQ ID NO: 7)
MWEAQFLGLLFLQPLWVAPVKPLQPGAE<u>VPVVWAQEGAPAQLPCSPT</u>
<u>IPLQDLSLLRRAGVTWQHQPDSGPPAAAPGHPLAPGPHPAAPSSWGP</u>
<u>RPRRYTVLSVGPGGLRSGRLPLQPRVQLDERGRQRGDFSLWLRPARR</u>
<u>ADAGEYRAAVHLRDRALSCRLRLRLGQASMIASPSGVLKLSDWVLLN</u>
<u>CSFS</u>RPDRPVSVHWFQGQNRVPVYNSPRHFLAETFLLLPQVSPLDSG
TWGCVLTYRDGFNVSITYNLKVLGLEPVAPLTVYAAEGSRVELPCHL
PPGVGTPSLLIAKWTPPGGGPELPVAGKSGNFTLHLEAVGLAQAGTY
TCSIHLQGQQLNATVTLAVITVTPKSFGLPGSRGKLLCEVTPASGKE
RFVWRPLNNLSRSCPGPVLEIQEARLLAERWQCQLYEGQRLLGATVY
AAESSSGAHSARRISGDLKGGHL*VLVLILGALSLFLLVAGAFGFHWW*
*RKQLLLRRFSALEHGIQPFPAQRKIEELERELETEMGQEPEPEPEPQ*
*LEPEPRQL*

Amino acid sequence mo/huLAG-3 chimeric insert B (Full length mouse LAG-3 sequence in which the mouse Ig-like domain 2 is replaced by the human Ig-like domain 2).
(SEQ ID NO: 8)
MREDLLLGFLLLGLLWEAPVVSSGPGKELPVVWAQEGAPVHLPCSLK
SPNLDPNFLRRGGVIWQHQPDSGQPTPIPALDLHQGMPSPRQPAPGR
YTVLSVAPGGLRSGRQPLHPHVQLEERGLQRGDFSLWLRPALRTDAG
EYHATVRLPNRALSCSLRLRVG<u>QASMTASPPGSLRASDWVILNCSFS</u>
<u>RPDRPASVHWFRNRGQGRVPVRESPHHHLAESFLFLPQVSPMDSGPW</u>
<u>GCILTYRDGFNVS</u>ITYNLKVLGLEPVAPLTVYAAEGSRVELPCHLPP
GVGTPSLLIAKWTPPGGGPELPVAGKSGNFTLHLEAVGLAQAGTYTC
SIHLQGQQLNATVTLAVITVTPKSFGLPGSRGKLLCEVTPASGKERF
VWRPLNNLSRSCPGPVLEIQEARLLAERWQCQLYEGQRLLGATVYAA
ESSSGAHSARRISGDLKGGHL*VLVLILGALSLFLLVAGAFGFHWWRK*
*QLLLRRFSALEHGIQPFPAQRKIEELERELETEMGQEPEPEPEPQLE*
*PEPRQL*

Amino acid sequence mo/huLAG-3 chimeric insert C (Full length mouse LAG-3 sequence in which the mouse Ig-like domain 3 is replaced by the human Ig-like domain 3).
(SEQ ID NO: 9)
MREDLLLGFLLLGLLWEAPVVSSGPGKELPVVWAQEGAPVHLPCSLK
SPNLDPNFLRRGGVIWQHQPDSGQPTPIPALDLHQGMPSPRQPAPGR
YTVLSVAPGGLRSGRQPLHPHVQLEERGLQRGDFSLWLRPALRTDAG
EYHATVRLPNRALSCSLRLRVGQASMIASPSGVLKLSDWVLLNCSFS
RPDRPVSVHWFQGQNRVPVYNSPRHFLAETFLLLPQVSPLDSGTWGC
VLTYRDGFNVS<u>IMYNLTVLGLEPPTPLTVYAGAGSRVGLPCRLPAGV</u>
<u>GTRSFLTAKWTPPGGGPDLLVTGDNGDFTLRLEDVSQAQAGTYTCHI</u>
<u>HLQEQQL</u>NATVTLAVITVTPKSFGLPGSRGKLLCEVTPASGKERFVW
RPLNNLSRSCPGPVLEIQEARLLAERWQCQLYEGQRLLGATVYAAES
SSGAHSARRISGDLKGGHL*VLVLILGALSLFLLVAGAFGFHWWRKQL*
*LLRRFSALEHGIQPFPAQRKIEELERELETEMGQEPEPEPEPQLEPE*
*PRQL*

Amino acid sequence mo/huLAG-3 chimeric insert D (Full length mouse LAG-3 sequence in which the mouse Ig-like domain 4 is replaced by the human Ig-like domain 4).
(SEQ ID NO: 10)
MREDLLLGFLLLGLLWEAPVVSSGPGKELPVVWAQEGAPVHLPCSLK
SPNLDPNFLRRGGVIWQHQPDSGQPTPIPALDLHQGMPSPRQPAPGR
YTVLSVAPGGLRSGRQPLHPHVQLEERGIARGDFSLWLRPALRTDAG
EYHATVRLPNRALSCSLRLRVGQASMIASPSGVLKLSDWVLLNCSFS
RPDRPVSVHWFQGQNRVPVYNSPRHFLAETFLLLPQVSPLDSGTWGC
VLTYRDGFNVSITYNLKVLGLEPVAPLTVYAAEGSRVELPCHLPPGV
GTPSLLIAKWTPPGGGPELPVAGKSGNFTLHLEAVGLAQAGTYTCSI
HLQGQQLNATVT<u>LAIITVTPKSFGSPGSLGKLLCEVTPVSGQERFVW</u>
<u>SSLDTPSQRSFSGPWLEAQEAQLLSQPWQCQLYQGERLLGATVYAAE</u>
SSSGAHSARRISGDLKGGHL*VLVLILGALSLFLLVAGAFGFHWWRKQ*
*LLLRRFSALEHGIQPFPAQRKIEELERELETEMGQEPEPEPEPQLEP*
*EPRQL*

Amino acid sequence mo/huLAG-3 chimeric insert E (Full length mouse LAG-3 sequence in which the mouse Ig-like domain 4 including the hinge up to the transmembrane sequence is replaced by the human Ig-like domain 4 including the hinge).
(SEQ ID NO: 11)
MREDLLLGFLLLGLLWEAPVVSSGPGKELPVVWAQEGAPVHLPCSLK
SPNLDPNFLRRGGVIWQHQPDSGQPTPIPALDLHQGMPSPRQPAPGR
YTVLSVAPGGLRSGRQPLHPHVQLEERGIARGDFSLWLRPALRTDAG

```
-continued
EYHATVRLPNRALSCSLRLRVGQASMIASPSGVLKLSDWVLLNCSFS

RPDRPVSVHWFQGQNRVPVYNSPRHFLAETFLLLPQVSPLDSGTWGC

VLTYRDGFNVSITYNLKVLGLEPVAPLTVYAAEGSRVELPCHLPPGV

GTPSLLIAKWTPPGGGPELPVAGKSGNFTLHLEAVGLAQAGTYTCSI

HLQGQQLNATVTLAIITVTPKSFGSPGSLGKLLCEVTPVSGQERFVW

SSLDTPSQRSFSGPWLEAQEAQLLSQPWQCQLYQGERLLGAAVYFTE

LSSPGAQRSGRAPGALPAGHLVLVLILGALSLFLLVAGAFGFHWWRK

QLLLRRFSALEHGIQPFPAQRKIEELERELETEMGQEPEPEPEPQLE

PEPRQL
```

Tables 3 and 4 show the bins to which each LAG-3×LAG-3 bivalent IgG was assigned based on domain specificity.

Reference Antibodies

Antibodies that inhibit the function of PD-1 and LAG-3 are known in the art. The information with regard to the anti-PD-1 antibody Nivolumab was generated based on the information disclosed in CA2607147 and was expressed in CHO-S cells. The anti-LAG-3 antibody 25F7 was regenerated based on information provided in WO2010/019570A2 (Medarex. Inc) recloned in an IgG1 backbone and expressed in 293F Freestyle cells.

LAG-3 Blockade Reporter Assay

Figure 11:
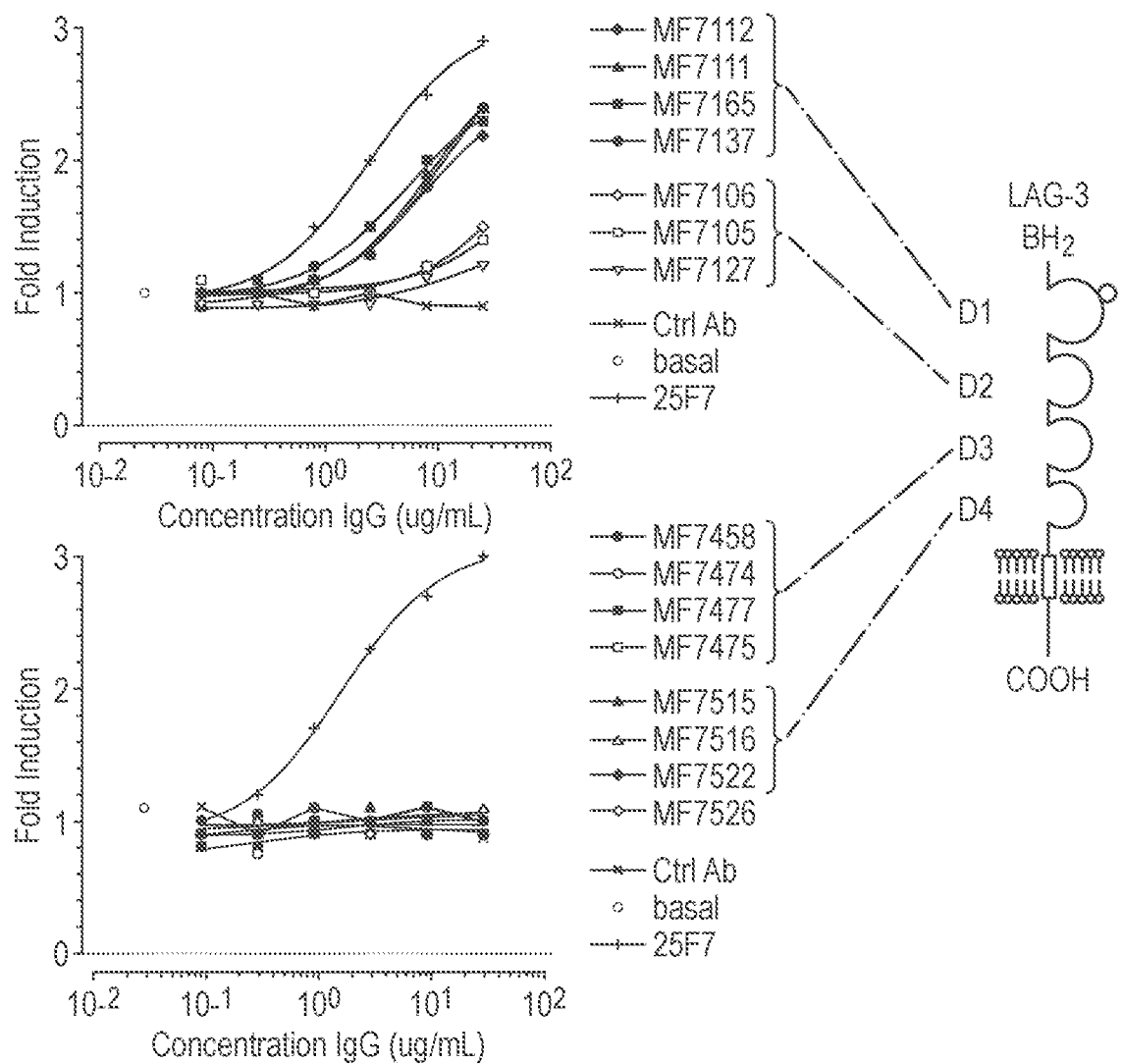

The LAG-3 blockade reporter assays were performed using the LAG-3 blockade reporter assay developed by Promega that uses a two cell system based on Raji cells that expressed MHCII and a Jurkat/NFAT-RE Reporter Cell Line overexpressing LAG-3. Activation of Jurkat cells is controlled via superantigen SED, Staphylococcal Enterotoxins D. LAG-3 Jurkat Effector cells were provided by Promega in a Cell Propagation Model (CPM) format and propagated in RPMI 1640 (+L-glutamine, 10% heat inactivated FBS, 100 μM MEM non-essential amino acids, 1 mM sodium pyruvate, 200 μg/ml Hygromycin and 500 μg/ml G418). Raji cells were propagated in RPMI 1640 (+L-glutamine and 10% heat inactivated FBS). Cells growing in logarithmic phase were harvested and resuspended in RPMI 1640 containing 1% heat inactivated FBS) at a concentration of $2 \times 10^6$ cells/ml Raji and $4 \times 10^6$ cells/ml for Jurkat/NFAT-RE cells. Next, 25 μl Jurkat/NFAT-RE cell suspension was added to the inner wells of a 96 well plate (Corning, Cat #3917). Next, 25 μl test antibody in assay medium (RPMI 1640 containing 1% FBS) in a serial dilution (starting concentration 25 μg/ml) was added to each well. Each plate contained a serial dilution of negative (PG1337) and positive control antibody 25F7 that served as reference controls. Finally 25 μl of a 1:1 mixture of Raji cells and (100 ng/ml) SED (Toxin Technologies) were added. Plates were incubated for 6 H at 37° C., 5% CO, in 95% relative humidity. 40 μl of luciferase (Bio-Glo Luciferase Assay System, cat. no. G794L) was added the next day and the amount of luciferase activity was measured using aBioTek Synergy 2 Multi-Mode Microplate Reader. LAG-3 antibodies were screened in bivalent format to determine their LAG-3 blocking capacity (FIG. 11).

PD-1/PD-L1 Blockade Reporter Assay

The PD-1/PD-L1 blockade reporter assays used were developed by Promega and are based on a two cell system; CHO cells expressing PD-L1, and a T cell activator and a Jurkat/NFAT-RE Reporter Cell Line overexpressing PD-1. The PD-1/PD-L1 blockade reporter assays were performed using the thaw and use format of Promega. PD-L1 expressing cells (cat. no. C187103) were thawed in 14.5 ml Cell Recovery Medium (DMEM/F12 containing 10% FBS). Next, 50 μl cell suspension was added to the inner wells of a 96 well half area plate (Corning, cat. no. 3688). Plates were incubated overnight at 37° C., 5% CO, in 95% relative humidity. Next day, culture medium was removed and 20 μl test antibody in assay medium (RPMI 1640 containing 4% FBS) in a serial dilution (starting concentration 10 μg/ml) was added to each well. Each plate contained a serial dilution of negative (Ctrl Ab) and positive control antibody (Nivolumab) that served as reference controls. PD-1 effector cells (cat no. C187105) were thawed in 5.9 ml Assay medium and 20 μl cell suspension was added to each well. Plates were incubated for 6 H or overnight at 37° C., 5% CO, in 95% relative humidity. 40 μl of luciferase (Bio-Glo Luciferase Assay System, cat. no. G794L) was added the next day and the amount of luciferase activity was measured using aBioTek Synergy 2 Multi-Mode Microplate Reader. Potency was measured as luciferase activity in comparison to the negative control antibody.

PBMC Isolation

Human whole blood was obtained from buffy coats (Sanquin) and was diluted 1:1 with PBS. Leucosep tubes (Greiner Bio-One cat. no. 227 290) were filled with 17.5 m Ficoll-Paque Plus (Amersham Biosciences cat. no. 17-1440-02) warmed at room temperature (RT). Ficoll-Paque Plus was spun down for 30 seconds at 1000×g at RT. 30 ml of diluted whole blood was poured on top. The tubes were spun at 1000×g for 10 minutes at RT and the mononuclear PBMC interface was harvested, washed twice in PBS and resuspended in 250 μl PBS. The PBMCs were counted and readjusted to 1×106/ml in tissue culture medium (DMEM with 10% FCS) and frozen down by adding an equal volume of ice-cold freeze medium (80% culture medium/20% DMSO). Cells were stored in 1 ml aliquots at −150° C. until further use.

SEB Assay

The functional activity of the bispecific antibodies was determined by using PBMCs stimulated by *Staphylococcus* enterotoxin B (SEB). SEB specifically activates T cells expressing the Vβ3 and Vβ8 T cell receptor chain. PBMCs from 3 donors is thawed, washed, counted and resuspended in culture medium (RPMI1640 plus 10% heat inactivated FBS) to a concentration of 2 $10^6$ cells/ml. Cells were seeded in flat bottom 96-well plates ($2 \times 10^5$ cells/well) in the presence of SEB (2000 or 125 ng/ml). Antibody serial dilutions starting at 20 g/ml were added. Each plate contained a serial dilution of negative (Ctrl Ab) and positive control antibody (nivolumab and LAG-3(25F7)) that served as reference controls. Cells were stimulated for 3 days at 37° C., 5% CO2 in 95% relative humidity prior to being tested for cytokine secretion and/or cell surface expression of antigens.

Cytokine Assays

ELISA: After stimulation of T-cells or PBMCs at various times, plates were centrifuged and media was removed. Cytokine levels were detected by AlphaLISA in accordance with the manufacturer's instructions (Perkin Elmer). Concentrations were calculated based on the standard curve.

Luminex assay: Another method used to determine cytokine production in vitro was using luminex analysis developed by eBioscience. Levels of IL-2 were measured in culture supernatants following ranufacturers' instructions. Results were analyzed by eBioscience analysis software.

Screening of the PD-1 Antibody Panel

VH from the PD-antibody panel were produced in 24 well format and tested as bivalent antibodies in a semi log serial titration (starting concentration 10 μg/ml) in the PD-1/PD-L1 blockade reporter assay to rank the antibodies for blocking potency in comparison to Nivolumab. Based on the activity data antibodies were selected from the PD-1 antibody panel for the subsequent PD1×LAG-3 bispecific screen. The activity of the selected candidates in the reporter assay is shown in Table 2. The PD-1 Fab panel was composed of functional activity variants within two antibody clusters i.e. A and B.

Screening PD1×LAG-3 Antibody Panel

Figure 12:
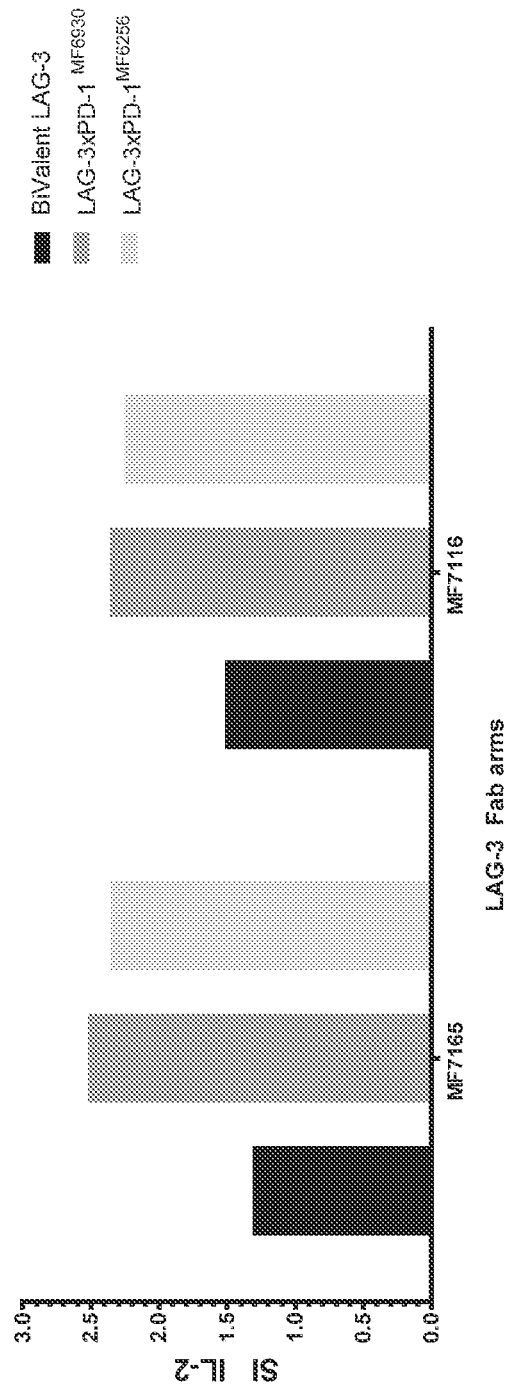
Figure 13:
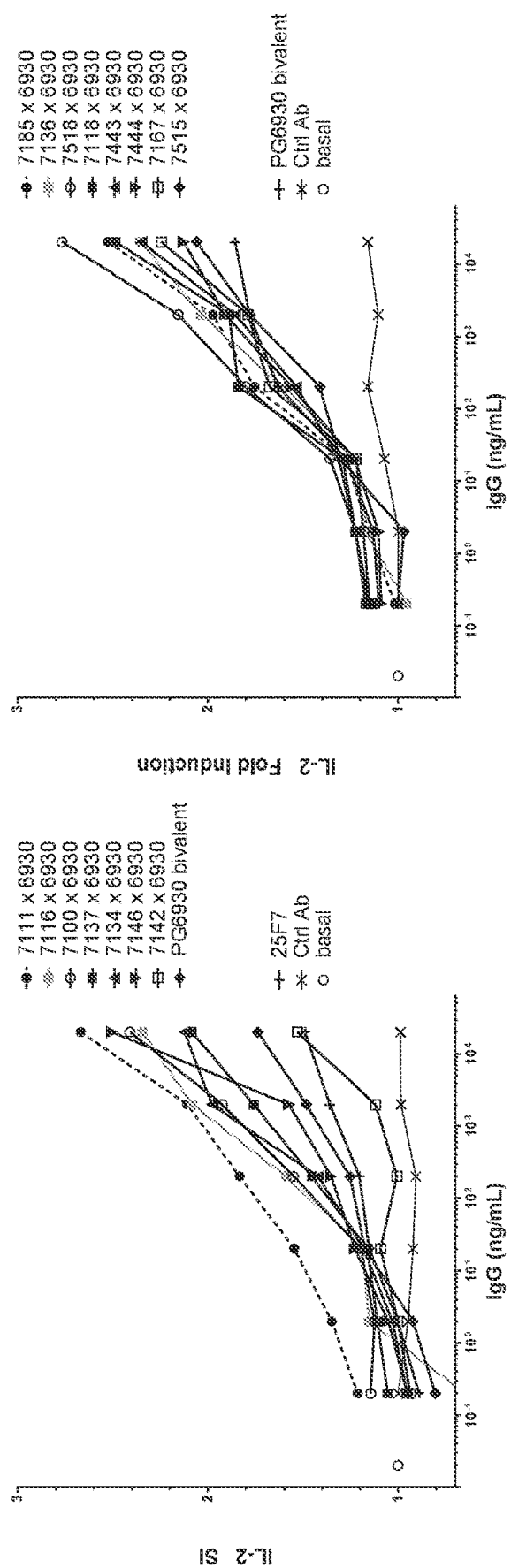

VH from the PD-1 and LAG-3 antibody panel were recloned into the charged engineered Fc-silenced vectors such that upon expression of the antibody heavy chains hetero dimerisation of heavy chains is forced resulting in the generation of bispecific antibodies after transfection. The PD-1 Fab arms were cloned in the MV1625 vector whereas the LAG-3 Fab arms were recloned in the MV1624 vector. Fifteen LAG-3 Lab arms representing the different bins (Table 3) were combined with three PD-1 Fab arms (MF6226, MF6930 and MF6256) displaying a range of PD-1 blocking activities (Table 2). Bispecific LAG-3×PD-1 antibodies (Table 4), their bivalent parental LAG-3 antibodies and negative control antibodies were tested for their capacity to activate T cells by a serial dilution of SFB (2000-500-125-31-8·2 ng/mL). FIG. 12 shows the activity of two LAG-3 bivalent antibodies in comparison to LAG-3× PD-1 antibodies with different PD-1 affinity on PBMC cells stimulated with 2 μg/ml SEB. The activity is represented as stimulation index. Each IL-2 value is compared to the negative control antibody to determine the SI (SI, IL-2 of 2 means 200% increase in IL-2 production when compared to the control antibody). LAG-3×PD-1 bispecific antibodies induced more IL-2 in the SEB assay in comparison to the bivalent LAG-3 antibodies. Selections of bispecific antibodies, representing each bin, were subsequently screened in a serial dilution in a SEE assay whereby PBMC were stimulated with 2 μg/ml SEB (FIG. 13). The majority of bispecific LAG-3×PD-1 antibodies were more potent than the parental PD-1 bivalent antibody or reference LAG-3 antibody in inducing IL-2 release. LAG-3×PD-1 bispecific antibodies that bound other domains than the MHC Class II interacting domain i.e. domain 3 and 4 were also more potent than the parental PD-1 bivalent antibody or reference LAG-3 antibody in inducing IL-2 release.

Example 4. Screening of a PD1×LAG-3 Antibody Panel

Figure 14:
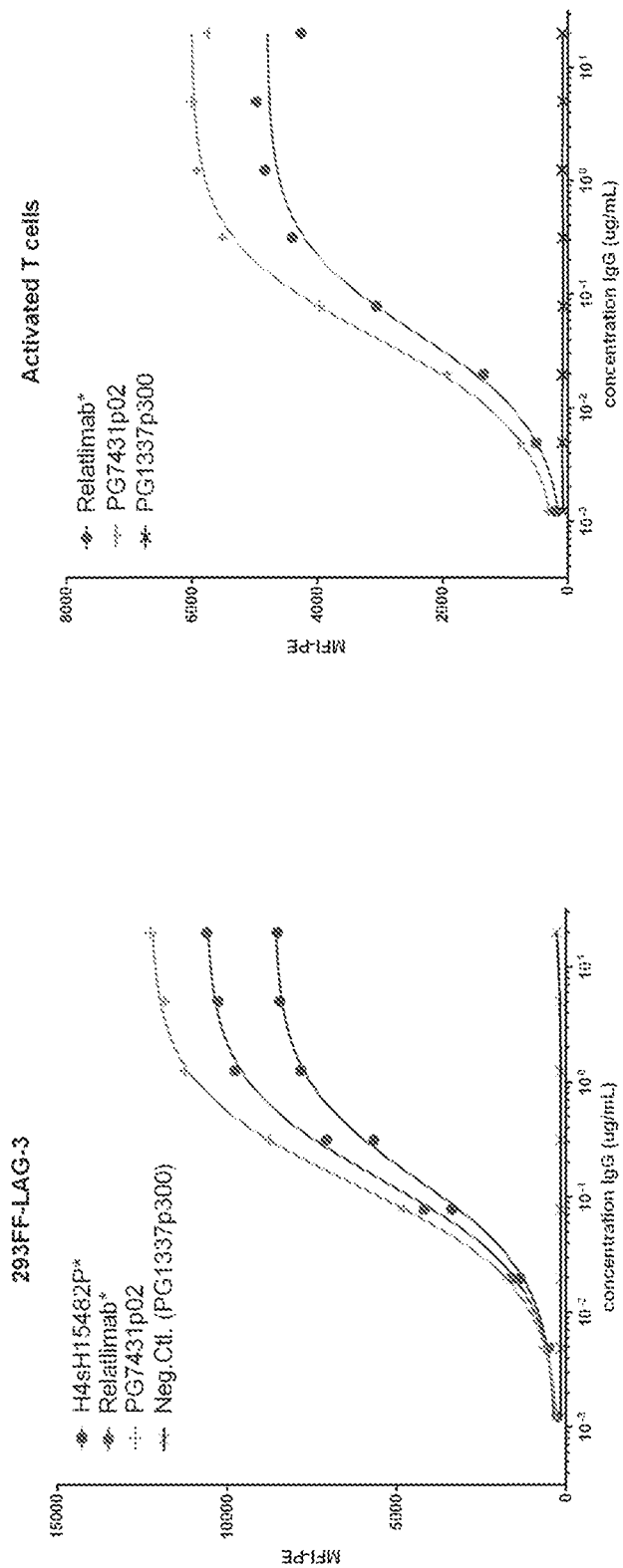

The Fab of antibody 25117, a LAG-3 antibody, was cloned and produced in a human IgG1 format as PG7431 as described above in Example 3. The variable domain of 25F7 was also cloned into a monovalent LAG-3 antibody format as PB22283 wherein the first arm comprised the 25F7 variable domain and the second arm comprised a tetanus toxoid binding variable domain (MF1337). Binding of these antibodies are shown in FIG. 14. PG1337P300 is a control antibody that is not expected to bind to the cells and binds tetanus toxoid.

Binding of these antibodies was compared with the bivalent antibody PG7116 which has two variable domains with MF7116 and a monovalent LAG-3 antibody format wherein the first arm comprised the variable domain of MF7116 and the second arm comprised the tetanus toxoid variable domain comprising MF1337.

Figure 15:
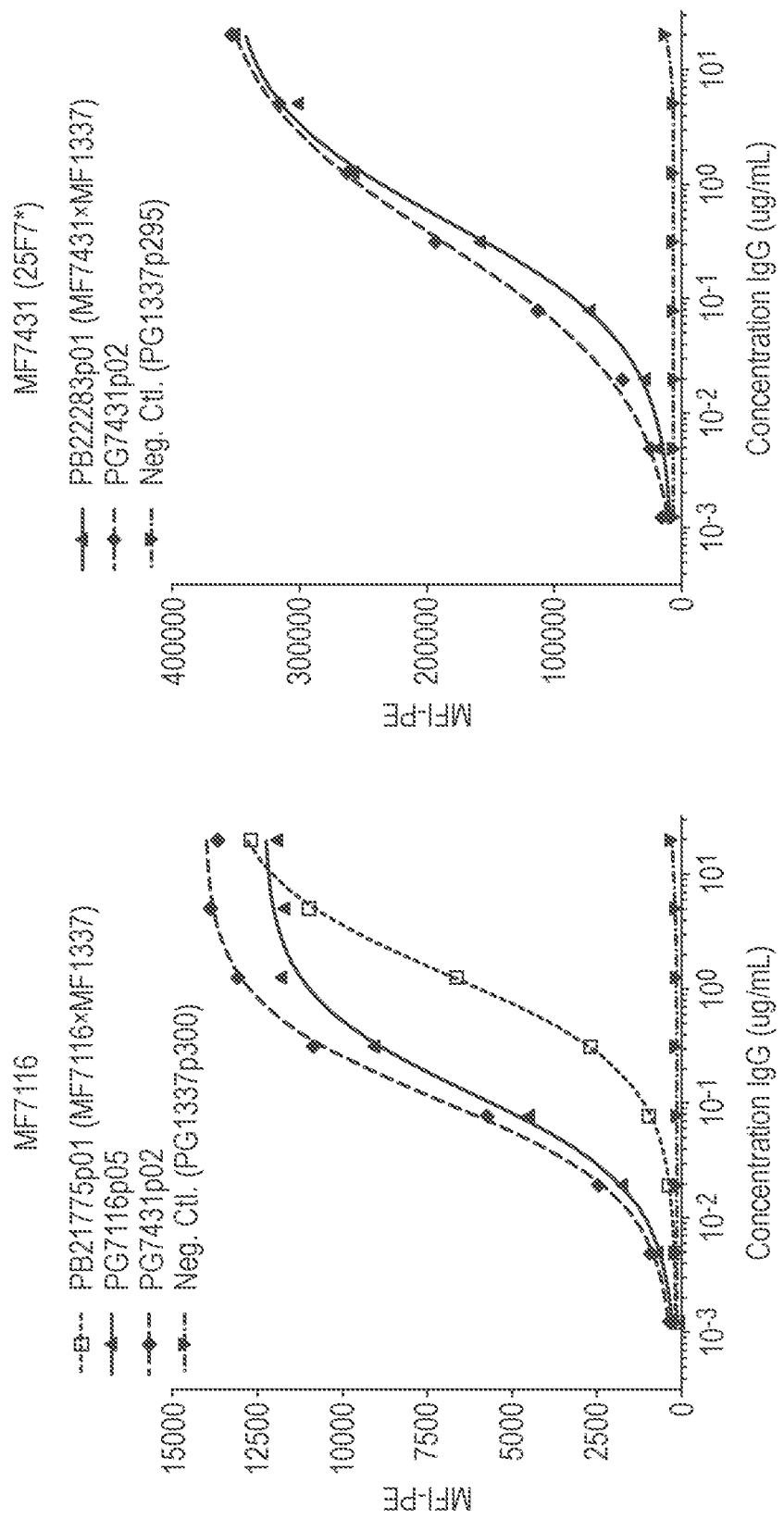

Binding of the antibodies in bivalent form is similar as can be seen by comparing the binding of PG7431 with PG7116 in the left hand panel where the antibodies were titrated on Freestyle 293F_huLAG-3 (293FF LAG-3). The binding of the monovalent variable domain of 25F7 is similar to the binding in bivalent form (compare PB22283 with PG7431 in FIG. 15, right hand panel, where the antibodies were titrated on activated T-cells). Binding of monovalent variable domain with MF7116 is reduced when compared to the bivalent antibody PG7116 (compare P121775 with PG7116, FIG. 15, left hand panel).

Accordingly, LAG-3 IgGs were tested in binding assays in bivalent and monovalent formats, and were compared to a 25F7 (PG7431) antibody. LAG-3 antibodies in bivalent format showed similar binding curves as the benchmark antibodies. Monovalent LAG-3×TT antibodies typically showed reduced binding activity compared to the bivalent molecules.

In order to further characterize PD-1×LAG-3 bispecific antibodies, a panel of bispecific PD-1×LAG-3 antibodies was created as set out in Table 5 and functionally tested in a PD-1×LAG-3 reporter assay.

In the PD1/Lag3 reporter assay, Jurkat Effector Cells as described above (modified to overexpress PD-1 and LAG-3) and target Raji Cells (modified to overexpress PD-L1), SED and LAG-3 antibodies are mixed and incubated. The Jurkat cell line contains a luciferase reporter gene that can become activated through the NFAT (nuclear factor of activated T-cells) pathway. Interaction of the MHCII with LAG-3 will inhibit this signal and blocking the MHCII/LAG-3 interaction by biologics can release the signal as well as the blocking of the PD-1/PD-L1 signal by biologics on the PD-1 receptor.

Figure 16:
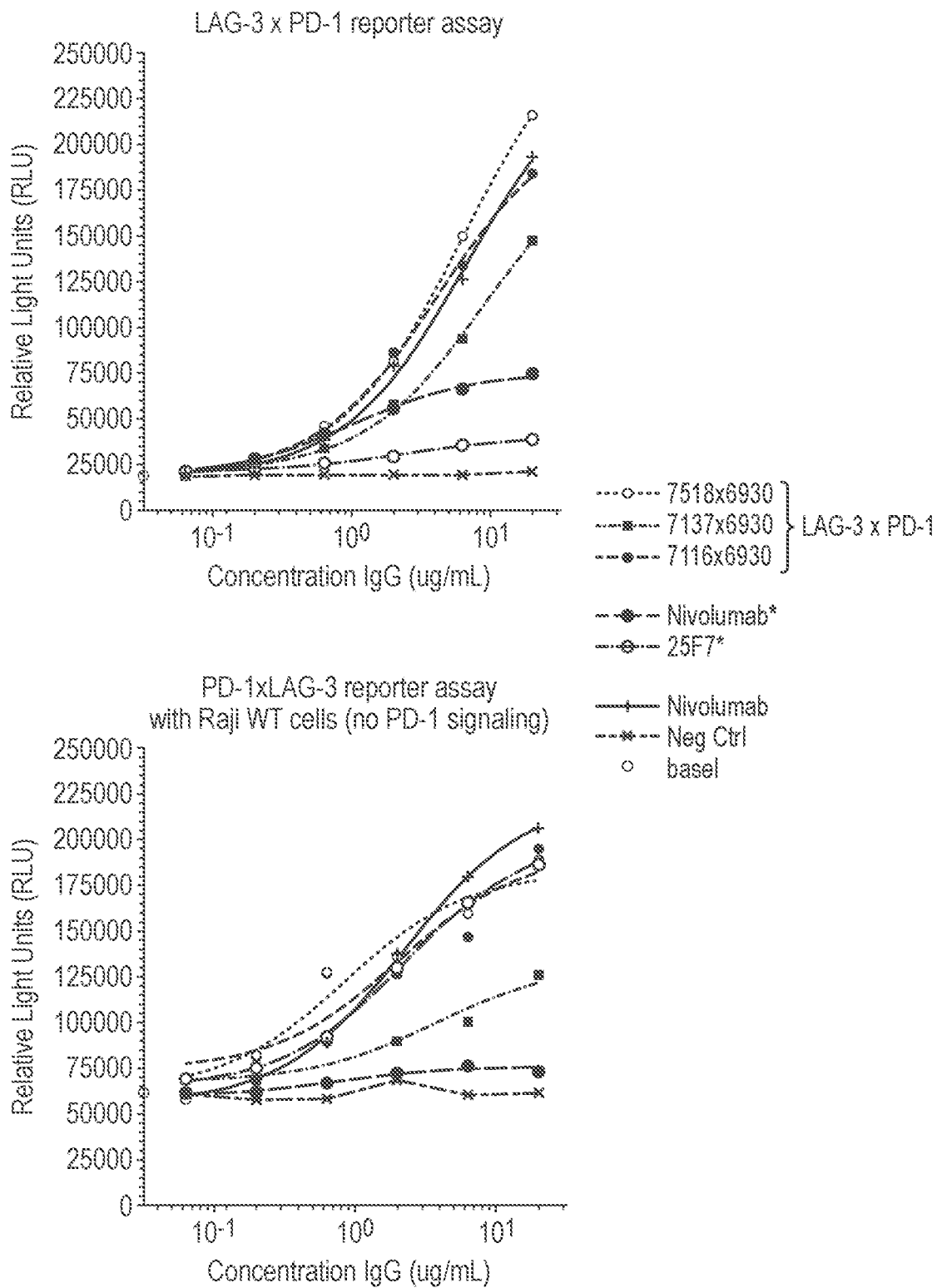

The PD-1×LAG-3 bispecific antibodies were titrated in the PD-1/LAG-3 reporter assay and the activity was compared with a bivalent LAG-3 antibody 25F7 and the bivalent PD-1 antibody (both as described above in Example 3). The bispecific antibodies facilitate the activation of the Jurkat cells at significantly lower concentrations than the monospecific bivalent control antibodies. The activity is comparable to the activity when the two control antibodies are combined, in spite of the fact that the bispecific antibodies are monovalent for each of the targets which, as demonstrated above, can reduce the binding of a monovalent LAG-3 antibody to LAG-3 (see FIG. 16).

Figure 17A:
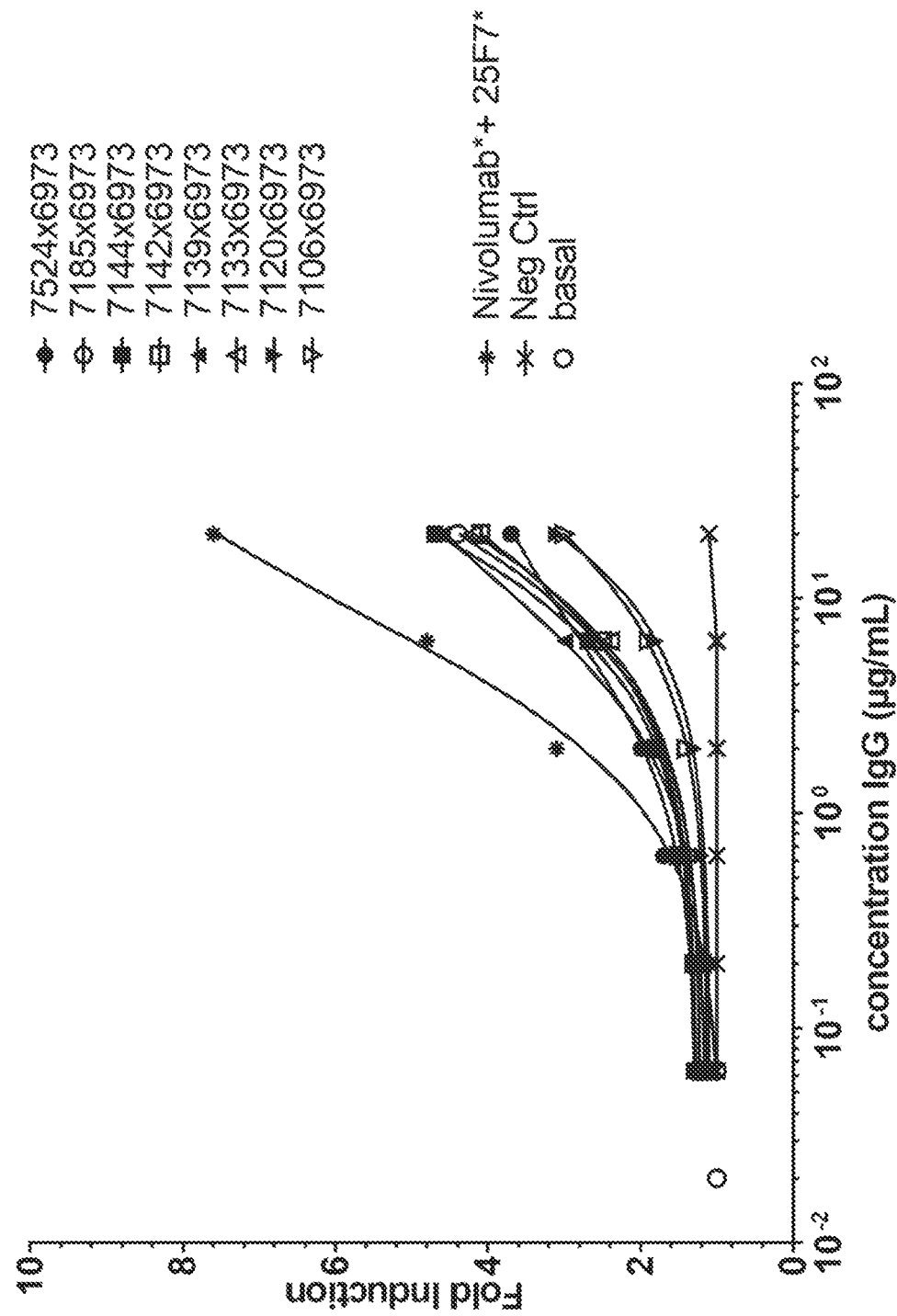
Figure 17B:
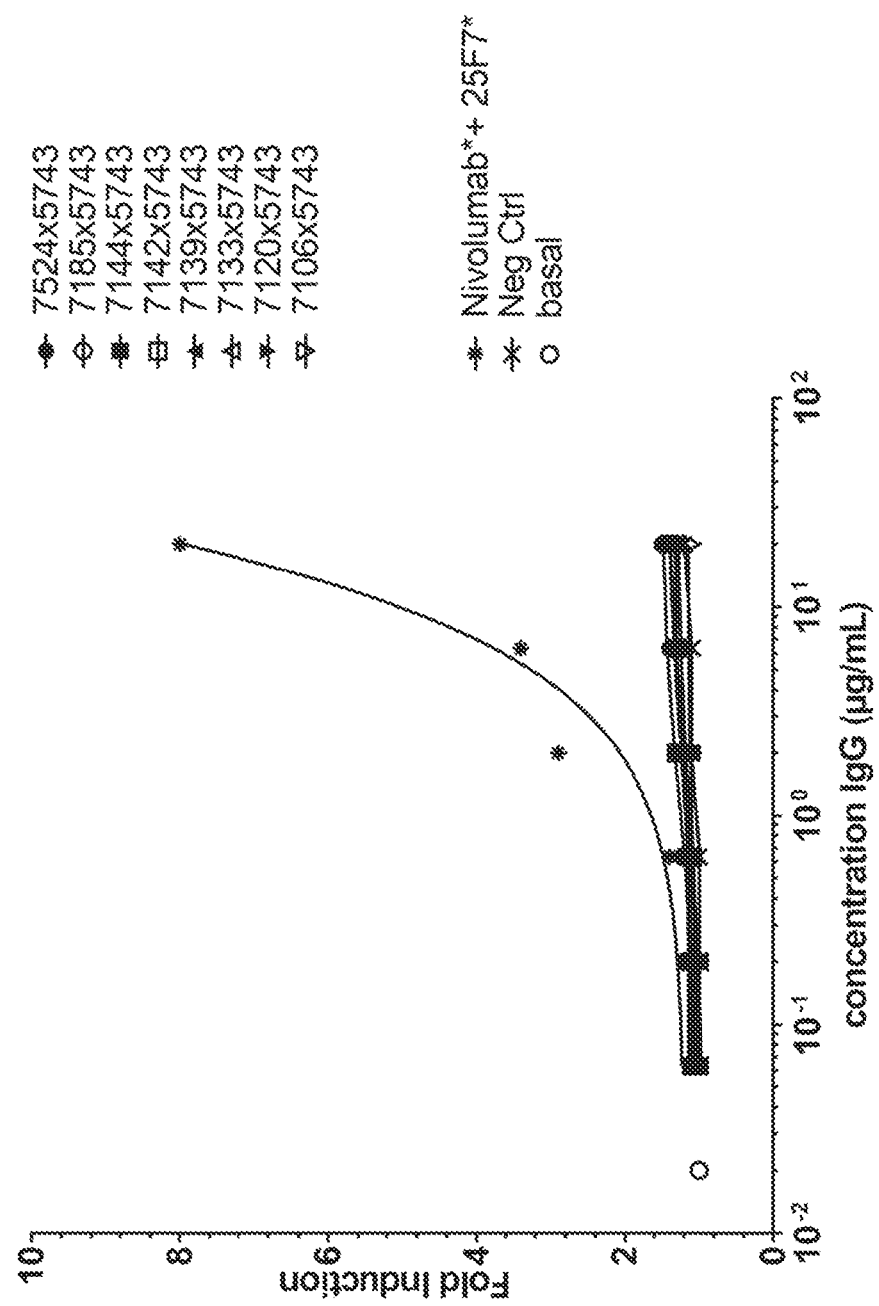
Figure 17C:
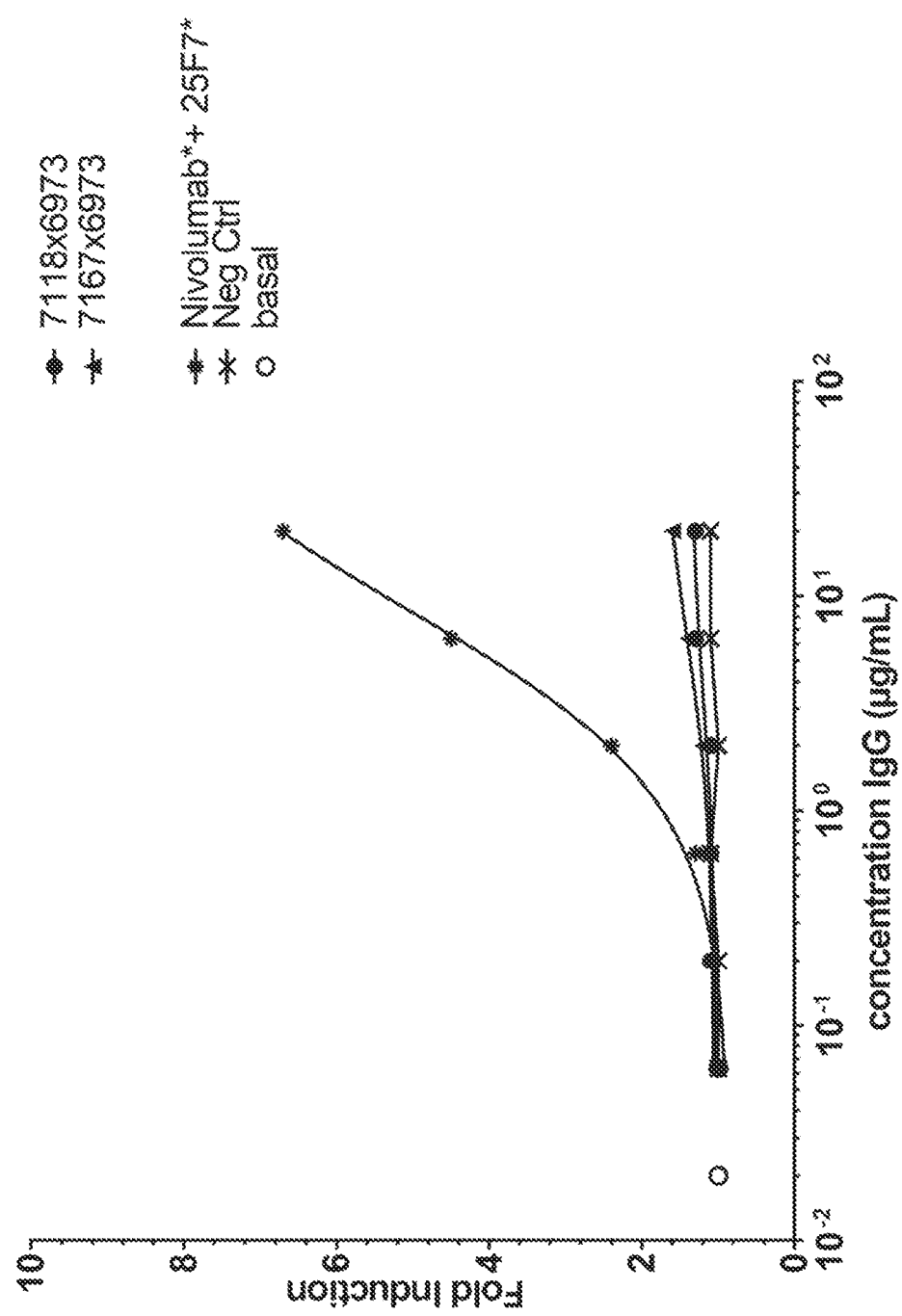

A representative example of the reporter assay screening is presented in FIG. 17: various combinations of LAG-3 and PD-1 variable domains are depicted.

Panel A shows bispecific antibodies with variable domains that bind PD-1 and LAG-3 and that block the binding of natural ligands to the receptor (respectively PD-L1/L2 and MHC class II). The particular bispecific antibodies depicted in panel A allow the activation of the Jurkat reporter cell than a reference having the two monospecific bivalent antibodies to PD-1 and 25F7. Panel B shows bispecific antibodies having the same LAG-3 binding variable domain but now in combination with a PD-1 variable domain that binds PD-1 but that does not block PD-1/PD-L1 signaling. It is clear that the activity of the bispecific antibody in panel A is mediated by at least the arm that binds PD-1 and that blocks PD-1/PD-L1 signaling. Panel C shows the reverse example, the PD-1 arm of panel A in combination with LAG-3 binding variable domains that bind, but that do not block MHC II/LAG-3 signaling. The results shows that the activity of the bispecific antibody depicted in Panel A is mediated at least by a LAG-3 binding arm that blocks the binding of MHC class II to LAG-3.

FIG. 18 summarizes the results of the reporter screening and indicates the area under the curve relative to control.

Figure 19A:
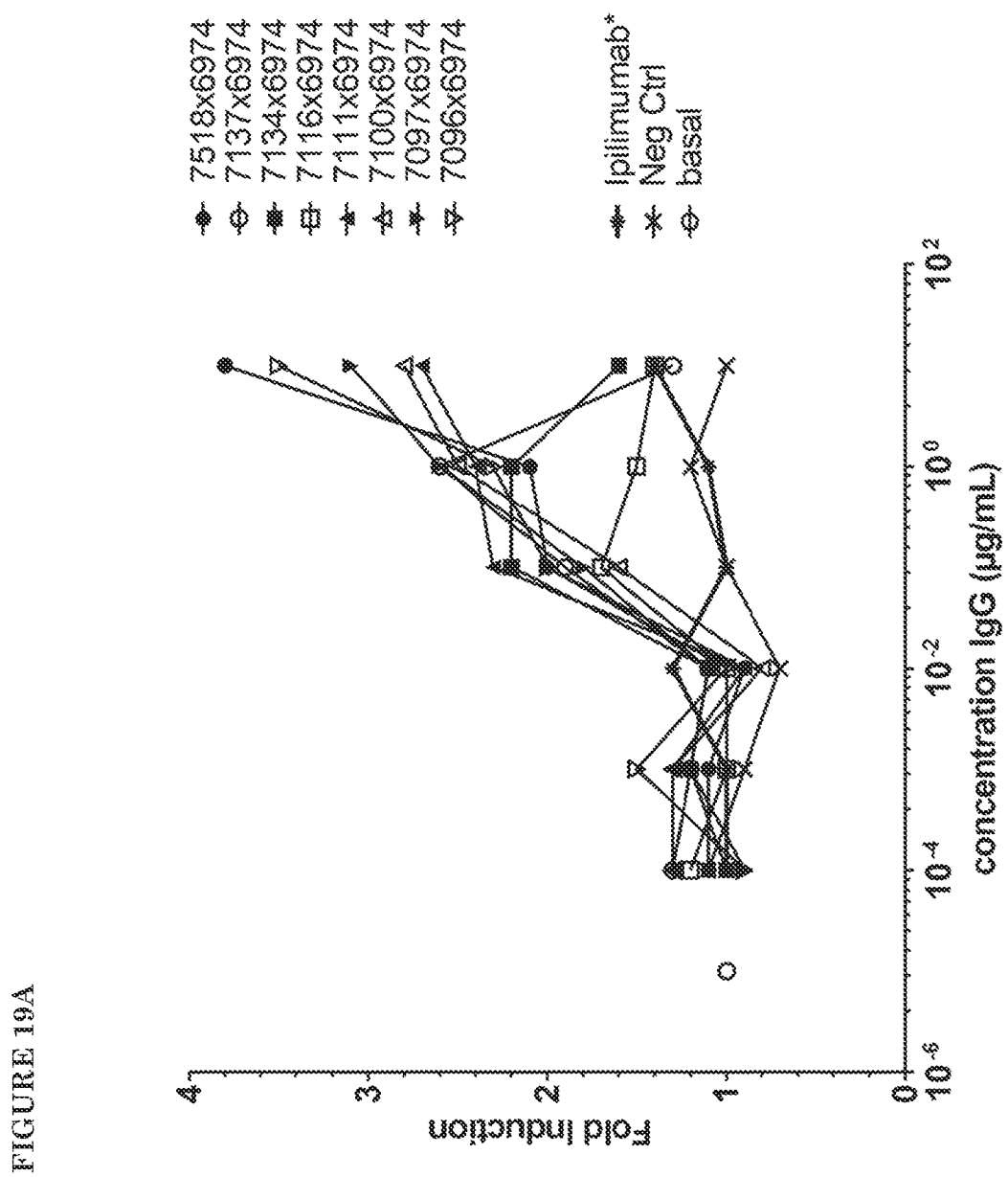
Figure 19B:
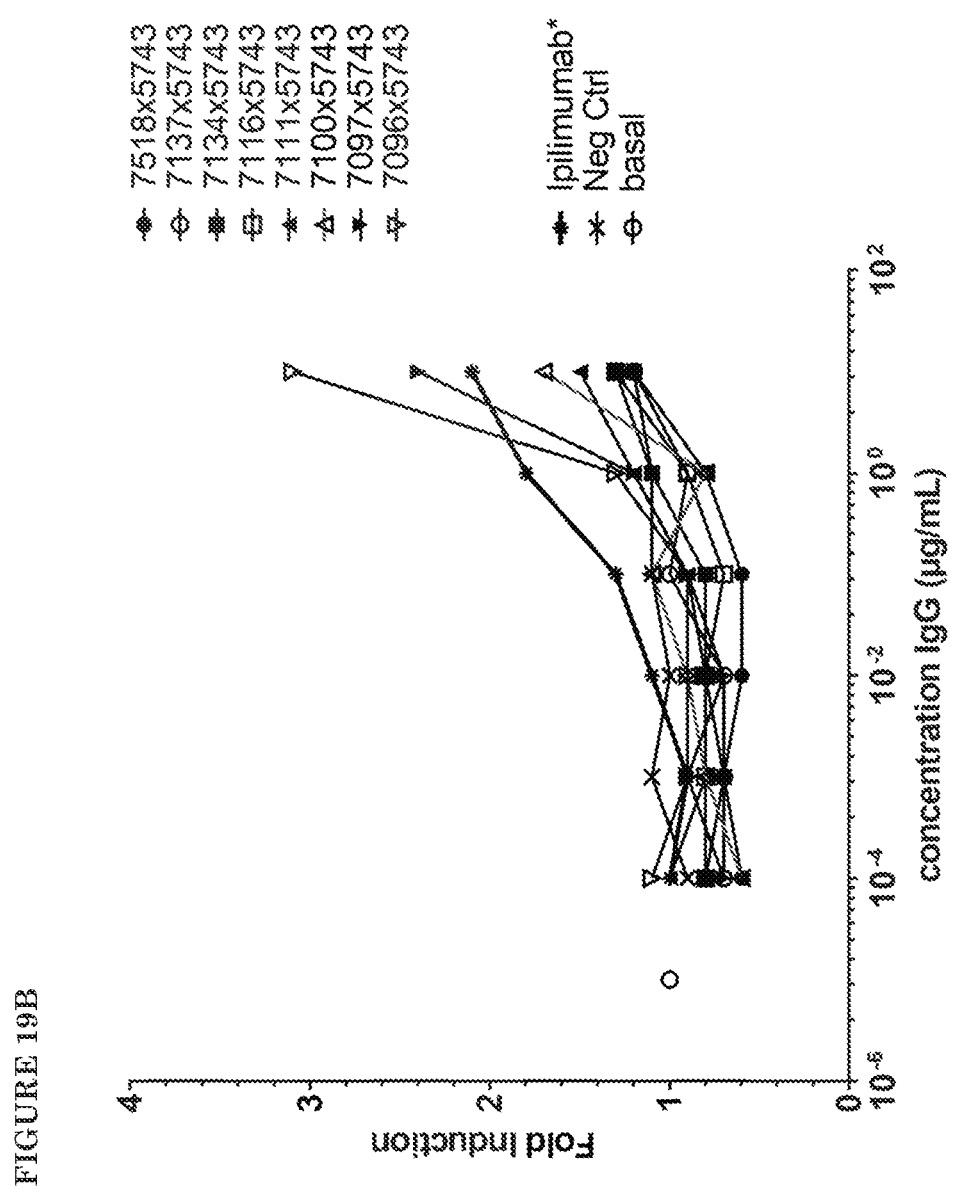
Figure 19C:
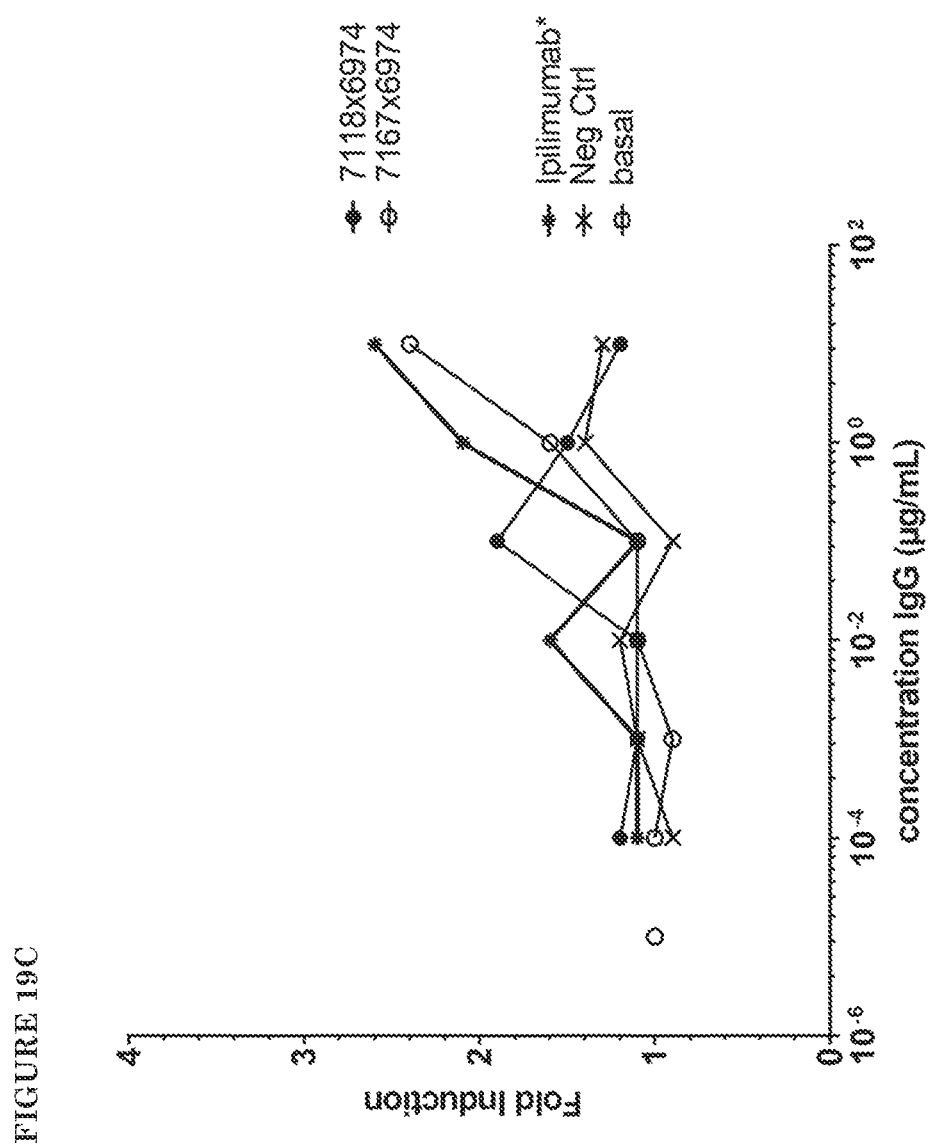

SEB assays were carried out as described in Example 3. FIG. 19 sets out a representative example of an SEB titration assay of the PD-1/LAG-bispecific antibodies as described herein. The figure shows the activity of two LAG-3 bivalent antibodies in comparison to PD-1×LAG-3 antibodies with different PD-1 affinity on PBMC cells stimulated with 2 µg/ml SE.

Panel A shows the result of bispecific antibodies with variable domains that bind PD-1 and LAG-3 and that block the binding of natural ligands to the respective receptors. These antibodies facilitate the production of IL-2 in the PBMC cells. Panel B shows the results with bispecific PD-1×LAG-3 antibodies that have a PD-1 variable domain that binds PD-1 but that does not block the binding of PD-L1 to the receptor. The LAG-3 variable domain blocks the binding of LAG-3 to MHC II. Panel C shows the results with bispecific antibodies with a variable domain that binds LAG-3 but that does not block the binding of LAG-3 to MHC II. The variable domain that binds PD-1 blocks the binding of PD-1 to PD-L1.

Figures 20A, 20B, 20C:
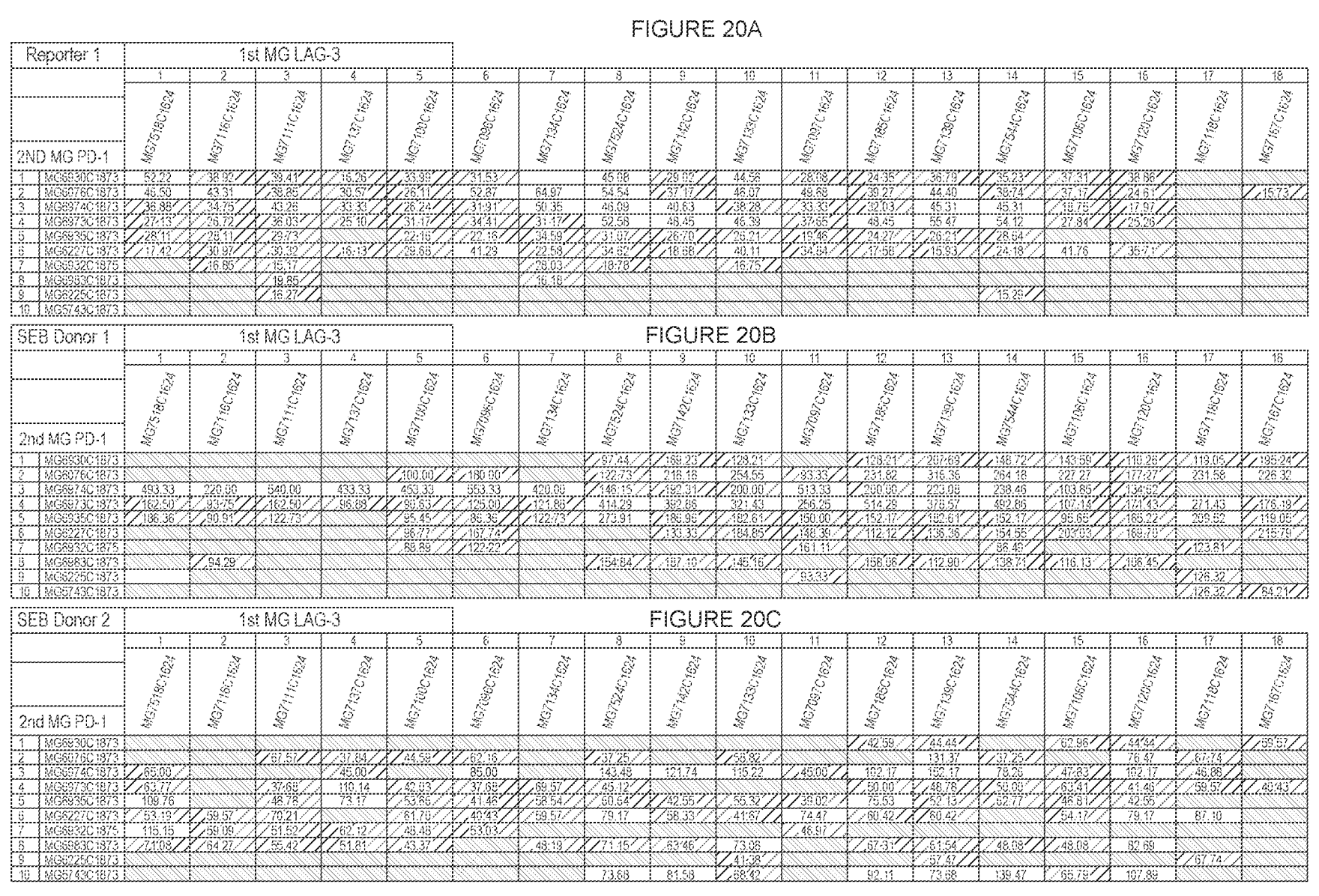

A summary of the screening of the bispecific panel set out in Table 5 is depicted in FIGS. 20A-20C. The PD-1 variable domains were ranked top to bottom depending on the activity of the bivalent antibody in the reporter assay (upper panel) and SEB assay based on 2 donors (middle and lower panel) with the PD-1 variable domain with the highest activity in the reporter assay at the top. The LAG-3 variable domains are ranked high to low in the reporter assay (upper panel) and SEB assay based on 2 donors (middle and lower panel) with the variable domain with the highest activity in the bivalent antibody format in the first column.

The PD-1 arms within bispecific PD-1×LAG3 antibodies were ranked by determining how many times a given arm within a PD-1×LAG3 bispecific appeared in the top 15% of bispecific antibodies based on percent AUC as compared to positive control in: 1) Reporter assay; 2) SEB screening donor 1 (IL-2 data); 3) SEB screening donor 2 (IL-2 data). See FIGS. 21 and 23. This ranking is illustrated in the two right most columns of FIG. 23.

It can be seen that clones with PD-1 arms having a variable domain with a VH of MF6974 or a VH of MF6076 were ranked highest based on the above criteria with most of the LAG-3 arms in the Reporter and SEB assays.

The same approach was taken for bispecific antibodies carrying a specific LAG-3 arms, which were also scored on the basis of how many times they were present in the top 15% (those arms with same score in the top 15% were further ranked by using the top 25% scores). The final ranking is set out in FIG. 22.

Several bivalent, monospecific antibodies (in IgG format) that bind LAG3 domain 1, according to mouse/human LAG-3 hybrid binning experiments described above, scored highest based on AUC percent of a positive control in a reporter assay. However, the bispecific antibodies binding PD1 and LAG3 that were ranked the highest based on reporter assays and in the SEB assay in IL-2 induction were those that domain 2 (as determined according to the mouse/human LAG-3 hybrid experiments).

This is summarized in FIG. 24. Of the top eight bispecifics as ranked based on the PD1/LAG3-reporter assay and SEB, six comprised a LAG3 arm that binds domain 2 (as determined according to the mouse/human LAG-3 hybrid experiments). The activity of the LAG3 arms (on the basis of AUC percent of control) from these 6 bispecifics as determined by LAG3 reporter assay in bivalent monospecific format was typically lower than that of LAG3 arms tested in the same format which were determined to bind domain 1.

Example 5

Bispecific PD-1×LAG-3 Antibodies Enhance IFNγ Production by CD14+ T Cells in a Mixed Lymphocyte Reaction.

Mixed lymphocyte reaction (MLR) assays are commonly used to understand the effects of antibodies on T-cell activation and proliferation. Such assays aid understanding of whether such compounds will affect the potential of T cells to mount a response in the tumor microenvironment. Here we used an allogeneic MLR protocol with immature DCs to determine the ability of bispecific PD-1×LAG-3 antibodies to enhance IFNγ production by CD14+ T cells, compared with that of benchmark reference antibodies. The responsiveness of the T cells was quantified by measuring the levels of IFNγ in culture supernatant.

To this end, human peripheral blood mononuclear cells (PBMCs) from healthy donors were prepared from buffy coats. Immature monocyte-derived dendritic cells (Mo-DCs) were prepared by isolating CD14+ cells (EasySep Stemcell, lot no. 16C69672) using magnetic activated cell sorting (MACS) and culturing these in differentiation medium for seven days. Responder T cells derived from a different donor to that used for the Mo-DCs were prepared from cryopreserved PBMCs on the day required, using a T-cell isolation kit (EasySep Stemcell, lot no. 16D70573) to obtain untouched T cells. Six separate MLRs were performed to provide biological replication.

For the assay, $1×10^4$ immature Mo-DCs were co-cultured with $1×10^5$ CD14+ T cells for 4 days, in the presence or absence of test antibody at an end concentration of 10 µg/mL. Cultures were performed in triplicate. Supernatants were collected at the end of the culture period and assessed for IFNγ by ELISA (R&D BioTechne, lot no. 342687) according to the manufacturer's instructions with plates read at 450 nm.

Results

The MLR study comprised experimental groups of a LAG3/PD1 bispecific (PB15307=MF7137 (LAG3) and MF6930 (PD1)) and LAG3 isotype control group (monospecific antibody against a LAG-3 (bivalent monospecific antibody PG7431), Tetanus and mIgG1). Single cell controls and a vehicle control group were also included.

Cultures were performed in triplicate to provide technical replicates. At the end of the 4-day culture period supernatant was collected and ELISAs performed to assess effects of the antibodies on the production of IFN-y, according to manufacturer's instructions with plates read at 450 nM.

CD14+ cells were sorted on DO and cultured for 7 days, immature DCs were used on D7 and mature DCs were obtained by culturing for an additional 3 days in maturation medium. CD14 positivity was assessed at DO to confirm purity of the initial sort, and in immature and matured DCs at D7 and D10, respectively, to confirm downregulation of CD14 to indicate differentiation to Mo-DCs (data not shown). Viability and activation markers (CD80, CD83 and CD86) were also assessed on both immature and matured DCs to confirm differentiation and maturation. Mo-DCs (immature or mature) were cultured with responder T cells for 4 days before supernatant was collected and ELISAs performed to assess effects of the test antibodies on production of IFN-y. In the mature MLR (mMLR) the donor variance was such that the data were normalized to vehicle control for each donor (raw data and normalized.

Figure 25:
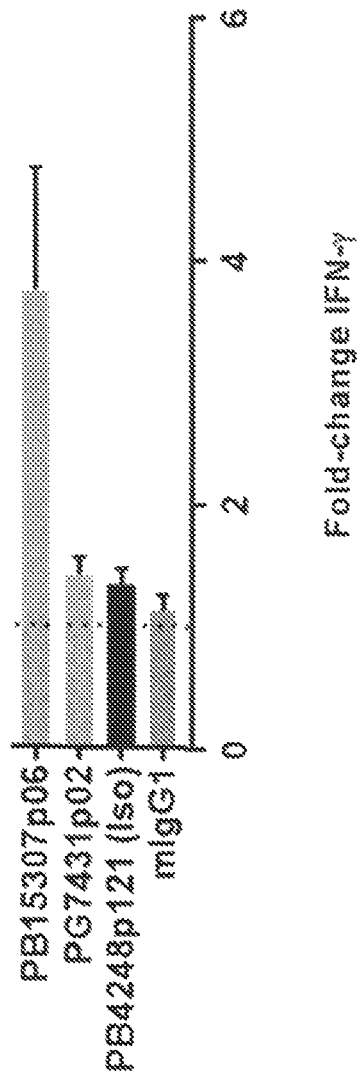

In FIG. 25 the results of the test are shown. The bispecific antibody specific for PD-1/LG-3 out-performed IFN-y production by CD14+ T cells in MLR significantly over the control and LAG3 surrogate monospecific antibody.

TABLE 1

Expression constructs for each target that were used for DNA immunization (pVAX1 vector based) and for generation of stable Freestyle 293F or CHO-S cell lines (pIRES-neo3 vector based or similar)

| Target | Vectors | Stable cell line |
| --- | --- | --- |
| PD-1 | pVAX1_huPD-1 | NA |
|  | pIRES-neo3_huPD-1 | CHO-S_huPD-1 |
|  | pIRES-neo3_maPD-1 | CHO-S_maPD-1 |
| LAG-3 | pVAX1_huLAG-3 | NA |
|  | pVAX1_raLAG-3 | NA |
|  | pIRES-neo3_huLAG-3 | Freestyle 293F_huLAG-3 |
|  | pIRES-neo3_maLAG-3 | Freestyle 293F_maLAG-3 | hu = human,
ma = macaque,
ra = rat,
NA = not applicable

TABLE 2

Functional activity of PD-1 Fab arms as measured in the PD-1/PD-L1 blockade reporter assay as a bivalent antibody in comparison to the positive control Nivolumab. Variants of the same cluster (B) that displayed different of PD-1 blocking activity were tested.

| SEQ ID NOS. | Clone | CDR3 | Cluster | % Activity of pos control |
| --- | --- | --- | --- | --- |
| SEQ ID NO: 111 | MF6226 | GGYSGYGGDSFDL | A | 47.77614647 |
| SEQ ID NO: 112 | MF6256 | GTVEATLLFDF | B | 57.85260834 |
| SEQ ID NO: 113 | MF6930 | GTVEATLLFDY | B | 51.50445453 |

TABLE 3

Panel of LAG-3 Fab arms describing binning based on FACS profiles, domain binding and LAG-3 blocking activity as bivalent antibody.

| SEQ ID NO: | ID | CDR3H | VH | Bin | LAG-3 block |
| --- | --- | --- | --- | --- | --- |
| SEQ ID NO: 124 | 7111 | IPLTGEFDY | VH4-59 | D1 | Yes |
| SEQ ID NO: 142 | 7165 | GGTYYYGSGSYYTLDY | VH1-24 | D1 | Yes |
| SEQ ID NO: 143 | 7116 | DGDNWDVFDI | VH3-30 | D1 | Yes |
| SEQ ID NO: 144 | 7100 | ERGWDVFDI | VH3-30 | D1 | Yes |
| SEQ ID NO: 145 | 7137 | GGTYYYGSGSYYTLDF | VH1-24 | D1 | Yes |
| SEQ ID NO: 146 | 7518 | DGSGWDDFDY | VH1-18 | D1 + D4 | Yes |
| SEQ ID NO: 147 | 7134 | EPNWGVYFDY | VH7-4-1 | D2 | Yes |
| SEQ ID NO: 148 | 7146 | DREVGAIYYFDY | VH1-69 | D2 | Yes |
| SEQ ID NO: 149 | 7142 | ERDIGSLYYFDS | VH1-69 | D2 | Yes |
| SEQ ID NO: 150 | 7185 | DREMFTLYFFDQ | VH1-69 | D2 | Yes |
| SEQ ID NO: 151 | 7136 | DSTYYYTSGSYSVFDY | VH3-23 | D2 | No |

TABLE 3-continued

Panel of LAG-3 Fab arms describing binning based on FACS profiles, domain binding and LAG-3 blocking activity as bivalent antibody.

| SEQ ID NO: | ID | CDR3H | VH | Bin | LAG-3 block |
|---|---|---|---|---|---|
| SEQ ID NO: 117 | 7118 | VPAAATPSGTYY-WIFDL | VH3-23 | D3 | No |
| SEQ ID NO: 152 | 7443 | DTSTWQRGGYKAFDY | VH3-23 | D3 | No |
| SEQ ID NO: 153 | 7167 | DRGYDYSGSYHNWFDP | VH3-23 | D4 | No |
| SEQ ID NO: 154 | 7515 | RPGPALGDLDS | VH1-18 | D4 | No |
| SEQ ID NO: 155 | 7444 | DTGQSWSNYYHAFDY | VH3-23 | hu/mo cross-reactive-hu D3 | No |

TABLE 4

Panel of LAG-3 Fab arms describing binning based on FACS profiles and domain binding.

| | ID | CDR3H | VH | Bin |
|---|---|---|---|---|
| | 7096 | DLLYKWNYVEGFDI | VH4-59 | D1 |
| | 7097 | DLLYKWNYVEGFDI | VH4-59 | D1 |
| | 7106 | DKAVAGLYYFDS | VH1-69 | D2 |
| | 7118 | VPAAATPSGTYYWIFDL | VH3-23 | D3 |
| | 7120 | ERELGALYAFDI | VH1-69 | D2 |
| | 7133 | DRETGTLYYFDY | VH1-69 | D2 |
| | 7139 | DRAIGTLYYFDY | VH1-69 | D2 |
| | 7144 | DRDSGGLYYFDS | VH1-69 | D2 |
| | 7524 | GSILAAQMWGDI | VH1-18 hu/mo cross-reactive-mo 1 | |

| SEQ ID No: | ID | CDR3H | VH | Bin |
|---|---|---|---|---|
| SEQ ID NO: 114 | 7096 | DLLYKWNYVEGFDI | VH4-59 | D1 |
| SEQ ID NO: 115 | 7097 | DLLYKWNYVEGFDI | VH4-59 | D1 |
| SEQ ID NO: 116 | 7106 | DKAVAGLYYFDS | VH1-69 | D2 |
| SEQ ID NO: 117 | 7118 | VPAAATPSGTYYWIFDL | VH3-23 | D3 |
| SEQ ID NO: 118 | 7120 | ERELGALYAFDI | VH1-69 | D2 |
| SEQ ID NO: 119 | 7133 | DRETGTLYYFDY | VH1-69 | D2 |
| SEQ ID NO: 120 | 7139 | DRAIGTLYYFDY | VH1-69 | D2 |
| SEQ ID NO: 121 | 7144 | DRDSGGLYYFDS | VH1-69 | D2 |
| SEQ ID NO: 122 | 7524 | GSILAAQMWGDI | VH1-18 hu/mo cross-reactive-mo 1 | |

TABLE 5

Overview PB numbers and their MF composition

| | PD-1 | | |
|---|---|---|---|
| LAG-3 | MF6930 | MF6226 | MF6256 |
| MF7111 | PB15292 | PB16336 | PB15254 |
| MF7116 | PB15296 | PB16367 | PB15258 |
| MF7100 | PB15289 | PB16369 | PB15251 |
| MF7137 | PB15307 | PB16365 | PB15269 |
| MF7518 | PB15383 | PB16364 | PB15347 |
| MF7134 | PB15305 | PB16337 | PB15267 |
| MF7146 | PB15313 | PB16338 | PB15275 |
| MF7142 | PB15311 | PB16339 | PB15273 |
| MF7165 | PB15317 | PB16366 | PB15279 |
| MF7185 | PB15363 | PB16340 | PB15359 |
| MF7136 | PB15306 | PB16341 | PB15268 |
| MF7118 | PB15297 | PB16342 | PB15259 |
| MF7443 | PB15369 | PB16343 | PB15333 |
| MF7444 | PB15403 | PB16346 | PB15393 |
| MF7167 | PB15318 | PB16344 | PB15280 |
| MF7515 | PB15380 | PB16345 | PB15344 |

TABLE 5

Overview of LAG-3 arms and PD-1 arms and which heavy chains the variable domains are associated with in a bispecific antibody

| Target | MF | Target | MF |
|---|---|---|---|
| LAG-3 | 7096 | PD-1 | 5743 |
| | 7097 | | 6076 |
| | 7100 | | 6225 |
| | 7106 | | 6227 |
| | 7111 | | 6930 |
| | 7116 | | 6932 |
| | 7118 | | 6935 |
| | 7120 | | 6974 |
| | 7133 | | 6983 |

TABLE 5-continued

Overview of LAG-3 arms and PD-1 arms and which heavy chains the variable domains are associated with in a bispecific antibody

| Target | MF | Target | MF |
|---|---|---|---|
| | 7134 | | |
| | 7137 | | |
| | 7139 | | |
| | 7142 | | |
| | 7144 | | |
| | 7167 | | |

TABLE 5-continued

Overview of LAG-3 arms and PD-1 arms and which heavy chains the variable domains are associated with in a bispecific antibody

| Target | MF | Target | MF |
|---|---|---|---|
| | 7185 | | |
| | 7444 | | |
| | 7518 | | |
| | 7524 | | |

The invention claimed is:

1. An antibody or variant thereof that comprises a variable domain that can bind to an extracellular part of PD-1 and a variable domain that can bind to an extracellular part of LAG3;
   wherein the variable domain that can bind to an extracellular part of PD-1 blocks the binding of PD-1 to PD-L1 and/or PD-L2; and
   wherein the variable domain that can bind to an extracellular part of LAG3 comprises a heavy chain variable region with a CDR1, CDR2 and CDR3 region that comprises the amino acid sequence of the CDR1, CDR2 and CDR3 of a heavy chain variable region according to any one of SEQ ID NO: 58-81.

2. The antibody or variant thereof of claim 1, wherein said LAG-3 binding variable domain binds to LAG-3 extracellular domain 1, 2, 3 or 4.

3. The antibody or variant thereof of claim 1, wherein the variable domain that binds an extracellular part of PD-1 is defined as a variable domain that when in a bivalent monospecific antibody that comprises two of said variable domains that bind PD-1, inhibits PD-1/PD-L1 mediated inhibition in a Jurkat cell in a range of 20-150% when compared to the inhibition obtained with the antibody Nivolumab on a Jurkat cell.

4. The antibody or variant thereof of claim 1, wherein said variable domain that binds PD-1 comprises a heavy chain variable region with a CDR1, CDR2 and CDR3 region that comprises the amino acid sequence of the CDR1, CDR2 and CDR3 of a heavy chain variable region according to any one of SEQ ID NO: 47-57.

5. The antibody or variant thereof of claim 1, wherein the variable domain that can bind to an extra cellular part of PD-1 and comprises a heavy chain variable region that comprises the amino acid sequence of the heavy chain variable region according to any one of SEQ ID NO: 47-57, having at most 15 amino acid insertions, deletions, substitutions or a combination thereof.

6. The antibody or variant thereof of claim 1, comprises a variable domain that can bind to an extra cellular part of LAG3 and comprises a heavy chain variable region that comprises the amino acid sequence of the heavy chain variable region according to any one of SEQ ID NO: 58-81, having at most 15 amino acid insertions, deletions, substitutions or a combination thereof.

7. The antibody or variant thereof of claim 1, wherein the antibody comprises:
   a variable domain that can bind to an extra cellular part of LAG-3 which comprises a heavy chain variable region that comprises the amino acid sequence of the heavy chain variable region according to any one of SEQ ID NO: 73, 74, 78, 79, 81, having at most 15 amino acid insertions, deletions, substitutions or a combination thereof; and
   a variable domain that can bind to an extra cellular part of PD-1 which comprises a heavy chain variable region that comprises the amino acid sequence of the heavy chain variable region according to SEQ ID NO: 47, having at most 15, amino acid insertions, deletions, substitutions or a combination thereof.

8. The antibody or variant thereof of claim 1 which comprises a light chain variable region having the CDR1, CDR2 and CDR3 sequences of the light chain variable region according to SEQ ID NO: 30, or CDR1, CDR2 and CDR3 sequences that deviate in no more than three amino acids from the light chain variable region CDR1 and CDR2 and CDR3 sequences of the light chain variable region according to SEQ ID NO: 30.

9. The antibody or variant thereof of claim 1 which comprises a light chain variable region having a sequence that is at least 80% identical to the amino acid sequence according to SEQ ID NO: 30.

10. A composition or kit of parts comprising at least one antibody or variant thereof according to claim 1.

11. A pharmaceutical composition comprising at least one antibody or variant thereof of claim 1 and a pharmaceutically acceptable carrier, diluent or excipient.

12. A nucleic acid molecule with a length of at least 15 nucleotides encoding at least one CDR region or encoding at least a heavy chain variable region of the variable domain that can bind to an extracellular part of LAG3 as defined in claim 1.

13. The nucleic acid molecule according to claim 12, encoding a heavy chain variable region according to any one of SEQ ID NO: 58-81.

14. A vector comprising a nucleic acid molecule or functional equivalent thereof according to claim 12.

15. An isolated or recombinant cell, or a non-human animal, comprising a nucleic acid molecule according to claim 12.

16. A method for treating a cancer or an infection with a pathogen comprising administering to a subject in need thereof a therapeutically effective amount of an antibody or variant of claim 1.

17. A method for producing an antibody or variant thereof of claim 1 from a single cell, wherein said antibody or variant thereof comprises two CH3 domains that are capable of forming an interface, said method comprising providing:
   a cell having a) a first nucleic acid molecule encoding a IgG heavy chain that specifically recognizes an extracellular part of a PD-1, and that contains a 1st CH3 domain, and b) a second nucleic acid sequence encoding a IgG heavy chain that specifically recognizes an extracellular part of LAG-3, and that contains a 2nd CH3 domain, wherein said nucleic acid sequences encode residues for preferential pairing of said 1st and 2nd CH3 domains, said method further comprising the step of culturing said cell and allowing for expression of said nucleic acid sequences and harvesting said antibody or variant thereof from the culture.

18. The method according to claim 17, wherein said cell has a third nucleic acid sequence encoding a common light chain.

19. The method according to claim 17, wherein said first nucleic acid encodes said first CH3 domain comprising the amino acid substitutions L351K and T366K (numbering according to the EU numbering) and wherein said second nucleic acid encodes said second CH3 domain comprising the amino acid substitutions L351D and L368E (numbering according to the EU numbering), said method further comprising the step of culturing said cell and allowing for expression of said nucleic acid sequences and harvesting said antibody or variant thereof from the culture.

20. The antibody or variant thereof of claim 1, wherein the antibody comprises:
a variable domain that can bind to an extracellular part of LAG-3 which comprises a heavy chain variable region that comprises the amino acid sequence of the heavy chain variable region according to any one of SEQ ID NO: 73, 74, 78, 79, 81, having at most 15 amino acid insertions, deletions, substitutions or a combination thereof, and
a variable domain that can bind to an extracellular part of PD-1 which comprises a heavy chain variable region that comprises the amino acid sequence of the heavy chain variable region according to SEQ ID NO: 56, having at most 15 amino acid insertions, deletions, substitutions or a combination thereof.

21. The antibody or variant thereof of claim 1, wherein the antibody comprises:
a variable domain that can bind to an extracellular part of LAG-3 which comprises a heavy chain variable region that comprises the amino acid sequence of the heavy chain variable region according to any one of SEQ ID NO: 73, 74, 78, 79, 81, having at most 15 amino acid insertions, deletions, substitutions or a combination thereof, and
a variable domain that can bind to an extracellular part of PD-1 which comprises a heavy chain variable region that comprises the amino acid sequence of the heavy chain variable region according to SEQ ID NO: 51, having at most 15, amino acid insertions, deletions, substitutions or a combination thereof.

22. The method according to claim 18, wherein the common light chain is the rearranged germline human kappa light chain IgVκ1-39*01/IGJκ1*01.

* * * * *

SEQUENCE LISTING

```
<160> NUMBER OF SEQ ID NOS: 155

<210> SEQ ID NO 1
<211> LENGTH: 288
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: DOMAIN
<222> LOCATION: (21)..(170)
<223> OTHER INFORMATION: ECD
<220> FEATURE:
<221> NAME/KEY: DOMAIN
<222> LOCATION: (171)..(191)
<223> OTHER INFORMATION: TM
<220> FEATURE:
<221> NAME/KEY: DOMAIN
<222> LOCATION: (192)..(288)
<223> OTHER INFORMATION: Intracellular tail

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
```

```
                    195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 2
<211> LENGTH: 288
<212> TYPE: PRT
<213> ORGANISM: Macaca fascicularis
<220> FEATURE:
<221> NAME/KEY: SIGNAL
<222> LOCATION: (1)..(20)
<220> FEATURE:
<221> NAME/KEY: DOMAIN
<222> LOCATION: (21)..(170)
<223> OTHER INFORMATION: ECD
<220> FEATURE:
<221> NAME/KEY: DOMAIN
<222> LOCATION: (171)..(191)
<223> OTHER INFORMATION: TM
<220> FEATURE:
<221> NAME/KEY: DOMAIN
<222> LOCATION: (192)..(288)
<223> OTHER INFORMATION: Intracellular tail

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Ala Pro Thr Phe Ser Pro Ala Leu Leu Leu Val Thr Glu Gly Asp
        35                  40                  45

Asn Ala Thr Phe Thr Cys Ser Phe Ser Asn Ala Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Arg Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205
```

-continued

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285

<210> SEQ ID NO 3
<211> LENGTH: 525
<212> TYPE: PRT
<213> ORGANISM: Homo sapiens
<220> FEATURE:
<221> NAME/KEY: SIGNAL
<222> LOCATION: (1)..(22)
<220> FEATURE:
<221> NAME/KEY: DOMAIN
<222> LOCATION: (23)..(450)
<223> OTHER INFORMATION: ECD
<220> FEATURE:
<221> NAME/KEY: DOMAIN
<222> LOCATION: (451)..(471)
<223> OTHER INFORMATION: TM
<220> FEATURE:
<221> NAME/KEY: DOMAIN
<222> LOCATION: (472)..(525)
<223> OTHER INFORMATION: Intracellular tail

<400> SEQUENCE: 3

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

```
Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
            245                 250                 255

Leu Thr Val Leu Gly Leu Glu Pro Pro Thr Pro Leu Thr Val Tyr Ala
        260                 265                 270

Gly Ala Gly Ser Arg Val Gly Leu Pro Cys Arg Leu Pro Ala Gly Val
    275                 280                 285

Gly Thr Arg Ser Phe Leu Thr Ala Lys Trp Thr Pro Pro Gly Gly Gly
290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
            325                 330                 335

Leu Gln Glu Gln Gln Leu Asn Ala Thr Val Thr Leu Ala Ile Ile Thr
        340                 345                 350

Val Thr Pro Lys Ser Phe Gly Ser Pro Gly Ser Leu Gly Lys Leu Leu
    355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
            405                 410                 415

Gly Glu Arg Leu Leu Gly Ala Ala Val Tyr Phe Thr Glu Leu Ser Ser
        420                 425                 430

Pro Gly Ala Gln Arg Ser Gly Arg Ala Pro Gly Ala Leu Pro Ala Gly
    435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Pro Glu Pro Glu Pro
        500                 505                 510

Glu Pro Glu Pro Glu Pro Glu Pro Glu Gln Leu
    515                 520                 525

<210> SEQ ID NO 4
<211> LENGTH: 525
<212> TYPE: PRT
<213> ORGANISM: Rattus norvegicus
<220> FEATURE:
<221> NAME/KEY: SIGNAL
<222> LOCATION: (1)..(22)
<220> FEATURE:
<221> NAME/KEY: DOMAIN
<222> LOCATION: (23)..(442)
<223> OTHER INFORMATION: ECD
<220> FEATURE:
<221> NAME/KEY: DOMAIN
<222> LOCATION: (443)..(463)
<223> OTHER INFORMATION: TM
<220> FEATURE:
<221> NAME/KEY: DOMAIN
<222> LOCATION: (464)..(525)
<223> OTHER INFORMATION: Intracellular tail
```

<400> SEQUENCE: 4

```
Met Arg Gln Asp Leu Phe Leu Asp Leu Leu Leu Gln Leu Leu Trp
1               5                   10                  15

Glu Ala Pro Val Val Ser Ser Gly Pro Gly Lys Glu Leu Ser Val Val
            20                  25                  30

Trp Ala Gln Glu Gly Ala Pro Val His Leu Pro Cys Ser Leu Glu Phe
        35                  40                  45

Pro His Leu Asp Pro Asn Phe Leu Arg Arg Gly Trp Val Thr Trp Gln
    50                  55                  60

His Arg Pro Asp Ser Asp Gln Pro Ala Ser Ile Pro Ala Leu Asp Leu
65                  70                  75                  80

Leu Gln Gly Met Pro Ser Thr Arg Arg His Pro Pro His Arg Tyr Thr
                85                  90                  95

Val Leu Ser Val Ala Pro Gly Gly Leu Arg Ser Gly Arg Gln Pro Leu
            100                 105                 110

Leu Ser His Val Gln Leu Glu Lys Arg Gly Pro Gln Arg Gly Asp Phe
        115                 120                 125

Ser Leu Trp Leu Arg Pro Ala Thr Arg Lys Asp Ala Gly Glu Tyr His
    130                 135                 140

Ala Phe Val Arg Leu Pro Asp Arg Asp Phe Ser Cys Ser Leu Arg Leu
145                 150                 155                 160

Arg Val Gly Gln Ala Ser Met Ile Ala Ser Pro Pro Gly Thr Leu Lys
                165                 170                 175

Pro Ser Asp Trp Val Ile Leu Asn Cys Ser Phe Ser Arg Pro Asp Arg
            180                 185                 190

Pro Val Ser Val His Trp Phe Gln Gly Gln Ser Arg Val Pro Val His
        195                 200                 205

Asn Ser Pro Arg His Tyr Leu Ala Glu Ser Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Gln Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Val Val Gly Thr Pro Ser Leu Leu
        275                 280                 285

Ile Ala Lys Trp Thr Pro Pro Gly Gly Gly Pro Glu Leu Pro Val Thr
    290                 295                 300

Gly Lys Ser Gly Asn Phe Thr Leu Gln Leu Glu Asn Val Gly Arg Ala
305                 310                 315                 320

Gln Ala Gly Thr Tyr Thr Cys Ser Ile His Leu Gln Gly Arg Gln Leu
                325                 330                 335

Ser Ala Ala Val Thr Leu Ala Val Ile Thr Val Thr Pro Lys Ser Phe
            340                 345                 350

Gly Leu Pro Gly Ser Pro Gln Lys Leu Leu Cys Glu Val Val Pro Ala
        355                 360                 365

Ser Gly Glu Gly Arg Phe Val Trp Arg Pro Leu Ser Asp Leu Ser Arg
    370                 375                 380

Ser Ser Leu Gly Pro Val Leu Glu Leu Gln Glu Ala Lys Leu Leu Ala
385                 390                 395                 400

Glu Gln Trp Gln Cys Gln Leu Tyr Glu Gly Gln Lys Leu Leu Gly Ala
                405                 410                 415
```

```
Thr Val Tyr Thr Ala Glu Ser Ser Gly Ala Trp Ser Ala Lys Arg
            420                 425                 430

Ile Ser Gly Asp Leu Lys Gly His Leu Phe Leu Ser Leu Ile Leu
            435                 440                 445

Gly Ala Leu Ala Leu Phe Leu Leu Val Thr Gly Ala Phe Gly Phe His
450                 455                 460

Leu Trp Arg Arg Gln Leu Leu Arg Arg Phe Ser Ala Leu Glu His
465                 470                 475                 480

Gly Ile Arg Pro Pro Val Gln Ser Lys Ile Glu Leu Glu Arg
                485                 490                 495

Glu Pro Glu Thr Glu Met Glu Pro Glu Thr Glu Pro Asp Pro Glu Pro
            500                 505                 510

Gln Pro Glu Pro Glu Leu Glu Pro Glu Ser Arg Gln Leu
            515                 520                 525

<210> SEQ ID NO 5
<211> LENGTH: 533
<212> TYPE: PRT
<213> ORGANISM: Macaca mulatta
<220> FEATURE:
<221> NAME/KEY: SIGNAL
<222> LOCATION: (1)..(22)
<220> FEATURE:
<221> NAME/KEY: DOMAIN
<222> LOCATION: (23)..(450)
<223> OTHER INFORMATION: ECD
<220> FEATURE:
<221> NAME/KEY: DOMAIN
<222> LOCATION: (451)..(471)
<223> OTHER INFORMATION: TM
<220> FEATURE:
<221> NAME/KEY: DOMAIN
<222> LOCATION: (472)..(533)
<223> OTHER INFORMATION: Intracellular tail

<400> SEQUENCE: 5

Met Trp Glu Ala Gln Phe Leu Gly Leu Leu Phe Leu Gln Pro Leu Trp
1               5                   10                  15

Val Ala Pro Val Lys Pro Pro Gln Pro Gly Ala Glu Ile Ser Val Val
            20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
            50                  55                  60

His Gln Pro Asp Ser Gly Pro Pro Ala Pro Ala Pro Gly His Pro Pro
65                  70                  75                  80

Ala Pro Gly His Arg Pro Ala Ala Pro Tyr Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
130                 135                 140

Gly Glu Tyr Arg Ala Thr Val His Leu Arg Asp Arg Ala Leu Ser Cys
145                 150                 155                 160

Arg Leu Arg Leu Arg Val Gly Gln Ala Ser Met Thr Ala Ser Pro Pro
                165                 170                 175

Gly Ser Leu Arg Thr Ser Asp Trp Val Ile Leu Asn Cys Ser Phe Ser
```

```
                180                 185                 190
Arg Pro Asp Arg Pro Ala Ser Val His Trp Phe Arg Ser Arg Gly Gln
            195                 200                 205

Gly Arg Val Pro Val Gln Gly Ser Pro His His Leu Ala Glu Ser
        210                 215                 220

Phe Leu Phe Leu Pro His Val Gly Pro Met Asp Ser Gly Leu Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Ala Thr Pro Leu Thr Val Tyr Ala
            260                 265                 270

Gly Ala Gly Ser Arg Val Glu Leu Pro Cys Arg Leu Pro Pro Ala Val
        275                 280                 285

Gly Thr Gln Ser Phe Leu Thr Ala Lys Trp Ala Pro Pro Gly Gly Gly
        290                 295                 300

Pro Asp Leu Leu Val Ala Gly Asp Asn Gly Asp Phe Thr Leu Arg Leu
305                 310                 315                 320

Glu Asp Val Ser Gln Ala Gln Ala Gly Thr Tyr Ile Cys His Ile Arg
                325                 330                 335

Leu Gln Gly Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Ala Ser Gly Gln Glu His Phe Val Trp Ser Pro
        370                 375                 380

Leu Asn Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu His Gln
                405                 410                 415

Gly Glu Thr Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
        435                 440                 445

His Leu Pro Leu Phe Leu Ile Leu Gly Val Leu Phe Leu Leu Leu Leu
        450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Leu Glu Pro Glu Pro
            500                 505                 510

Glu Leu Glu Arg Glu Leu Gly Pro Glu Pro Glu Pro Gly Pro Glu Pro
        515                 520                 525

Glu Pro Glu Gln Leu
    530

<210> SEQ ID NO 6
<211> LENGTH: 521
<212> TYPE: PRT
<213> ORGANISM: Mus musculus

<400> SEQUENCE: 6

Met Arg Glu Asp Leu Leu Gly Phe Leu Leu Leu Gly Leu Leu Trp
1               5                   10                  15
```

Glu Ala Pro Val Val Ser Ser Gly Pro Gly Lys Glu Leu Pro Val Val
                    20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu

```
                    435                 440                 445
Gly Ala Leu Ser Leu Phe Leu Leu Val Ala Gly Ala Phe Gly Phe His
    450                 455                 460

Trp Trp Arg Lys Gln Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Gly Pro Glu Pro Gly Pro Glu Pro
                500                 505                 510

Gln Leu Glu Pro Glu Pro Arg Gln Leu
            515                 520

<210> SEQ ID NO 7
<211> LENGTH: 525
<212> TYPE: PRT
<213> ORGANISM: Artificial Sequence
<220> FEATURE:
<223> OTHER INFORMATION: mouse/human LAG chimeric insert

<400> SEQUENCE: 7

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Ile Ala Ser Pro Ser
                165                 170                 175

Gly Val Leu Lys Leu Ser Asp Trp Val Leu Leu Asn Cys Ser Phe Ser
            180                 185                 190

Arg Pro Asp Arg Pro Val Ser Val His Trp Phe Gln Gly Gln Asn Arg
    195                 200                 205

Val Pro Val Tyr Asn Ser Pro Arg His Phe Leu Ala Glu Thr Phe Leu
    210                 215                 220

Leu Leu Pro Gln Val Ser Pro Leu Asp Ser Gly Thr Trp Gly Cys Val
225                 230                 235                 240

Leu Thr Tyr Arg Asp Gly Phe Asn Val Ser Ile Thr Tyr Asn Leu Lys
                245                 250                 255

Val Leu Gly Leu Glu Pro Val Ala Pro Leu Thr Val Tyr Ala Ala Glu
            260                 265                 270

Gly Ser Arg Val Glu Leu Pro Cys His Leu Pro Pro Gly Val Gly Thr
```

```
                275                 280                 285
Pro Ser Leu Leu Ile Ala Lys Trp Thr Pro Gly Gly Pro Glu
290                 295                 300

Leu Pro Val Ala Gly Lys Ser Gly Asn Phe Thr His Leu Glu Ala
305                 310                 315                 320

Val Gly Leu Ala Gln Ala Gly Thr Tyr Thr Cys Ser Ile His Leu Gln
                325                 330                 335

Gly Gln Gln Leu Asn Ala Thr Val Thr Leu Ala Val Ile Thr Val Thr
            340                 345                 350

Pro Lys Ser Phe Gly Leu Pro Gly Ser Arg Gly Lys Leu Leu Cys Glu
        355                 360                 365

Val Thr Pro Ala Ser Gly Lys Glu Arg Phe Val Trp Arg Pro Leu Asn
370                 375                 380

Asn Leu Ser Arg Ser Cys Pro Gly Pro Val Leu Glu Ile Gln Glu Ala
385                 390                 395                 400

Arg Leu Leu Ala Glu Arg Trp Gln Cys Gln Leu Tyr Glu Gly Gln Arg
                405                 410                 415

Leu Leu Gly Ala Thr Val Tyr Ala Ala Glu Ser Ser Ser Gly Ala His
            420                 425                 430

Ser Ala Arg Arg Ile Ser Gly Asp Leu Lys Gly Gly His Leu Val Leu
        435                 440                 445

Val Leu Ile Leu Gly Ala Leu Ser Leu Phe Leu Leu Val Ala Gly Ala
        450                 455                 460

Phe Gly Phe His Trp Trp Arg Lys Gln Leu Leu Leu Arg Arg Phe Ser
465                 470                 475                 480

Ala Leu Glu His Gly Ile Gln Pro Phe Pro Ala Gln Arg Lys Ile Glu
                485                 490                 495

Glu Leu Glu Arg Glu Leu Glu Thr Glu Met Gly Gln Glu Pro Glu Pro
            500                 505                 510

Glu Pro Glu Pro Gln Leu Glu Pro Glu Pro Arg Gln Leu
        515                 520                 525

<210> SEQ ID NO 8
<211> LENGTH: 523
<212> TYPE: PRT
<213> ORGANISM: Artificial Sequence
<220> FEATURE:
<223> OTHER INFORMATION: mouse/human LAG chimeric insert

<400> SEQUENCE: 8

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
```

```
            115                 120                 125
Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Thr Ala Ser Pro Pro Gly Ser Leu Arg
                165                 170                 175

Ala Ser Asp Trp Val Ile Leu Asn Cys Ser Phe Ser Arg Pro Asp Arg
            180                 185                 190

Pro Ala Ser Val His Trp Phe Arg Asn Arg Gly Gln Gly Arg Val Pro
        195                 200                 205

Val Arg Glu Ser Pro His His His Leu Ala Glu Ser Phe Leu Phe Leu
    210                 215                 220

Pro Gln Val Ser Pro Met Asp Ser Gly Pro Trp Gly Cys Ile Leu Thr
225                 230                 235                 240

Tyr Arg Asp Gly Phe Asn Val Ser Ile Thr Tyr Asn Leu Lys Val Leu
                245                 250                 255

Gly Leu Glu Pro Val Ala Pro Leu Thr Val Tyr Ala Ala Glu Gly Ser
            260                 265                 270

Arg Val Glu Leu Pro Cys His Leu Pro Pro Gly Val Gly Thr Pro Ser
        275                 280                 285

Leu Leu Ile Ala Lys Trp Thr Pro Pro Gly Gly Gly Pro Glu Leu Pro
    290                 295                 300

Val Ala Gly Lys Ser Gly Asn Phe Thr Leu His Leu Glu Ala Val Gly
305                 310                 315                 320

Leu Ala Gln Ala Gly Thr Tyr Thr Cys Ser Ile His Leu Gln Gly Gln
                325                 330                 335

Gln Leu Asn Ala Thr Val Thr Leu Ala Val Ile Thr Val Thr Pro Lys
            340                 345                 350

Ser Phe Gly Leu Pro Gly Ser Arg Gly Lys Leu Leu Cys Glu Val Thr
        355                 360                 365

Pro Ala Ser Gly Lys Glu Arg Phe Val Trp Arg Pro Leu Asn Asn Leu
    370                 375                 380

Ser Arg Ser Cys Pro Gly Pro Val Leu Glu Ile Gln Glu Ala Arg Leu
385                 390                 395                 400

Leu Ala Glu Arg Trp Gln Cys Gln Leu Tyr Glu Gly Gln Arg Leu Leu
                405                 410                 415

Gly Ala Thr Val Tyr Ala Ala Glu Ser Ser Ser Gly Ala His Ser Ala
            420                 425                 430

Arg Arg Ile Ser Gly Asp Leu Lys Gly Gly His Leu Val Leu Val Leu
        435                 440                 445

Ile Leu Gly Ala Leu Ser Leu Phe Leu Leu Val Ala Gly Ala Phe Gly
    450                 455                 460

Phe His Trp Trp Arg Lys Gln Leu Leu Leu Arg Arg Phe Ser Ala Leu
465                 470                 475                 480

Glu His Gly Ile Gln Pro Phe Pro Ala Gln Arg Lys Ile Glu Glu Leu
                485                 490                 495

Glu Arg Glu Leu Glu Thr Glu Met Gly Gln Glu Pro Glu Pro Glu Pro
            500                 505                 510

Glu Pro Gln Leu Glu Pro Glu Pro Arg Gln Leu
        515                 520

<210> SEQ ID NO 9
```

<211> LENGTH: 521
<212> TYPE: PRT
<213> ORGANISM: Artificial Sequence
<220> FEATURE:
<223> OTHER INFORMATION: mouse/human LAG chimeric insert

<400> SEQUENCE: 9

```
Met Arg Glu Asp Leu Leu Gly Phe Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Met Tyr Asn Leu Thr Val Leu Gly Leu
                245                 250                 255

Glu Pro Pro Thr Pro Leu Thr Val Tyr Ala Gly Ala Gly Ser Arg Val
            260                 265                 270

Gly Leu Pro Cys Arg Leu Pro Ala Gly Val Gly Thr Arg Ser Phe Leu
        275                 280                 285

Thr Ala Lys Trp Thr Pro Pro Gly Gly Gly Pro Asp Leu Leu Val Thr
    290                 295                 300

Gly Asp Asn Gly Asp Phe Thr Leu Arg Leu Glu Asp Val Ser Gln Ala
305                 310                 315                 320

Gln Ala Gly Thr Tyr Thr Cys His Ile His Leu Gln Glu Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380
```

```
Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
            405                 410                 415

Thr Val Tyr Ala Ala Glu Ser Ser Ser Gly Ala His Ser Ala Arg Arg
        420                 425                 430

Ile Ser Gly Asp Leu Lys Gly Gly His Leu Val Leu Val Leu Ile Leu
            435                 440                 445

Gly Ala Leu Ser Leu Phe Leu Leu Val Ala Gly Ala Phe Gly Phe His
        450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
        515                 520
```

```
<210> SEQ ID NO 10
<211> LENGTH: 522
<212> TYPE: PRT
<213> ORGANISM: Artificial Sequence
<220> FEATURE:
<223> OTHER INFORMATION: mouse/human LAG chimeric insert

<400> SEQUENCE: 10
```

```
Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
                100                 105                 110

His Pro His Val Gln Leu Glu Glu Arg Gly Leu Gln Arg Gly Asp Phe
            115                 120                 125

Ser Leu Trp Leu Arg Pro Ala Leu Arg Thr Asp Ala Gly Glu Tyr His
        130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
                180                 185                 190

Pro Val Ser Val His Trp Phe Gln Gly Gln Asn Arg Val Pro Val Tyr
            195                 200                 205

Asn Ser Pro Arg His Phe Leu Ala Glu Thr Phe Leu Leu Leu Pro Gln
        210                 215                 220
```

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
            245                 250                 255

Glu Pro Val Ala Pro Leu Thr Val Tyr Ala Ala Glu Gly Ser Arg Val
        260                 265                 270

Glu Leu Pro Cys His Leu Pro Pro Gly Val Gly Thr Pro Ser Leu Leu
    275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
            325                 330                 335

Asn Ala Thr Val Thr Leu Ala Ile Ile Thr Val Thr Pro Lys Ser Phe
        340                 345                 350

Gly Ser Pro Gly Ser Leu Gly Lys Leu Leu Cys Glu Val Thr Pro Val
    355                 360                 365

Ser Gly Gln Glu Arg Phe Val Trp Ser Ser Leu Asp Thr Pro Ser Gln
370                 375                 380

Arg Ser Phe Ser Gly Pro Trp Leu Glu Ala Gln Glu Ala Gln Leu Leu
385                 390                 395                 400

Ser Gln Pro Trp Gln Cys Gln Leu Tyr Gln Gly Glu Arg Leu Leu Gly
            405                 410                 415

Ala Thr Val Tyr Ala Ala Glu Ser Ser Ser Gly Ala His Ser Ala Arg
        420                 425                 430

Arg Ile Ser Gly Asp Leu Lys Gly Gly His Leu Val Leu Val Leu Ile
    435                 440                 445

Leu Gly Ala Leu Ser Leu Phe Leu Leu Val Ala Gly Ala Phe Gly Phe
450                 455                 460

His Trp Trp Arg Lys Gln Leu Leu Leu Arg Arg Phe Ser Ala Leu Glu
465                 470                 475                 480

His Gly Ile Gln Pro Phe Pro Ala Gln Arg Lys Ile Glu Glu Leu Glu
            485                 490                 495

Arg Glu Leu Glu Thr Glu Met Gly Gln Glu Pro Glu Pro Glu Pro Glu
        500                 505                 510

Pro Gln Leu Glu Pro Glu Pro Arg Gln Leu
    515                 520

<210> SEQ ID NO 11
<211> LENGTH: 523
<212> TYPE: PRT
<213> ORGANISM: Artificial Sequence
<220> FEATURE:
<223> OTHER INFORMATION: mouse/human LAG chimeric insert

<400> SEQUENCE: 11

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

```
His Gln Pro Asp Ser Gly Gln Pro Thr Pro Ile Pro Ala Leu Asp Leu
 65                  70                  75                  80

His Gln Gly Met Pro Ser Pro Arg Gln Pro Ala Pro Gly Arg Tyr Thr
                 85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Ile Ile Thr Val Thr Pro Lys Ser Phe
            340                 345                 350

Gly Ser Pro Gly Ser Leu Gly Lys Leu Leu Cys Glu Val Thr Pro Val
        355                 360                 365

Ser Gly Gln Glu Arg Phe Val Trp Ser Ser Leu Asp Thr Pro Ser Gln
    370                 375                 380

Arg Ser Phe Ser Gly Pro Trp Leu Glu Ala Gln Glu Ala Gln Leu Leu
385                 390                 395                 400

Ser Gln Pro Trp Gln Cys Gln Leu Tyr Gln Gly Glu Arg Leu Leu Gly
                405                 410                 415

Ala Ala Val Tyr Phe Thr Glu Leu Ser Ser Pro Gly Ala Gln Arg Ser
            420                 425                 430

Gly Arg Ala Pro Gly Ala Leu Pro Ala Gly His Leu Val Leu Val Leu
        435                 440                 445

Ile Leu Gly Ala Leu Ser Leu Phe Leu Leu Val Ala Gly Ala Phe Gly
    450                 455                 460

Phe His Trp Trp Arg Lys Gln Leu Leu Leu Arg Arg Phe Ser Ala Leu
465                 470                 475                 480
```

```
Glu His Gly Ile Gln Pro Phe Pro Ala Gln Arg Lys Ile Glu Glu Leu
            485                 490                 495

Glu Arg Glu Leu Glu Thr Glu Met Gly Gln Glu Pro Glu Pro Glu Pro
        500                 505                 510

Glu Pro Gln Leu Glu Pro Glu Pro Arg Gln Leu
        515                 520

<210> SEQ ID NO 12
<211> LENGTH: 9
<212> TYPE: PRT
<213> ORGANISM: Artificial Sequence
<220> FEATURE:
<223> OTHER INFORMATION: LAG-3 Fab arm

<400> SEQUENCE: 12

Ile Pro Leu Thr Gly Glu Phe Asp Tyr
1               5

<210> SEQ ID NO 13
<211> LENGTH: 16
<212> TYPE: PRT
<213> ORGANISM: Artificial Sequence
<220> FEATURE:
<223> OTHER INFORMATION: LAG-3 Fab arm

<400> SEQUENCE: 13

Gly Gly Thr Tyr Tyr Tyr Gly Ser Gly Ser Tyr Tyr Thr Leu Asp Tyr
1               5                   10                  15

<210> SEQ ID NO 14
<211> LENGTH: 10
<212> TYPE: PRT
<213> ORGANISM: Artificial Sequence
<220> FEATURE:
<223> OTHER INFORMATION: LAG-3 Fab arm

<400> SEQUENCE: 14

Asp Gly Asp Asn Trp Asp Val Phe Asp Ile
1               5                   10

<210> SEQ ID NO 15
<211> LENGTH: 9
<212> TYPE: PRT
<213> ORGANISM: Artificial Sequence
<220> FEATURE:
<223> OTHER INFORMATION: LAG-3 Fab arm

<400> SEQUENCE: 15

Glu Arg Gly Trp Asp Val Phe Asp Ile
1               5

<210> SEQ ID NO 16
<211> LENGTH: 16
<212> TYPE: PRT
<213> ORGANISM: Artificial Sequence
<220> FEATURE:
<223> OTHER INFORMATION: LAG-3 Fab arm

<400> SEQUENCE: 16

Gly Gly Thr Tyr Tyr Tyr Gly Ser Gly Ser Tyr Tyr Thr Leu Asp Phe
1               5                   10                  15

<210> SEQ ID NO 17
<211> LENGTH: 10
<212> TYPE: PRT
<213> ORGANISM: Artificial Sequence
```

```
<220> FEATURE:
<223> OTHER INFORMATION: LAG-3 Fab arm

<400> SEQUENCE: 17

Asp Gly Ser Gly Trp Asp Asp Phe Asp Tyr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: LAG-3 Fab arm

<400> SEQUENCE: 18

Glu Pro Asn Trp Gly Val Tyr Phe Asp Tyr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: LAG-3 Fab arm

<400> SEQUENCE: 19

Asp Arg Glu Val Gly Ala Ile Tyr Tyr Phe Asp Tyr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: LAG-3 Fab arm

<400> SEQUENCE: 20

Glu Arg Asp Ile Gly Ser Leu Tyr Tyr Phe Asp Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: LAG-3 Fab arm

<400> SEQUENCE: 21

Asp Arg Glu Met Phe Thr Leu Tyr Phe Phe Asp Gln
1               5                   10

<210> SEQ ID NO 22
<211> LENGTH: 16
<212> TYPE: PRT
<213> ORGANISM: Artificial Sequence
<220> FEATURE:
<223> OTHER INFORMATION: LAG-3 Fab arm

<400> SEQUENCE: 22

Asp Ser Thr Tyr Tyr Tyr Thr Ser Gly Ser Tyr Ser Val Phe Asp Tyr
1               5                   10                  15

<210> SEQ ID NO 23
<211> LENGTH: 17
<212> TYPE: PRT
<213> ORGANISM: Artificial Sequence
<220> FEATURE:
```

```
<223> OTHER INFORMATION: LAG-3 Fab arm

<400> SEQUENCE: 23

Val Pro Ala Ala Ala Thr Pro Ser Gly Thr Tyr Tyr Trp Ile Phe Asp
1               5                   10                  15

Leu

<210> SEQ ID NO 24
<211> LENGTH: 15
<212> TYPE: PRT
<213> ORGANISM: Artificial Sequence
<220> FEATURE:
<223> OTHER INFORMATION: LAG-3 Fab arm

<400> SEQUENCE: 24

Asp Thr Ser Thr Trp Gln Arg Gly Gly Tyr Lys Ala Phe Asp Tyr
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: LAG-3 Fab arm

<400> SEQUENCE: 25

Asp Arg Gly Tyr Asp Tyr Ser Gly Ser Tyr His Asn Trp Phe Asp Pro
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: LAG-3 Fab arm

<400> SEQUENCE: 26

Arg Pro Gly Pro Ala Leu Gly Asp Leu Asp Ser
1               5                   10

<210> SEQ ID NO 27
<211> LENGTH: 15
<212> TYPE: PRT
<213> ORGANISM: Artificial Sequence
<220> FEATURE:
<223> OTHER INFORMATION: LAG-3 Fab arm

<400> SEQUENCE: 27

Asp Thr Gly Gln Ser Trp Ser Asn Tyr Tyr His Ala Phe Asp Tyr
1               5                   10                  15

<210> SEQ ID NO 28
<211> LENGTH: 214
<212> TYPE: PRT
<213> ORGANISM: Artificial Sequence
<220> FEATURE:
<223> OTHER INFORMATION: common light chain

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 321
<212> TYPE: DNA
<213> ORGANISM: Artificial Sequence
<220> FEATURE:
<223> OTHER INFORMATION: common light chain variable domain
<220> FEATURE:
<221> NAME/KEY: CDS
<222> LOCATION: (1)..(321)

<400> SEQUENCE: 29 gac atc cag atg acc cag tct cca tcc tcc ctg tct gca tct gta gga      48
Asp Ile Gln Met Thr Gln Ser Pro Ser Ser Leu Ser Ala Ser Val Gly
 1               5                  10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
                20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
            35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
 65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                         321
Thr Phe Gly Gln Gly Thr Lys Val Glu Ile Lys
            100                 105

<210> SEQ ID NO 30
<211> LENGTH: 107
<212> TYPE: PRT
```

```
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 31
<211> LENGTH: 324
<212> TYPE: DNA
<213> ORGANISM: Artificial Sequence
<220> FEATURE:
<223> OTHER INFORMATION: common light chain constant domain
<220> FEATURE:
<221> NAME/KEY: CDS
<222> LOCATION: (1)..(324)

<400> SEQUENCE: 31 cga act gtg gct gca cca tct gtc ttc atc ttc ccg cca tct gat gag    48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc    96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa   144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc   192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag   240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg   288
Lys His Lys Val Tyr Ala Cys Glu Val Thr His Gln Gly Leu Ser Ser
                85                  90                  95 ccc gtc aca aag agc ttc aac agg gga gag tgt tag                   324
Pro Val Thr Lys Ser Phe Asn Arg Gly Glu Cys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Arg Thr Val Ala Ala Pro Ser Val Phe Ile Phe Pro Pro Ser Asp Glu
```

```
              1               5                  10                  15
            Gln Leu Lys Ser Gly Thr Ala Ser Val Val Cys Leu Leu Asn Asn Phe
                           20                  25                  30

Tyr Pro Arg Glu Ala Lys Val Gln Trp Lys Val Asp Asn Ala Leu Gln
                           35                  40                  45

Ser Gly Asn Ser Gln Glu Ser Val Thr Glu Gln Asp Ser Lys Asp Ser
                           50                  55                  60

Thr Tyr Ser Leu Ser Ser Thr Leu Thr Leu Ser Lys Ala Asp Tyr Glu
             65                  70                  75                  80

Lys His Lys Val Tyr Ala Cys Glu Val Thr His Gln Gly Leu Ser Ser
                           85                  90                  95

Pro Val Thr Lys Ser Phe Asn Arg Gly Glu Cys
                           100                 105

<210> SEQ ID NO 33
<211> LENGTH: 108
<212> TYPE: PRT
<213> ORGANISM: Artificial Sequence
<220> FEATURE:
<223> OTHER INFORMATION: IGKV1-39/jk5 common light chain variable domain

<400> SEQUENCE: 33

Asp Ile Gln Met Thr Gln Ser Pro Ser Ser Leu Ser Ala Ser Val Gly
             1               5                  10                  15

Asp Arg Val Thr Ile Thr Cys Arg Ala Ser Gln Ser Ile Ser Ser Tyr
                           20                  25                  30

Leu Asn Trp Tyr Gln Gln Lys Pro Gly Lys Ala Pro Lys Leu Leu Ile
                           35                  40                  45

Tyr Ala Ala Ser Ser Leu Gln Ser Gly Val Pro Ser Arg Phe Ser Gly
                           50                  55                  60

Ser Gly Ser Gly Thr Asp Phe Thr Leu Thr Ile Ser Ser Leu Gln Pro
             65                  70                  75                  80

Glu Asp Phe Ala Thr Tyr Tyr Cys Gln Gln Ser Tyr Ser Thr Pro Pro
                           85                  90                  95

Ile Thr Phe Gly Gln Gly Thr Arg Leu Glu Ile Lys
                           100                 105

<210> SEQ ID NO 34
<211> LENGTH: 95
<212> TYPE: PRT
<213> ORGANISM: Artificial Sequence
<220> FEATURE:
<223> OTHER INFORMATION: V-region IGKV1-39A

<400> SEQUENCE: 34

Asp Ile Gln Met Thr Gln Ser Pro Ser Ser Leu Ser Ala Ser Val Gly
             1               5                  10                  15

Asp Arg Val Thr Ile Thr Cys Arg Ala Ser Gln Ser Ile Ser Ser Tyr
                           20                  25                  30

Leu Asn Trp Tyr Gln Gln Lys Pro Gly Lys Ala Pro Lys Leu Leu Ile
                           35                  40                  45

Tyr Ala Ala Ser Ser Leu Gln Ser Gly Val Pro Ser Arg Phe Ser Gly
                           50                  55                  60

Ser Gly Ser Gly Thr Asp Phe Thr Leu Thr Ile Ser Ser Leu Gln Pro
             65                  70                  75                  80

Glu Asp Phe Ala Thr Tyr Tyr Cys Gln Gln Ser Tyr Ser Thr Pro
                           85                  90                  95
```

<210> SEQ ID NO 35
<211> LENGTH: 294
<212> TYPE: DNA
<213> ORGANISM: Artificial Sequence
<220> FEATURE:
<223> OTHER INFORMATION: CH1 region
<220> FEATURE:
<221> NAME/KEY: CDS
<222> LOCATION: (1)..(294)

<400> SEQUENCE: 35

```
gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtc gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aga gtt                                                             294
Arg Val
```

<210> SEQ ID NO 36
<211> LENGTH: 98
<212> TYPE: PRT
<213> ORGANISM: Artificial Sequence
<220> FEATURE:
<223> OTHER INFORMATION: Synthetic Construct

<400> SEQUENCE: 36

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val
```

<210> SEQ ID NO 37
<211> LENGTH: 45
<212> TYPE: DNA
<213> ORGANISM: Artificial Sequence
<220> FEATURE:
<223> OTHER INFORMATION: hinge region
<220> FEATURE:
<221> NAME/KEY: CDS

<222> LOCATION: (1)..(45)

<400> SEQUENCE: 37

| gag | ccc | aaa | tct | tgt | gac | aaa | act | cac | aca | tgc | cca | ccg | tgc | cca | 45 |
|-----|-----|-----|-----|-----|-----|-----|-----|-----|-----|-----|-----|-----|-----|-----|-----|
| Glu | Pro | Lys | Ser | Cys | Asp | Lys | Thr | His | Thr | Cys | Pro | Pro | Cys | Pro | |
| 1   |     |     |     | 5   |     |     |     |     | 10  |     |     |     |     | 15  | |

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

Glu Pro Lys Ser Cys Asp Lys Thr His Thr Cys Pro Pro Cys Pro
1               5                   10                  15

<210> SEQ ID NO 39
<211> LENGTH: 330
<212> TYPE: DNA
<213> ORGANISM: Artificial Sequence
<220> FEATURE:
<223> OTHER INFORMATION: CH2 region
<220> FEATURE:
<221> NAME/KEY: CDS
<222> LOCATION: (1)..(330)

<400> SEQUENCE: 39

| gca | cct | gaa | ctc | ctg | ggg | gga | ccg | tca | gtc | ttc | ctc | ttc | ccc | cca | aaa | 48 |
|-----|-----|-----|-----|-----|-----|-----|-----|-----|-----|-----|-----|-----|-----|-----|-----|----|
| Ala | Pro | Glu | Leu | Leu | Gly | Gly | Pro | Ser | Val | Phe | Leu | Phe | Pro | Pro | Lys | |
| 1   |     |     |     | 5   |     |     |     |     | 10  |     |     |     |     | 15  |     | |

| ccc | aag | gac | acc | ctc | atg | atc | tcc | cgg | acc | cct | gag | gtc | aca | tgc | gtg | 96 |
|-----|-----|-----|-----|-----|-----|-----|-----|-----|-----|-----|-----|-----|-----|-----|-----|----|
| Pro | Lys | Asp | Thr | Leu | Met | Ile | Ser | Arg | Thr | Pro | Glu | Val | Thr | Cys | Val | |
|     |     |     | 20  |     |     |     |     | 25  |     |     |     |     | 30  |     |     | |

| gtg | gtg | gac | gtg | agc | cac | gaa | gac | cct | gag | gtc | aag | ttc | aac | tgg | tac | 144 |
|-----|-----|-----|-----|-----|-----|-----|-----|-----|-----|-----|-----|-----|-----|-----|-----|-----|
| Val | Val | Asp | Val | Ser | His | Glu | Asp | Pro | Glu | Val | Lys | Phe | Asn | Trp | Tyr | |
|     |     |     |     | 35  |     |     |     |     | 40  |     |     |     |     | 45  |     | |

| gtg | gac | ggc | gtg | gag | gtg | cat | aat | gcc | aag | aca | aag | ccg | cgg | gag | gag | 192 |
|-----|-----|-----|-----|-----|-----|-----|-----|-----|-----|-----|-----|-----|-----|-----|-----|-----|
| Val | Asp | Gly | Val | Glu | Val | His | Asn | Ala | Lys | Thr | Lys | Pro | Arg | Glu | Glu | |
|     | 50  |     |     |     |     | 55  |     |     |     |     | 60  |     |     |     |     | |

| cag | tac | aac | agc | acg | tac | cgt | gtg | gtc | agc | gtc | ctc | acc | gtc | ctg | cac | 240 |
|-----|-----|-----|-----|-----|-----|-----|-----|-----|-----|-----|-----|-----|-----|-----|-----|-----|
| Gln | Tyr | Asn | Ser | Thr | Tyr | Arg | Val | Val | Ser | Val | Leu | Thr | Val | Leu | His | |
| 65  |     |     |     |     | 70  |     |     |     |     | 75  |     |     |     |     | 80  | |

| cag | gac | tgg | ctg | aat | ggc | aag | gag | tac | aag | tgc | aag | gtc | tcc | aac | aaa | 288 |
|-----|-----|-----|-----|-----|-----|-----|-----|-----|-----|-----|-----|-----|-----|-----|-----|-----|
| Gln | Asp | Trp | Leu | Asn | Gly | Lys | Glu | Tyr | Lys | Cys | Lys | Val | Ser | Asn | Lys | |
|     |     |     |     | 85  |     |     |     |     | 90  |     |     |     |     | 95  |     | |

| gcc | ctc | cca | gcc | ccc | atc | gag | aaa | acc | atc | tcc | aaa | gcc | aaa |     |     | 330 |
|-----|-----|-----|-----|-----|-----|-----|-----|-----|-----|-----|-----|-----|-----|-----|-----|-----|
| Ala | Leu | Pro | Ala | Pro | Ile | Glu | Lys | Thr | Ile | Ser | Lys | Ala | Lys |     |     | |
|     |     |     | 100 |     |     |     |     | 105 |     |     |     |     | 110 |     |     | |

<210> SEQ ID NO 40
<211> LENGTH: 110
<212> TYPE: PRT
<213> ORGANISM: Artificial Sequence
<220> FEATURE:
<223> OTHER INFORMATION: Synthetic Construct

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr

```
                35                  40                  45
Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 41
<211> LENGTH: 330
<212> TYPE: DNA
<213> ORGANISM: Artificial Sequence
<220> FEATURE:
<223> OTHER INFORMATION: CH2 region containing L235G and G236R silencing
      substitutions
<220> FEATURE:
<221> NAME/KEY: CDS
<222> LOCATION: (1)..(330)

<400> SEQUENCE: 41 gca cct gaa ctc ggc agg gga ccg tca gtc ttc ctc ttc ccc cca aaa      48
Ala Pro Glu Leu Gly Arg Gly Pro Ser Val Phe Leu Phe Pro Pro Lys
1               5                   10                  15 ccc aag gac acc ctc atg atc tcc cgg acc cct gag gtc aca tgc gtg     96
Pro Lys Asp Thr Leu Met Ile Ser Arg Thr Pro Glu Val Thr Cys Val
            20                  25                  30 gtg gtg gac gtg agc cac gaa gac cct gag gtc aag ttc aac tgg tac    144
Val Val Asp Val Ser His Glu Asp Pro Glu Val Lys Phe Asn Trp Tyr
        35                  40                  45 gtg gac ggc gtg gag gtg cat aat gcc aag aca aag ccg cgg gag gag    192
Val Asp Gly Val Glu Val His Asn Ala Lys Thr Lys Pro Arg Glu Glu
    50                  55                  60 cag tac aac agc acg tac cgt gtg gtc agc gtc ctc acc gtc ctg cac    240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa    288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa            330
Ala Leu Pro Ala Pro Ile Glu Lys Thr Ile Ser Lys Ala Lys
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Synthetic Construct

<400> SEQUENCE: 42

Ala Pro Glu Leu Gly Arg Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
```

```
                65                  70                  75                  80
Gln Asp Trp Leu Asn Gly Lys Glu Tyr Lys Cys Lys Val Ser Asn Lys
                    85                  90                  95

Ala Leu Pro Ala Pro Ile Glu Lys Thr Ile Ser Lys Ala Lys
                100                 105                 110

<210> SEQ ID NO 43
<211> LENGTH: 321
<212> TYPE: DNA
<213> ORGANISM: Artificial Sequence
<220> FEATURE:
<223> OTHER INFORMATION: CH3 domain containing substitutions L351K and
      T366K
<220> FEATURE:
<221> NAME/KEY: CDS
<222> LOCATION: (1)..(321)

<400> SEQUENCE: 43 ggg cag ccc cga gaa cca cag gtg tac acc aag ccc cca tcc cgg gag      48
Gly Gln Pro Arg Glu Pro Gln Val Tyr Thr Lys Pro Pro Ser Arg Glu
1               5                  10                  15 gag atg acc aag aac cag gtc agc ctg aag tgc ctg gtc aaa ggc ttc      96
Glu Met Thr Lys Asn Gln Val Ser Leu Lys Cys Leu Val Lys Gly Phe
            20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
            100                 105

<210> SEQ ID NO 44
<211> LENGTH: 106
<212> TYPE: PRT
<213> ORGANISM: Artificial Sequence
<220> FEATURE:
<223> OTHER INFORMATION: Synthetic Construct

<400> SEQUENCE: 44

Gly Gln Pro Arg Glu Pro Gln Val Tyr Thr Lys Pro Pro Ser Arg Glu
1               5                  10                  15

Glu Met Thr Lys Asn Gln Val Ser Leu Lys Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

-continued

<210> SEQ ID NO 45
<211> LENGTH: 321
<212> TYPE: DNA
<213> ORGANISM: Artificial Sequence
<220> FEATURE:
<223> OTHER INFORMATION: CH3 domain containing substitutions L351D and L368E
<220> FEATURE:
<221> NAME/KEY: CDS
<222> LOCATION: (1)..(321)

<400> SEQUENCE: 45

```
ggg cag ccc cga gaa cca cag gtg tac acc gac ccc cca tcc cgg gag      48
Gly Gln Pro Arg Glu Pro Gln Val Tyr Thr Asp Pro Pro Ser Arg Glu
1               5                   10                  15 gag atg acc aag aac cag gtc agc ctg acc tgc gag gtc aaa ggc ttc      96
Glu Met Thr Lys Asn Gln Val Ser Leu Thr Cys Glu Val Lys Gly Phe
            20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
            100                 105
```

<210> SEQ ID NO 46
<211> LENGTH: 106
<212> TYPE: PRT
<213> ORGANISM: Artificial Sequence
<220> FEATURE:
<223> OTHER INFORMATION: Synthetic Construct

<400> SEQUENCE: 46

Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 47
<211> LENGTH: 121
<212> TYPE: PRT

<213> ORGANISM: Artificial Sequence
<220> FEATURE:
<223> OTHER INFORMATION: MF6076

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Thr Asp Ser Leu Gly Phe Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Ser Ala Asn Phe Asn Pro Ser Leu Lys
    50                  55                  60

Ser Arg Val Thr Met Ser Ile Asp Thr Ser Asn Asn Gln Phe Ser Leu
65                  70                  75                  80

Lys Leu Arg Ser Val Thr Ala Ala Asp Thr Ala Val Tyr Phe Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 48
<211> LENGTH: 121
<212> TYPE: PRT
<213> ORGANISM: Artificial Sequence
<220> FEATURE:
<223> OTHER INFORMATION: MF6226

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Gly Tyr Tyr
            20                  25                  30

Phe Trp Ser Trp Ile Arg Gln Pro Pro Gly Lys Gly Leu Glu Trp Ile
        35                  40                  45

Gly Tyr Val Tyr Tyr Ser Gly Ser Asn Asn Leu Asn Pro Ser Leu Lys
    50                  55                  60

Ser Arg Val Thr Leu Ser Val Asp Thr Ser Lys Asn Gln Phe Ser Leu
65                  70                  75                  80

Arg Leu Asn Ser Met Thr Ala Ala Asp Thr Ala Val Tyr Tyr Cys Ala
                85                  90                  95

Arg Gly Gly Tyr Ser Gly Tyr Gly Gly Asp Ser Phe Asp Leu Trp Gly
            100                 105                 110

Gln Gly Thr Thr Val Thr Val Ser Ser
        115                 120

<210> SEQ ID NO 49
<211> LENGTH: 121
<212> TYPE: PRT
<213> ORGANISM: Artificial Sequence
<220> FEATURE:
<223> OTHER INFORMATION: MF6236

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Tyr Tyr
            20                  25                  30

Phe Trp Ser Trp Ile Arg Gln Pro Pro Gly Lys Gly Leu Glu Trp Ile
            35                  40                  45

Gly Tyr Ile Tyr Tyr Ser Gly Ser Thr Asn Phe Asn Pro Ser Leu Lys
        50                  55                  60

Ser Arg Val Thr Met Ser Val Asp Thr Ser Lys Asn Gln Phe Ser Leu
65                  70                  75                  80

Asn Leu Arg Ser Val Thr Thr Ala Asp Thr Ala Val Tyr Tyr Cys Ala
                85                  90                  95

Arg Gly Gly Tyr Thr Gly His Gly Gly Asp Trp Phe Asp Pro Trp Gly
            100                 105                 110

Gln Gly Thr Leu Val Thr Val Ser Ser
            115                 120

<210> SEQ ID NO 50
<211> LENGTH: 120
<212> TYPE: PRT
<213> ORGANISM: Artificial Sequence
<220> FEATURE:
<223> OTHER INFORMATION: MF6256

<400> SEQUENCE: 50

Glu Val Gln Leu Val Gln Ser Gly Ala Glu Val Lys Lys Pro Gly Ser
1               5                   10                  15

Ser Met Lys Val Ser Cys Lys Ala Ser Gly Gly Thr Phe Ser Ser Tyr
            20                  25                  30

Val Ile Ser Trp Val Arg Gln Ala Pro Gly Gln Gly Leu Glu Trp Met
            35                  40                  45

Gly Met Ile Ile Pro Val Phe Asp Thr Ser Tyr Glu Lys Lys Phe
        50                  55                  60

Gln Gly Arg Ile Thr Ile Ile Ala Asp Lys Ser Thr Ser Thr Val Tyr
65                  70                  75                  80

Leu Glu Leu Ser Ser Leu Arg Ser Glu Asp Ala Ala Val Tyr Tyr Cys
                85                  90                  95

Ala Arg Gly Thr Val Glu Ala Thr Leu Leu Phe Asp Phe Trp Gly Gln
            100                 105                 110

Gly Thr Leu Val Thr Val Ser Ser
        115                 120

<210> SEQ ID NO 51
<211> LENGTH: 120
<212> TYPE: PRT
<213> ORGANISM: Artificial Sequence
<220> FEATURE:
<223> OTHER INFORMATION: MF6930

<400> SEQUENCE: 51

Glu Val Gln Leu Val Gln Ser Gly Ala Glu Val Lys Lys Pro Gly Ser
1               5                   10                  15

Ser Met Lys Val Ser Cys Lys Ala Ser Gly Gly Thr Phe Ser Asn Tyr
            20                  25                  30

Val Ile Ser Trp Val Arg Gln Ala Pro Gly Gln Gly Leu Glu Trp Met
            35                  40                  45

Gly Met Ile Ile Pro Val Phe Glu Thr Ala Thr Tyr Glu Lys Lys Phe
        50                  55                  60

Gln Gly Arg Val Thr Ile Ile Ala Asp Lys Ser Thr Ser Thr Val Tyr
65                  70                  75                  80

Met Glu Leu Ser Ser Leu Arg Ser Glu Asp Ala Ala Val Tyr Tyr Cys

-continued

```
                85                  90                  95
Ala Arg Gly Thr Val Glu Ala Thr Leu Leu Phe Asp Tyr Trp Gly Gln
            100                 105                 110
Gly Thr Leu Val Thr Val Ser Ser
        115                 120

<210> SEQ ID NO 52
<211> LENGTH: 120
<212> TYPE: PRT
<213> ORGANISM: Artificial Sequence
<220> FEATURE:
<223> OTHER INFORMATION: MF6932

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Met Ile Ile Pro Phe Phe Asp Thr Ala Asn Tyr Ala Gln Lys Phe
    50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Ser Ala Thr Leu Val Phe Asp Tyr Trp Gly Gln
            100                 105                 110

Gly Thr Leu Val Thr Val Ser Ser
        115                 120

<210> SEQ ID NO 53
<211> LENGTH: 120
<212> TYPE: PRT
<213> ORGANISM: Artificial Sequence
<220> FEATURE:
<223> OTHER INFORMATION: MF6935

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Val Ile Ser Trp Val Arg Gln Ala Pro Gly Gln Gly Leu Glu Trp Met
        35                  40                  45

Gly Met Ile Ile Pro Ile Phe Asp Thr Ala Asn Tyr Ala Gln Lys Phe
    50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Val Tyr Tyr Cys
                85                  90                  95

Ala Arg Gly Thr Val Ser Gly Thr Leu Val Phe Asp Tyr Trp Gly Gln
            100                 105                 110

Gly Thr Leu Val Thr Val Ser Ser
        115                 120

<210> SEQ ID NO 54
<211> LENGTH: 120
```

-continued

```
<212> TYPE: PRT
<213> ORGANISM: Artificial Sequence
<220> FEATURE:
<223> OTHER INFORMATION: MF6936

<400> SEQUENCE: 54

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Val Ile Asn Trp Val Arg Gln Ala Pro Gly Gln Gly Leu Glu Trp Met
        35                  40                  45

Gly Met Ile Ile Pro Val Phe Asp Thr Thr Ser Tyr Glu Arg Lys Phe
    50                  55                  60

Gln Gly Arg Val Thr Ile Thr Ala Asp Lys Ser Thr Ser Thr Ala Tyr
65                  70                  75                  80

Met Glu Leu Thr Ser Leu Arg Ser Glu Asp Thr Ala Val Tyr Tyr Cys
                85                  90                  95

Ala Arg Gly Thr Val Gly Ala Thr Leu Leu Phe Asp Asn Trp Gly Gln
            100                 105                 110

Gly Thr Leu Val Thr Val Ser Ser
        115                 120

<210> SEQ ID NO 55
<211> LENGTH: 121
<212> TYPE: PRT
<213> ORGANISM: Artificial Sequence
<220> FEATURE:
<223> OTHER INFORMATION: MF6972

<400> SEQUENCE: 55

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Phe Trp Ser Trp Ile Arg Gln Pro Pro Gly Lys Gly Leu Glu Trp Ile
        35                  40                  45

Gly Tyr Ile Ile Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Ser Gly Tyr Gly Gly Asp Asp Phe Asp Ile Trp Gly
            100                 105                 110

Gln Gly Thr Met Val Thr Val Ser Ser
        115                 120

<210> SEQ ID NO 56
<211> LENGTH: 118
<212> TYPE: PRT
<213> ORGANISM: Artificial Sequence
<220> FEATURE:
<223> OTHER INFORMATION: MF6974

<400> SEQUENCE: 56

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Ser Tyr
```

```
                    20                  25                  30

Ala Met Ser Trp Val Arg Gln Ala Pro Gly Lys Gly Leu Glu Trp Val
            35                  40                  45

Ser Thr Ile Ser Gly Gly Gly Ala Asn Ile Tyr Tyr Ala Asp Ser Val
        50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Ser Gly Tyr Phe Asp Val Trp Gly Gln Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: MF6982

<400> SEQUENCE: 57

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Gly Gly Thr Asn Ile Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Gly Asp Thr Ala Val Tyr Tyr Cys
                85                  90                  95

Ala Ser Pro Tyr Gly Ser Gly Tyr Leu Asp Val Trp Gly Gln Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: MF7100

<400> SEQUENCE: 58

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Thr His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Met Tyr Tyr Cys
                85                  90                  95

Ala Arg Glu Arg Gly Trp Asp Val Phe Asp Ile Trp Gly Gln Gly Thr
            100                 105                 110

Leu Val Thr Val Ser Ser
        115

<210> SEQ ID NO 59
<211> LENGTH: 117
<212> TYPE: PRT
<213> ORGANISM: Artificial Sequence
<220> FEATURE:
<223> OTHER INFORMATION: MF7111

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Asp Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Lys Tyr Asn Pro Ser Leu Lys
50                  55                  60

Asn Arg Val Thr Ile Ser Val Asp Thr Ser Lys Ser Gln Phe Ser Leu
65                  70                  75                  80

Lys Leu Thr Ser Val Thr Ala Ala Asp Thr Ala Val Tyr Tyr Cys Ala
                85                  90                  95

Arg Ile Pro Leu Thr Gly Glu Phe Asp Tyr Trp Ala Gln Gly Thr Leu
            100                 105                 110

Val Thr Val Ser Ser
        115

<210> SEQ ID NO 60
<211> LENGTH: 119
<212> TYPE: PRT
<213> ORGANISM: Artificial Sequence
<220> FEATURE:
<223> OTHER INFORMATION: MF7116

<400> SEQUENCE: 60

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr His Gly Ser Asp Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asp Asn Trp Asp Val Phe Asp Ile Trp Gly Gln Gly
            100                 105                 110

Thr Leu Val Thr Val Ser Ser
        115

<210> SEQ ID NO 61

```
<211> LENGTH: 126
<212> TYPE: PRT
<213> ORGANISM: Artificial Sequence
<220> FEATURE:
<223> OTHER INFORMATION: MF7118

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Gly Val Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Val Pro Ala Ala Ala Thr Pro Ser Gly Thr Tyr Tyr Trp Ile
            100                 105                 110

Phe Asp Leu Trp Gly Arg Gly Thr Leu Val Thr Val Ser Ser
        115                 120                 125

<210> SEQ ID NO 62
<211> LENGTH: 119
<212> TYPE: PRT
<213> ORGANISM: Artificial Sequence
<220> FEATURE:
<223> OTHER INFORMATION: MF7134

<400> SEQUENCE: 62

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Asn
            20                  25                  30

Ala Leu Asn Trp Val Arg Gln Ala Pro Gly Gln Gly Leu Glu Trp Met
        35                  40                  45

Gly Trp Ile Asn Thr His Thr Gly Asn Pro Thr Tyr Ala Gln Gly Phe
    50                  55                  60

Ile Gly Arg Phe Val Phe Ser Leu Asp Thr Ser Val Ser Thr Ala Tyr
65                  70                  75                  80

Leu Gln Ile Arg Ser Leu Lys Ala Glu Asp Thr Ala Val Tyr Tyr Cys
                85                  90                  95

Ala Arg Glu Pro Asn Trp Gly Val Tyr Phe Asp Tyr Trp Gly Gln Gly
            100                 105                 110

Thr Leu Val Thr Val Ser Ser
        115

<210> SEQ ID NO 63
<211> LENGTH: 125
<212> TYPE: PRT
<213> ORGANISM: Artificial Sequence
<220> FEATURE:
<223> OTHER INFORMATION: MF7136

<400> SEQUENCE: 63

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Ser Thr Tyr Tyr Tyr Thr Ser Gly Ser Tyr Ser Val Phe
            100                 105                 110

Asp Tyr Trp Gly Gln Gly Thr Leu Val Thr Val Ser Ser
        115                 120                 125

<210> SEQ ID NO 64
<211> LENGTH: 125
<212> TYPE: PRT
<213> ORGANISM: Artificial Sequence
<220> FEATURE:
<223> OTHER INFORMATION: MF7137

<400> SEQUENCE: 64

Gln Val Gln Leu Val Gln Ser Gly Ala Glu Val Lys Arg Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Ser Asp Pro Glu His Gly Glu Thr Val Asp Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Thr Thr Gly Gly Thr Tyr Tyr Tyr Gly Ser Gly Ser Tyr Tyr Thr Leu
            100                 105                 110

Asp Phe Trp Gly Gln Gly Thr Leu Val Thr Val Ser Ser
        115                 120                 125

<210> SEQ ID NO 65
<211> LENGTH: 121
<212> TYPE: PRT
<213> ORGANISM: Artificial Sequence
<220> FEATURE:
<223> OTHER INFORMATION: MF7142

<400> SEQUENCE: 65

Gln Val Gln Leu Val Gln Ser Gly Ala Glu Val Arg Lys Pro Gly Ser
1               5                   10                  15

Ser Val Met Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Pro Tyr Tyr Gly Gln Arg Phe
 50                  55                  60

Gln Gly Arg Val Thr Ile Thr Ala Asp Lys Ser Thr Asn Thr Val Phe
 65                  70                  75                  80
```

Met Glu Leu Ser Ser Leu Arg Ser Glu Asp Thr Ala Met Tyr Phe Cys
                85                  90                  95

Ala Arg Glu Arg Asp Ile Gly Ser Leu Tyr Tyr Phe Asp Ser Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: MF7146

<400> SEQUENCE: 66

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Phe Ile Thr Trp Val Arg Gln Ala Pro Gly Gln Gly Leu Glu Trp Met
        35                  40                  45

Gly Gly Ile Ile Pro Ser Phe Gly Thr Gly Asn Tyr Ala Gln Lys Phe
    50                  55                  60

Gln Gly Arg Val Ala Ile Thr Ala Asp Lys Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Val Arg Asp Arg Glu Val Gly Ala Ile Tyr Tyr Phe Asp Tyr Trp Gly
            100                 105                 110

Gln Gly Thr Met Val Thr Val Ser Ser
        115                 120

<210> SEQ ID NO 67
<211> LENGTH: 125
<212> TYPE: PRT
<213> ORGANISM: Artificial Sequence
<220> FEATURE:
<223> OTHER INFORMATION: MF7165

<400> SEQUENCE: 67

Gln Val Gln Leu Val Gln Ser Gly Ala Glu Val Arg Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Ala Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Thr Gly Gly Thr Tyr Tyr Tyr Gly Ser Gly Ser Tyr Tyr Thr Leu
            100                 105                 110

Asp Tyr Trp Gly Gln Gly Thr Leu Val Thr Val Ser Ser
        115                 120                 125

```
<210> SEQ ID NO 68
<211> LENGTH: 125
<212> TYPE: PRT
<213> ORGANISM: Artificial Sequence
<220> FEATURE:
<223> OTHER INFORMATION: MF7167

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Lys Asp Arg Gly Tyr Asp Tyr Ser Gly Ser Tyr His Asn Trp Phe
            100                 105                 110

Asp Pro Trp Gly Gln Gly Thr Leu Val Thr Val Ser Ser
        115                 120                 125

<210> SEQ ID NO 69
<211> LENGTH: 121
<212> TYPE: PRT
<213> ORGANISM: Artificial Sequence
<220> FEATURE:
<223> OTHER INFORMATION: MF7185

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Asn Tyr
            20                  25                  30

Ala Phe Ser Trp Val Arg Gln Ala Pro Gly Gln Gly Leu Glu Trp Met
        35                  40                  45

Gly Gly Ile Ile Pro Ile Phe Gly Ser Thr Asn Tyr Ala Gln Ser Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Glu Met Gly Thr Leu Tyr Phe Phe Asp Gln Trp Gly
            100                 105                 110

Gln Gly Thr Thr Val Thr Val Ser Ser
        115                 120

<210> SEQ ID NO 70
<211> LENGTH: 124
<212> TYPE: PRT
<213> ORGANISM: Artificial Sequence
<220> FEATURE:
<223> OTHER INFORMATION: MF7443

<400> SEQUENCE: 70

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Ser Thr Trp Gln Arg Gly Gly Tyr Lys Ala Phe Asp
            100                 105                 110

Tyr Trp Gly Gln Gly Thr Leu Val Thr Val Ser Ser
            115                 120

<210> SEQ ID NO 71
<211> LENGTH: 124
<212> TYPE: PRT
<213> ORGANISM: Artificial Sequence
<220> FEATURE:
<223> OTHER INFORMATION: MF7444

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Gly Gln Ser Trp Ser Asn Tyr Tyr His Ala Phe Asp
            100                 105                 110

Tyr Trp Gly Gln Gly Thr Leu Val Thr Val Ser Ser
            115                 120

<210> SEQ ID NO 72
<211> LENGTH: 120
<212> TYPE: PRT
<213> ORGANISM: Artificial Sequence
<220> FEATURE:
<223> OTHER INFORMATION: MF7515

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr

```
            65                  70                  75                  80
Met Glu Leu Arg Ser Leu Arg Ser Asp Asp Thr Ala Val Tyr Tyr Cys
                    85                  90                  95

Ala Arg Arg Pro Gly Pro Ala Leu Gly Asp Leu Asp Ser Trp Gly Gln
                100                 105                 110

Gly Thr Leu Val Thr Val Ser Ser
        115                 120

<210> SEQ ID NO 73
<211> LENGTH: 119
<212> TYPE: PRT
<213> ORGANISM: Artificial Sequence
<220> FEATURE:
<223> OTHER INFORMATION: MF7518

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Asp Gly Ser Gly Trp Asp Asp Phe Asp Tyr Trp Gly Gln Gly
                100                 105                 110

Thr Leu Val Thr Val Ser Ser
        115

<210> SEQ ID NO 74
<211> LENGTH: 122
<212> TYPE: PRT
<213> ORGANISM: Artificial Sequence
<220> FEATURE:
<223> OTHER INFORMATION: MF7096

<400> SEQUENCE: 74

Gln Val Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Tyr
                20                  25                  30

Ser Trp Ser Trp Ile Arg Gln Pro Pro Gly Lys Gly Leu Glu Trp Ile
            35                  40                  45

Gly Tyr Ile Asp Tyr Ser Gly Ser Thr Asn Tyr Asn Pro Ser Leu Lys
        50                  55                  60

Ser Arg Val Thr Ile Ser Val Asp Thr Ser Lys Thr Gln Phe Ser Leu
65                  70                  75                  80

Lys Leu Ser Ser Val Ser Ala Ala Asp Thr Ala Val Tyr Tyr Cys Ala
                    85                  90                  95

Lys Asp Leu Leu Tyr Lys Trp Asn Tyr Val Glu Gly Phe Asp Ile Trp
                100                 105                 110

Gly Gln Gly Thr Thr Val Thr Val Ser Ser
        115                 120
```

-continued

<210> SEQ ID NO 75
<211> LENGTH: 122
<212> TYPE: PRT
<213> ORGANISM: Artificial Sequence
<220> FEATURE:
<223> OTHER INFORMATION: MF7097

<400> SEQUENCE: 75

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Ser Trp Ser Trp Ile Arg Gln Pro Pro Gly Lys Gly Leu Glu Trp Ile
        35                  40                  45
Gly Tyr Ile Asp Tyr Ser Gly Thr Thr Asn Phe Asn Pro Ser Leu Lys
    50                  55                  60
Ser Arg Val Thr Ile Ser Val Asp Thr Ser Lys Thr Gln Phe Ser Leu
65                  70                  75                  80
Lys Leu Ser Ser Val Ser Ala Ala Asp Thr Ala Val Tyr Tyr Cys Ala
                85                  90                  95
Lys Asp Leu Leu Tyr Lys Trp Asn Tyr Val Glu Gly Phe Asp Ile Trp
            100                 105                 110
Gly Gln Gly Thr Met Val Thr Val Ser Ser
        115                 120
```

<210> SEQ ID NO 76
<211> LENGTH: 121
<212> TYPE: PRT
<213> ORGANISM: Artificial Sequence
<220> FEATURE:
<223> OTHER INFORMATION: MF7106

<400> SEQUENCE: 76

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Lys Tyr
            20                  25                  30
Val Val Ser Trp Val Arg Gln Ala Pro Gly Gln Gly Phe Asp Trp Met
        35                  40                  45
Gly Gly Ile Ile Pro Met Phe Gly Thr Ala Asn Tyr Ala Gln Met Phe
    50                  55                  60
Gln Gly Arg Val Thr Ile Thr Ala Asp Lys Ser Thr Ser Thr Val Asn
65                  70                  75                  80
Met Glu Leu Ser Ser Leu Arg Ser Glu Asp Thr Ala Val Tyr Tyr Cys
                85                  90                  95
Val Arg Asp Lys Ala Val Ala Gly Leu Tyr Tyr Phe Asp Ser Trp Gly
            100                 105                 110
Gln Gly Thr Leu Val Thr Val Ser Ser
        115                 120
```

<210> SEQ ID NO 77
<211> LENGTH: 121
<212> TYPE: PRT
<213> ORGANISM: Artificial Sequence
<220> FEATURE:
<223> OTHER INFORMATION: MF7120

<400> SEQUENCE: 77

```
Gln Val Gln Leu Val Gln Ser Gly Ala Glu Val Lys Lys Pro Gly Ser
```

```
            1               5                   10                  15
Ser Val Lys Val Ser Cys Lys Ala Ser Gly Asp Thr Phe Ser Thr Tyr
                20                  25                  30

Ala Ile Asn Trp Ile Arg Gln Ala Pro Gly Gln Gly Leu Glu Trp Met
                35                  40                  45

Gly Gly Ile Ile Pro Ile Phe Gly Thr Ala Tyr Tyr Ala Gln Glu Phe
            50                  55                  60

Gln Asp Arg Val Thr Ile Thr Ala Asp Lys Ser Thr Ser Thr Gly Tyr
65                  70                  75                  80

Met Glu Met Ser Ser Leu Ile Ser Glu Asp Thr Ala Val Tyr Tyr Cys
                85                  90                  95

Ala Arg Glu Arg Glu Leu Gly Ala Leu Tyr Ala Phe Asp Ile Trp Gly
                100                 105                 110

Gln Gly Thr Met Val Thr Val Ser Ser
            115                 120

<210> SEQ ID NO 78
<211> LENGTH: 121
<212> TYPE: PRT
<213> ORGANISM: Artificial Sequence
<220> FEATURE:
<223> OTHER INFORMATION: MF7133

<400> SEQUENCE: 78

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Ala Ile Ser Trp Val Arg Gln Val Pro Gly Gln Gly Leu Glu Trp Met
                35                  40                  45

Gly Gly Ile Ile Pro Leu Phe Asp Thr Ala Lys Asn Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Glu Thr Gly Thr Leu Tyr Tyr Phe Asp Tyr Trp Gly
                100                 105                 110

Gln Gly Thr Leu Val Thr Val Ser Ser
            115                 120

<210> SEQ ID NO 79
<211> LENGTH: 121
<212> TYPE: PRT
<213> ORGANISM: Artificial Sequence
<220> FEATURE:
<223> OTHER INFORMATION: MF7139

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Phe
                20                  25                  30

Ala Phe Ser Trp Val Arg Gln Ala Pro Gly Gln Gly Leu Glu Trp Met
                35                  40                  45

Gly Gly Ile Ile Pro Met Phe Asp Thr Ala Lys Tyr Ala Gln Lys Phe
            50                  55                  60
```

```
Gln Gly Arg Val Thr Ile Ile Ala Asp Lys Ser Thr Asn Thr Ala Tyr
 65                  70                  75                  80

Met Asp Leu Asn Ser Leu Arg Ser Glu Asp Thr Ala Val Tyr Tyr Cys
                 85                  90                  95

Val Arg Asp Arg Ala Ile Gly Thr Leu Tyr Tyr Phe Asp Tyr Trp Gly
            100                 105                 110

Gln Gly Thr Leu Val Thr Val Ser Ser
        115                 120
```

<210> SEQ ID NO 80
<211> LENGTH: 121
<212> TYPE: PRT
<213> ORGANISM: Artificial Sequence
<220> FEATURE:
<223> OTHER INFORMATION: MF7144

<400> SEQUENCE: 80

```
Gln Val Gln Leu Val Gln Ser Gly Ala Glu Val Arg Lys Pro Gly Ser
  1               5                  10                  15

Ser Val Met Val Ser Cys Lys Ala Ser Gly Gly Thr Phe Ser Thr Tyr
                 20                  25                  30

Ala Ile Asn Trp Leu Arg Gln Ala Pro Gly Gln Gly Leu Glu Trp Met
             35                  40                  45

Gly Gly Ile Ile Pro Ile Phe Gly Thr Pro Tyr Tyr Gly Gln Arg Phe
     50                  55                  60

Gln Gly Arg Val Thr Ile Thr Ala Asp Lys Ser Thr Asn Thr Val Phe
 65                  70                  75                  80

Met Glu Leu Ser Ser Leu Arg Ser Glu Asp Thr Ala Ile Tyr Tyr Cys
                 85                  90                  95

Ala Arg Asp Arg Asp Ser Gly Gly Leu Tyr Tyr Phe Asp Ser Trp Gly
            100                 105                 110

Gln Gly Thr Leu Val Thr Val Ser Ser
        115                 120
```

<210> SEQ ID NO 81
<211> LENGTH: 121
<212> TYPE: PRT
<213> ORGANISM: Artificial Sequence
<220> FEATURE:
<223> OTHER INFORMATION: MF7524

<400> SEQUENCE: 81

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Ser Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Ser Ile Leu Ala Ala Gln Met Trp Gly Asp Ile Trp Gly
            100                 105                 110

Gln Gly Thr Leu Val Thr Val Ser Ser
        115                 120
```

<210> SEQ ID NO 82
<211> LENGTH: 127
<212> TYPE: PRT
<213> ORGANISM: Artificial Sequence
<220> FEATURE:
<223> OTHER INFORMATION: tetanus toxin specific VH

<400> SEQUENCE: 82

```
Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
        115                 120                 125
```

<210> SEQ ID NO 83
<211> LENGTH: 13
<212> TYPE: PRT
<213> ORGANISM: Artificial Sequence
<220> FEATURE:
<223> OTHER INFORMATION: CDR3 MF6076

<400> SEQUENCE: 83

```
Gly Gly Tyr Thr Gly Tyr Gly Gly Asp Trp Phe Asp Pro
1               5                   10
```

<210> SEQ ID NO 84
<211> LENGTH: 9
<212> TYPE: PRT
<213> ORGANISM: Artificial Sequence
<220> FEATURE:
<223> OTHER INFORMATION: CDR3 MF6974

<400> SEQUENCE: 84

```
Pro Tyr Gly Ser Gly Tyr Phe Asp Val
1               5
```

<210> SEQ ID NO 85
<211> LENGTH: 11
<212> TYPE: PRT
<213> ORGANISM: Artificial Sequence
<220> FEATURE:
<223> OTHER INFORMATION: CDR3 MF6930

<400> SEQUENCE: 85

```
Gly Thr Val Glu Ala Thr Leu Leu Phe Asp Tyr
1               5                   10
```

<210> SEQ ID NO 86
<211> LENGTH: 13
<212> TYPE: PRT
<213> ORGANISM: Artificial Sequence

```
<220> FEATURE:
<223> OTHER INFORMATION: CDR3 MF6227

<400> SEQUENCE: 86

Gly Gly Tyr Ser Gly Tyr Gly Gly Asp Asp Phe Asp Ile
1               5                   10

<210> SEQ ID NO 87
<211> LENGTH: 11
<212> TYPE: PRT
<213> ORGANISM: Artificial Sequence
<220> FEATURE:
<223> OTHER INFORMATION: MF6935

<400> SEQUENCE: 87

Gly Thr Val Ser Gly Thr Leu Val Phe Asp Tyr
1               5                   10

<210> SEQ ID NO 88
<211> LENGTH: 11
<212> TYPE: PRT
<213> ORGANISM: Artificial Sequence
<220> FEATURE:
<223> OTHER INFORMATION: CDR3 MF6932

<400> SEQUENCE: 88

Gly Thr Val Ser Ala Thr Leu Val Phe Asp Tyr
1               5                   10

<210> SEQ ID NO 89
<211> LENGTH: 9
<212> TYPE: PRT
<213> ORGANISM: Artificial Sequence
<220> FEATURE:
<223> OTHER INFORMATION: CDR3 MF6983

<400> SEQUENCE: 89

Pro Tyr Asp Ser Gly Tyr Phe Asp Val
1               5

<210> SEQ ID NO 90
<211> LENGTH: 13
<212> TYPE: PRT
<213> ORGANISM: Artificial Sequence
<220> FEATURE:
<223> OTHER INFORMATION: CDR3 MF6225

<400> SEQUENCE: 90

Gly Gly Tyr Ser Gly Tyr Gly Gly Asp Ser Met Asp Val
1               5                   10

<210> SEQ ID NO 91
<211> LENGTH: 15
<212> TYPE: PRT
<213> ORGANISM: Artificial Sequence
<220> FEATURE:
<223> OTHER INFORMATION: CDR3 MF5743

<400> SEQUENCE: 91

Ala Tyr Cys Ser Gly Asn Ser Cys Tyr Thr Asp Tyr Phe Asp Tyr
1               5                   10                  15

<210> SEQ ID NO 92
<211> LENGTH: 12
<212> TYPE: PRT
<213> ORGANISM: Artificial Sequence
<220> FEATURE:
```

<223> OTHER INFORMATION: CDR3 MF7139

<400> SEQUENCE: 92

Asp Arg Ala Ile Gly Thr Leu Tyr Tyr Phe Asp Tyr
1               5                   10

<210> SEQ ID NO 93
<211> LENGTH: 12
<212> TYPE: PRT
<213> ORGANISM: Artificial Sequence
<220> FEATURE:
<223> OTHER INFORMATION: CDR3 MF7524

<400> SEQUENCE: 93

Gly Ser Ile Leu Ala Ala Gln Met Trp Gly Asp Ile
1               5                   10

<210> SEQ ID NO 94
<211> LENGTH: 12
<212> TYPE: PRT
<213> ORGANISM: Artificial Sequence
<220> FEATURE:
<223> OTHER INFORMATION: CDR3 MF7133

<400> SEQUENCE: 94

Asp Arg Glu Thr Gly Thr Leu Tyr Tyr Phe Asp Tyr
1               5                   10

<210> SEQ ID NO 95
<211> LENGTH: 12
<212> TYPE: PRT
<213> ORGANISM: Artificial Sequence
<220> FEATURE:
<223> OTHER INFORMATION: CDR3 MF7144

<400> SEQUENCE: 95

Asp Arg Asp Ser Gly Gly Leu Tyr Tyr Phe Asp Ser
1               5                   10

<210> SEQ ID NO 96
<211> LENGTH: 12
<212> TYPE: PRT
<213> ORGANISM: Artificial Sequence
<220> FEATURE:
<223> OTHER INFORMATION: CDR3 MF7142

<400> SEQUENCE: 96

Glu Arg Asp Ile Gly Ser Leu Tyr Tyr Phe Asp Ser
1               5                   10

<210> SEQ ID NO 97
<211> LENGTH: 12
<212> TYPE: PRT
<213> ORGANISM: Artificial Sequence
<220> FEATURE:
<223> OTHER INFORMATION: CDR3 MF7185

<400> SEQUENCE: 97

Asp Arg Glu Met Gly Thr Leu Tyr Phe Phe Asp Gln
1               5                   10

<210> SEQ ID NO 98
<211> LENGTH: 10
<212> TYPE: PRT
<213> ORGANISM: Artificial Sequence
<220> FEATURE:
<223> OTHER INFORMATION: CDR3 MF7518

<400> SEQUENCE: 98

Asp Gly Ser Gly Trp Asp Asp Phe Asp Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: CDR3 MF7120

<400> SEQUENCE: 99

Glu Arg Glu Leu Gly Ala Leu Tyr Ala Phe Asp Ile
1               5                   10

<210> SEQ ID NO 100
<211> LENGTH: 14
<212> TYPE: PRT
<213> ORGANISM: Artificial Sequence
<220> FEATURE:
<223> OTHER INFORMATION: CDR3 MF7097

<400> SEQUENCE: 100

Asp Leu Leu Tyr Lys Trp Asn Tyr Val Glu Gly Phe Asp Ile
1               5                   10

<210> SEQ ID NO 101
<211> LENGTH: 14
<212> TYPE: PRT
<213> ORGANISM: Artificial Sequence
<220> FEATURE:
<223> OTHER INFORMATION: CDR3 MF7096

<400> SEQUENCE: 101

Asp Leu Leu Tyr Lys Trp Asn Tyr Val Glu Gly Phe Asp Ile
1               5                   10

<210> SEQ ID NO 102
<211> LENGTH: 9
<212> TYPE: PRT
<213> ORGANISM: Artificial Sequence
<220> FEATURE:
<223> OTHER INFORMATION: CDR3 MF7111

<400> SEQUENCE: 102

Ile Pro Leu Thr Gly Glu Phe Asp Tyr
1               5

<210> SEQ ID NO 103
<211> LENGTH: 9
<212> TYPE: PRT
<213> ORGANISM: Artificial Sequence
<220> FEATURE:
<223> OTHER INFORMATION: CDR3 MF7100

<400> SEQUENCE: 103

Glu Arg Gly Trp Asp Val Phe Asp Ile
1               5

<210> SEQ ID NO 104
<211> LENGTH: 10
<212> TYPE: PRT
<213> ORGANISM: Artificial Sequence
<220> FEATURE:
<223> OTHER INFORMATION: CDR3 MF7134

<400> SEQUENCE: 104

Glu Pro Asn Trp Gly Val Tyr Phe Asp Tyr
1               5                   10

<210> SEQ ID NO 105
<211> LENGTH: 10
<212> TYPE: PRT
<213> ORGANISM: Artificial Sequence
<220> FEATURE:
<223> OTHER INFORMATION: CDR3 MF7116

<400> SEQUENCE: 105

Asp Gly Asp Asn Trp Asp Val Phe Asp Ile
1               5                   10

<210> SEQ ID NO 106
<211> LENGTH: 16
<212> TYPE: PRT
<213> ORGANISM: Artificial Sequence
<220> FEATURE:
<223> OTHER INFORMATION: CDR3 MF7137

<400> SEQUENCE: 106

Gly Gly Thr Tyr Tyr Tyr Gly Ser Gly Ser Tyr Tyr Thr Leu Asp Phe
1               5                   10                  15

<210> SEQ ID NO 107
<211> LENGTH: 12
<212> TYPE: PRT
<213> ORGANISM: Artificial Sequence
<220> FEATURE:
<223> OTHER INFORMATION: CDR3 MF7106

<400> SEQUENCE: 107

Asp Lys Ala Val Ala Gly Leu Tyr Tyr Phe Asp Ser
1               5                   10

<210> SEQ ID NO 108
<211> LENGTH: 17
<212> TYPE: PRT
<213> ORGANISM: Artificial Sequence
<220> FEATURE:
<223> OTHER INFORMATION: CDR3 MF7118

<400> SEQUENCE: 108

Val Pro Ala Ala Ala Thr Pro Ser Gly Thr Tyr Tyr Trp Ile Phe Asp
1               5                   10                  15
Leu

<210> SEQ ID NO 109
<211> LENGTH: 16
<212> TYPE: PRT
<213> ORGANISM: Artificial Sequence
<220> FEATURE:
<223> OTHER INFORMATION: CDR3 MF7167

<400> SEQUENCE: 109

Asp Arg Gly Tyr Asp Tyr Ser Gly Ser Tyr His Asn Trp Phe Asp Pro
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: CDR3 MF7444

```
<400> SEQUENCE: 110

Asp Thr Gly Gln Ser Trp Ser Asn Tyr Tyr His Ala Phe Asp Tyr
1               5                   10                  15

<210> SEQ ID NO 111
<211> LENGTH: 13
<212> TYPE: PRT
<213> ORGANISM: Artificial Sequence
<220> FEATURE:
<223> OTHER INFORMATION: CDR3 MF6226

<400> SEQUENCE: 111

Gly Gly Tyr Ser Gly Tyr Gly Gly Asp Ser Phe Asp Leu
1               5                   10

<210> SEQ ID NO 112
<211> LENGTH: 11
<212> TYPE: PRT
<213> ORGANISM: Artificial Sequence
<220> FEATURE:
<223> OTHER INFORMATION: CDR3 MF6256

<400> SEQUENCE: 112

Gly Thr Val Glu Ala Thr Leu Leu Phe Asp Phe
1               5                   10

<210> SEQ ID NO 113
<211> LENGTH: 11
<212> TYPE: PRT
<213> ORGANISM: Artificial Sequence
<220> FEATURE:
<223> OTHER INFORMATION: CDR3 MF6930

<400> SEQUENCE: 113

Gly Thr Val Glu Ala Thr Leu Leu Phe Asp Tyr
1               5                   10

<210> SEQ ID NO 114
<211> LENGTH: 14
<212> TYPE: PRT
<213> ORGANISM: Artificial Sequence
<220> FEATURE:
<223> OTHER INFORMATION: CDR3 MF7096

<400> SEQUENCE: 114

Asp Leu Leu Tyr Lys Trp Asn Tyr Val Glu Gly Phe Asp Ile
1               5                   10

<210> SEQ ID NO 115
<211> LENGTH: 14
<212> TYPE: PRT
<213> ORGANISM: Artificial Sequence
<220> FEATURE:
<223> OTHER INFORMATION: CDR3 MF7097

<400> SEQUENCE: 115

Asp Leu Leu Tyr Lys Trp Asn Tyr Val Glu Gly Phe Asp Ile
1               5                   10

<210> SEQ ID NO 116
<211> LENGTH: 12
<212> TYPE: PRT
<213> ORGANISM: Artificial Sequence
<220> FEATURE:
<223> OTHER INFORMATION: CDR3 MF7106
```

```
<400> SEQUENCE: 116

Asp Lys Ala Val Ala Gly Leu Tyr Tyr Phe Asp Ser
1               5                   10

<210> SEQ ID NO 117
<211> LENGTH: 17
<212> TYPE: PRT
<213> ORGANISM: Artificial Sequence
<220> FEATURE:
<223> OTHER INFORMATION: CDR3 MF7118

<400> SEQUENCE: 117

Val Pro Ala Ala Ala Thr Pro Ser Gly Thr Tyr Tyr Trp Ile Phe Asp
1               5                   10                  15

Leu

<210> SEQ ID NO 118
<211> LENGTH: 12
<212> TYPE: PRT
<213> ORGANISM: Artificial Sequence
<220> FEATURE:
<223> OTHER INFORMATION: CDR3 MF7120

<400> SEQUENCE: 118

Glu Arg Glu Leu Gly Ala Leu Tyr Ala Phe Asp Ile
1               5                   10

<210> SEQ ID NO 119
<211> LENGTH: 12
<212> TYPE: PRT
<213> ORGANISM: Artificial Sequence
<220> FEATURE:
<223> OTHER INFORMATION: CDR3 MF7133

<400> SEQUENCE: 119

Asp Arg Glu Thr Gly Thr Leu Tyr Tyr Phe Asp Tyr
1               5                   10

<210> SEQ ID NO 120
<211> LENGTH: 12
<212> TYPE: PRT
<213> ORGANISM: Artificial Sequence
<220> FEATURE:
<223> OTHER INFORMATION: CDR3 MF7139

<400> SEQUENCE: 120

Asp Arg Ala Ile Gly Thr Leu Tyr Tyr Phe Asp Tyr
1               5                   10

<210> SEQ ID NO 121
<211> LENGTH: 12
<212> TYPE: PRT
<213> ORGANISM: Artificial Sequence
<220> FEATURE:
<223> OTHER INFORMATION: CDR3 MF7144

<400> SEQUENCE: 121

Asp Arg Asp Ser Gly Gly Leu Tyr Tyr Phe Asp Ser
1               5                   10

<210> SEQ ID NO 122
<211> LENGTH: 12
<212> TYPE: PRT
<213> ORGANISM: Artificial Sequence
<220> FEATURE:
<223> OTHER INFORMATION: CDR3 MF7524
```

<400> SEQUENCE: 122

Gly Ser Ile Leu Ala Ala Gln Met Trp Gly Asp Ile
1               5                   10

<210> SEQ ID NO 123
<211> LENGTH: 9
<212> TYPE: PRT
<213> ORGANISM: Artificial Sequence
<220> FEATURE:
<223> OTHER INFORMATION: CDR3 MF6973

<400> SEQUENCE: 123

Pro Tyr Gly Ser Gly Tyr Phe Asp Val
1               5

<210> SEQ ID NO 124
<211> LENGTH: 9
<212> TYPE: PRT
<213> ORGANISM: Artificial Sequence
<220> FEATURE:
<223> OTHER INFORMATION: CDR3H 7111

<400> SEQUENCE: 124

Ile Pro Leu Thr Gly Glu Phe Asp Tyr
1               5

<210> SEQ ID NO 125
<211> LENGTH: 20
<212> TYPE: PRT
<213> ORGANISM: Artificial Sequence
<220> FEATURE:
<223> OTHER INFORMATION: signal peptide.

<400> SEQUENCE: 125

Met Gln Ile Pro Gln Ala Pro Trp Pro Val Val Trp Ala Val Leu Gln
1               5                   10                  15

Leu Gly Trp Arg
            20

<210> SEQ ID NO 126
<211> LENGTH: 150
<212> TYPE: PRT
<213> ORGANISM: Artificial Sequence
<220> FEATURE:
<223> OTHER INFORMATION: ECD of huPD-1

<400> SEQUENCE: 126

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

```
Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val
145                 150

<210> SEQ ID NO 127
<211> LENGTH: 21
<212> TYPE: PRT
<213> ORGANISM: Artificial Sequence
<220> FEATURE:
<223> OTHER INFORMATION: Predicted TM region

<400> SEQUENCE: 127

Val Gly Val Val Gly Gly Leu Leu Gly Ser Leu Val Leu Leu Val Trp
1               5                   10                  15

Val Leu Ala Val Ile
            20

<210> SEQ ID NO 128
<211> LENGTH: 97
<212> TYPE: PRT
<213> ORGANISM: Artificial Sequence
<220> FEATURE:
<223> OTHER INFORMATION: Intracellular tail

<400> SEQUENCE: 128

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu

<210> SEQ ID NO 129
<211> LENGTH: 150
<212> TYPE: PRT
<213> ORGANISM: Artificial Sequence
<220> FEATURE:
<223> OTHER INFORMATION: ECD of maPD-1

<400> SEQUENCE: 129

Pro Gly Trp Phe Leu Glu Ser Pro Asp Arg Pro Trp Asn Ala Pro Thr
1               5                   10                  15

Phe Ser Pro Ala Leu Leu Leu Val Thr Glu Gly Asp Asn Ala Thr Phe
            20                  25                  30

Thr Cys Ser Phe Ser Asn Ala Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Arg Leu
65                  70                  75                  80
```

```
Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Ala Leu Val
145             150

<210> SEQ ID NO 130
<211> LENGTH: 97
<212> TYPE: PRT
<213> ORGANISM: Artificial Sequence
<220> FEATURE:
<223> OTHER INFORMATION: Intracellular tail

<400> SEQUENCE: 130

Cys Ser Arg Ala Ala Gln Gly Thr Ile Glu Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Ala
        35                  40                  45

Pro Cys Val Pro Glu Gln Thr Glu Tyr Ala Thr Ile Val Phe Pro Ser
    50                  55                  60

Gly Leu Gly Thr Ser Ser Pro Ala Arg Arg Gly Ser Ala Asp Gly Pro
65                  70                  75                  80

Arg Ser Pro Arg Pro Leu Arg Pro Glu Asp Gly His Cys Ser Trp Pro
                85                  90                  95

Leu

<210> SEQ ID NO 131
<211> LENGTH: 22
<212> TYPE: PRT
<213> ORGANISM: Artificial Sequence
<220> FEATURE:
<223> OTHER INFORMATION: signal peptide

<400> SEQUENCE: 131

Met Trp Glu Ala Gln Phe Leu Gly Leu Leu Phe Leu Gln Pro Leu Trp
1               5                   10                  15

Val Ala Pro Val Lys Pro
            20

<210> SEQ ID NO 132
<211> LENGTH: 428
<212> TYPE: PRT
<213> ORGANISM: Artificial Sequence
<220> FEATURE:
<223> OTHER INFORMATION: Extra cellular domain

<400> SEQUENCE: 132

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
```

```
            35                  40                  45
Pro Pro Ala Ala Pro Gly His Pro Leu Ala Pro Gly Pro His Pro
 50                  55                  60
Ala Ala Pro Ser Ser Trp Gly Pro Arg Pro Arg Tyr Thr Val Leu
 65                  70                  75                  80
Ser Val Gly Pro Gly Leu Arg Ser Gly Arg Leu Pro Leu Gln Pro
                 85                  90                  95
Arg Val Gln Leu Asp Glu Arg Gly Arg Gln Gly Asp Phe Ser Leu
                100                 105                 110
Trp Leu Arg Pro Ala Arg Arg Ala Asp Ala Gly Glu Tyr Arg Ala Ala
            115                 120                 125
Val His Leu Arg Asp Arg Ala Leu Ser Cys Arg Leu Arg Leu Arg Leu
            130                 135                 140
Gly Gln Ala Ser Met Thr Ala Ser Pro Pro Gly Ser Leu Arg Ala Ser
145                 150                 155                 160
Asp Trp Val Ile Leu Asn Cys Ser Phe Ser Arg Pro Asp Arg Pro Ala
                165                 170                 175
Ser Val His Trp Phe Arg Asn Arg Gly Gln Gly Arg Val Pro Val Arg
                180                 185                 190
Glu Ser Pro His His Leu Ala Glu Ser Phe Leu Phe Leu Pro Gln
                195                 200                 205
Val Ser Pro Met Asp Ser Gly Pro Trp Gly Cys Ile Leu Thr Tyr Arg
            210                 215                 220
Asp Gly Phe Asn Val Ser Ile Met Tyr Asn Leu Thr Val Leu Gly Leu
225                 230                 235                 240
Glu Pro Pro Thr Pro Leu Thr Val Tyr Ala Gly Ala Gly Ser Arg Val
                245                 250                 255
Gly Leu Pro Cys Arg Leu Pro Ala Gly Val Gly Thr Arg Ser Phe Leu
                260                 265                 270
Thr Ala Lys Trp Thr Pro Pro Gly Gly Gly Pro Asp Leu Leu Val Thr
            275                 280                 285
Gly Asp Asn Gly Asp Phe Thr Leu Arg Leu Glu Asp Val Ser Gln Ala
            290                 295                 300
Gln Ala Gly Thr Tyr Thr Cys His Ile His Leu Gln Glu Gln Gln Leu
305                 310                 315                 320
Asn Ala Thr Val Thr Leu Ala Ile Ile Thr Val Thr Pro Lys Ser Phe
                325                 330                 335
Gly Ser Pro Gly Ser Leu Gly Lys Leu Leu Cys Glu Val Thr Pro Val
                340                 345                 350
Ser Gly Gln Glu Arg Phe Val Trp Ser Ser Leu Asp Thr Pro Ser Gln
                355                 360                 365
Arg Ser Phe Ser Gly Pro Trp Leu Glu Ala Gln Glu Ala Gln Leu Leu
            370                 375                 380
Ser Gln Pro Trp Gln Cys Gln Leu Tyr Gln Gly Glu Arg Leu Leu Gly
385                 390                 395                 400
Ala Ala Val Tyr Phe Thr Glu Leu Ser Ser Pro Gly Ala Gln Arg Ser
                405                 410                 415
Gly Arg Ala Pro Gly Ala Leu Pro Ala Gly His Leu
            420                 425

<210> SEQ ID NO 133
<211> LENGTH: 21
<212> TYPE: PRT
<213> ORGANISM: Artificial Sequence
```

```
<220> FEATURE:
<223> OTHER INFORMATION: Predicted TM region

<400> SEQUENCE: 133

Leu Leu Phe Leu Ile Leu Gly Val Leu Ser Leu Leu Leu Val Thr
1               5                   10                  15

Gly Ala Phe Gly Phe
            20

<210> SEQ ID NO 134
<211> LENGTH: 54
<212> TYPE: PRT
<213> ORGANISM: Artificial Sequence
<220> FEATURE:
<223> OTHER INFORMATION: Intracellular tail

<400> SEQUENCE: 134

His Leu Trp Arg Arg Gln Trp Arg Pro Arg Arg Phe Ser Ala Leu Glu
1               5                   10                  15

Gln Gly Ile His Pro Pro Gln Ala Gln Ser Lys Ile Glu Glu Leu Glu
            20                  25                  30

Gln Glu Pro Glu Pro Glu Pro Glu Pro Glu Pro Glu Pro Glu Pro Glu
        35                  40                  45

Pro Glu Pro Glu Gln Leu
    50

<210> SEQ ID NO 135
<211> LENGTH: 23
<212> TYPE: PRT
<213> ORGANISM: Artificial Sequence
<220> FEATURE:
<223> OTHER INFORMATION: signal peptide

<400> SEQUENCE: 135

Met Arg Gln Asp Leu Phe Leu Asp Leu Leu Leu Gln Leu Leu Trp
1               5                   10                  15

Glu Ala Pro Val Val Ser Ser
            20

<210> SEQ ID NO 136
<211> LENGTH: 419
<212> TYPE: PRT
<213> ORGANISM: Artificial Sequence
<220> FEATURE:
<223> OTHER INFORMATION: ECD

<400> SEQUENCE: 136

Gly Pro Gly Lys Glu Leu Ser Val Val Trp Ala Gln Glu Gly Ala Pro
1               5                   10                  15

Val His Leu Pro Cys Ser Leu Glu Phe Pro His Leu Asp Pro Asn Phe
            20                  25                  30

Leu Arg Arg Gly Trp Val Thr Trp Gln His Arg Pro Asp Ser Asp Gln
        35                  40                  45

Pro Ala Ser Ile Pro Ala Leu Asp Leu Gln Gly Met Pro Ser Thr
    50                  55                  60

Arg Arg His Pro Pro His Arg Tyr Thr Val Leu Ser Val Ala Pro Gly
65                  70                  75                  80

Gly Leu Arg Ser Gly Arg Gln Pro Leu Leu Ser His Val Gln Leu Glu
                85                  90                  95

Lys Arg Gly Pro Gln Arg Gly Asp Phe Ser Leu Trp Leu Arg Pro Ala
            100                 105                 110
```

Thr Arg Lys Asp Ala Gly Glu Tyr His Ala Phe Val Arg Leu Pro Asp
            115                 120                 125

Arg Asp Phe Ser Cys Ser Leu Arg Leu Arg Val Gly Gln Ala Ser Met
130                 135                 140

Ile Ala Ser Pro Pro Gly Thr Leu Lys Pro Ser Asp Trp Val Ile Leu
145                 150                 155                 160

Asn Cys Ser Phe Ser Arg Pro Asp Arg Pro Val Ser Val His Trp Phe
                165                 170                 175

Gln Gly Gln Ser Arg Val Pro Val His Asn Ser Pro Arg His Tyr Leu
                180                 185                 190

Ala Glu Ser Phe Leu Leu Pro Gln Val Ser Pro Leu Asp Ser Gly
                195                 200                 205

Thr Trp Gly Cys Val Leu Thr Tyr Arg Asp Gly Phe Asn Val Ser Ile
            210                 215                 220

Thr Tyr Asn Leu Lys Val Gln Gly Leu Glu Pro Val Ala Pro Leu Thr
225                 230                 235                 240

Val Tyr Ala Ala Glu Gly Ser Arg Val Glu Leu Pro Cys His Leu Pro
                245                 250                 255

Pro Val Val Gly Thr Pro Ser Leu Leu Ile Ala Lys Trp Thr Pro Pro
            260                 265                 270

Gly Gly Gly Pro Glu Leu Pro Val Thr Gly Lys Ser Gly Asn Phe Thr
            275                 280                 285

Leu Gln Leu Glu Asn Val Gly Arg Ala Gln Ala Gly Thr Tyr Thr Cys
            290                 295                 300

Ser Ile His Leu Gln Gly Arg Gln Leu Ser Ala Ala Val Thr Leu Ala
305                 310                 315                 320

Val Ile Thr Val Thr Pro Lys Ser Phe Gly Leu Pro Gly Ser Pro Gln
                325                 330                 335

Lys Leu Leu Cys Glu Val Val Pro Ala Ser Gly Glu Gly Arg Phe Val
                340                 345                 350

Trp Arg Pro Leu Ser Asp Leu Ser Arg Ser Ser Leu Gly Pro Val Leu
            355                 360                 365

Glu Leu Gln Glu Ala Lys Leu Leu Ala Glu Gln Trp Gln Cys Gln Leu
            370                 375                 380

Tyr Glu Gly Gln Lys Leu Leu Gly Ala Thr Val Tyr Thr Ala Glu Ser
385                 390                 395                 400

Ser Ser Gly Ala Trp Ser Ala Lys Arg Ile Ser Gly Asp Leu Lys Gly
                405                 410                 415

Gly His Leu

<210> SEQ ID NO 137
<211> LENGTH: 21
<212> TYPE: PRT
<213> ORGANISM: Artificial Sequence
<220> FEATURE:
<223> OTHER INFORMATION: Predicted TM region

<400> SEQUENCE: 137

Phe Leu Ser Leu Ile Leu Gly Ala Leu Ala Leu Phe Leu Leu Val Thr
1               5                   10                  15

Gly Ala Phe Gly Phe
            20

<210> SEQ ID NO 138
<211> LENGTH: 62

```
<212> TYPE: PRT
<213> ORGANISM: Artificial Sequence
<220> FEATURE:
<223> OTHER INFORMATION: Intracellular tail

<400> SEQUENCE: 138

His Leu Trp Arg Arg Gln Leu Leu Arg Arg Phe Ser Ala Leu Glu
1               5                   10                  15

His Gly Ile Arg Pro Pro Val Gln Ser Lys Ile Glu Glu Leu Glu
            20                  25                  30

Arg Glu Pro Glu Thr Glu Met Glu Pro Glu Thr Glu Pro Asp Pro Glu
        35                  40                  45

Pro Gln Pro Glu Pro Glu Leu Glu Pro Glu Ser Arg Gln Leu
    50                  55                  60

<210> SEQ ID NO 139
<211> LENGTH: 428
<212> TYPE: PRT
<213> ORGANISM: Artificial Sequence
<220> FEATURE:
<223> OTHER INFORMATION: ECD

<400> SEQUENCE: 139

Pro Gln Pro Gly Ala Glu Ile Ser Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Pro Ala Pro Gly His Pro Pro Ala Pro Gly His Arg Pro
    50                  55                  60

Ala Ala Pro Tyr Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Thr
        115                 120                 125

Val His Leu Arg Asp Arg Ala Leu Ser Cys Arg Leu Arg Leu Arg Val
    130                 135                 140

Gly Gln Ala Ser Met Thr Ala Ser Pro Pro Gly Ser Leu Arg Thr Ser
145                 150                 155                 160

Asp Trp Val Ile Leu Asn Cys Ser Phe Ser Arg Pro Asp Arg Pro Ala
                165                 170                 175

Ser Val His Trp Phe Arg Ser Arg Gly Gln Gly Arg Val Pro Val Gln
            180                 185                 190

Gly Ser Pro His His Leu Ala Glu Ser Phe Leu Phe Leu Pro His
    195                 200                 205

Val Gly Pro Met Asp Ser Gly Leu Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Ala Thr Pro Leu Thr Val Tyr Ala Gly Ala Gly Ser Arg Val
                245                 250                 255

Glu Leu Pro Cys Arg Leu Pro Pro Ala Val Gly Thr Gln Ser Phe Leu
            260                 265                 270
```

```
Thr Ala Lys Trp Ala Pro Pro Gly Gly Pro Asp Leu Leu Val Ala
        275                 280                 285

Gly Asp Asn Gly Asp Phe Thr Leu Arg Leu Glu Asp Val Ser Gln Ala
    290                 295                 300

Gln Ala Gly Thr Tyr Ile Cys His Ile Arg Leu Gln Gly Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Ala
            340                 345                 350

Ser Gly Gln Glu His Phe Val Trp Ser Pro Leu Asn Thr Pro Ser Gln
            355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu His Gln Gly Glu Thr Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Arg Ala Gly His Leu
            420                 425

<210> SEQ ID NO 140
<211> LENGTH: 21
<212> TYPE: PRT
<213> ORGANISM: Artificial Sequence
<220> FEATURE:
<223> OTHER INFORMATION: Predicted TM region

<400> SEQUENCE: 140

Pro Leu Phe Leu Ile Leu Gly Val Leu Phe Leu Leu Leu Val Thr
1               5                   10                  15

Gly Ala Phe Gly Phe
            20

<210> SEQ ID NO 141
<211> LENGTH: 62
<212> TYPE: PRT
<213> ORGANISM: Artificial Sequence
<220> FEATURE:
<223> OTHER INFORMATION: Intracellular tail

<400> SEQUENCE: 141

His Leu Trp Arg Arg Gln Trp Arg Pro Arg Arg Phe Ser Ala Leu Glu
1               5                   10                  15

Gln Gly Ile His Pro Pro Gln Ala Gln Ser Lys Ile Glu Glu Leu Glu
            20                  25                  30

Gln Glu Pro Glu Leu Glu Pro Glu Pro Glu Leu Glu Arg Glu Leu Gly
        35                  40                  45

Pro Glu Pro Glu Pro Gly Pro Glu Pro Glu Gln Leu
    50                  55                  60

<210> SEQ ID NO 142
<211> LENGTH: 16
<212> TYPE: PRT
<213> ORGANISM: Artificial Sequence
<220> FEATURE:
<223> OTHER INFORMATION: CDR3H 7165

<400> SEQUENCE: 142
```

```
Gly Gly Thr Tyr Tyr Tyr Gly Ser Gly Ser Tyr Tyr Thr Leu Asp Tyr
1               5                   10                  15

<210> SEQ ID NO 143
<211> LENGTH: 10
<212> TYPE: PRT
<213> ORGANISM: Artificial Sequence
<220> FEATURE:
<223> OTHER INFORMATION: CDR3H 7116

<400> SEQUENCE: 143

Asp Gly Asp Asn Trp Asp Val Phe Asp Ile
1               5                   10

<210> SEQ ID NO 144
<211> LENGTH: 9
<212> TYPE: PRT
<213> ORGANISM: Artificial Sequence
<220> FEATURE:
<223> OTHER INFORMATION: CDR3H 7100

<400> SEQUENCE: 144

Glu Arg Gly Trp Asp Val Phe Asp Ile
1               5

<210> SEQ ID NO 145
<211> LENGTH: 16
<212> TYPE: PRT
<213> ORGANISM: Artificial Sequence
<220> FEATURE:
<223> OTHER INFORMATION: CDR3H 7137

<400> SEQUENCE: 145

Gly Gly Thr Tyr Tyr Tyr Gly Ser Gly Ser Tyr Tyr Thr Leu Asp Phe
1               5                   10                  15

<210> SEQ ID NO 146
<211> LENGTH: 10
<212> TYPE: PRT
<213> ORGANISM: Artificial Sequence
<220> FEATURE:
<223> OTHER INFORMATION: CDR3H 7518

<400> SEQUENCE: 146

Asp Gly Ser Gly Trp Asp Asp Phe Asp Tyr
1               5                   10

<210> SEQ ID NO 147
<211> LENGTH: 10
<212> TYPE: PRT
<213> ORGANISM: Artificial Sequence
<220> FEATURE:
<223> OTHER INFORMATION: CDR3H 7134

<400> SEQUENCE: 147

Glu Pro Asn Trp Gly Val Tyr Phe Asp Tyr
1               5                   10

<210> SEQ ID NO 148
<211> LENGTH: 12
<212> TYPE: PRT
<213> ORGANISM: Artificial Sequence
<220> FEATURE:
<223> OTHER INFORMATION: CDR3H 7146

<400> SEQUENCE: 148

Asp Arg Glu Val Gly Ala Ile Tyr Tyr Phe Asp Tyr
```

```
1               5                  10

<210> SEQ ID NO 149
<211> LENGTH: 12
<212> TYPE: PRT
<213> ORGANISM: Artificial Sequence
<220> FEATURE:
<223> OTHER INFORMATION: CDR3H 7142

<400> SEQUENCE: 149

Glu Arg Asp Ile Gly Ser Leu Tyr Tyr Phe Asp Ser
1               5                  10

<210> SEQ ID NO 150
<211> LENGTH: 12
<212> TYPE: PRT
<213> ORGANISM: Artificial Sequence
<220> FEATURE:
<223> OTHER INFORMATION: CDR3H 7185

<400> SEQUENCE: 150

Asp Arg Glu Met Phe Thr Leu Tyr Phe Phe Asp Gln
1               5                  10

<210> SEQ ID NO 151
<211> LENGTH: 16
<212> TYPE: PRT
<213> ORGANISM: Artificial Sequence
<220> FEATURE:
<223> OTHER INFORMATION: CDR3H 7136

<400> SEQUENCE: 151

Asp Ser Thr Tyr Tyr Tyr Thr Ser Gly Ser Tyr Ser Val Phe Asp Tyr
1               5                  10                  15

<210> SEQ ID NO 152
<211> LENGTH: 15
<212> TYPE: PRT
<213> ORGANISM: Artificial Sequence
<220> FEATURE:
<223> OTHER INFORMATION: CDR3H 7443

<400> SEQUENCE: 152

Asp Thr Ser Thr Trp Gln Arg Gly Gly Tyr Lys Ala Phe Asp Tyr
1               5                  10                  15

<210> SEQ ID NO 153
<211> LENGTH: 16
<212> TYPE: PRT
<213> ORGANISM: Artificial Sequence
<220> FEATURE:
<223> OTHER INFORMATION: CDR3H 7167

<400> SEQUENCE: 153

Asp Arg Gly Tyr Asp Tyr Ser Gly Ser Tyr His Asn Trp Phe Asp Pro
1               5                  10                  15

<210> SEQ ID NO 154
<211> LENGTH: 11
<212> TYPE: PRT
<213> ORGANISM: Artificial Sequence
<220> FEATURE:
<223> OTHER INFORMATION: CDR3H 7515

<400> SEQUENCE: 154

Arg Pro Gly Pro Ala Leu Gly Asp Leu Asp Ser
1               5                  10
```

```
<210> SEQ ID NO 155
<211> LENGTH: 15
<212> TYPE: PRT
<213> ORGANISM: Artificial Sequence
<220> FEATURE:
<223> OTHER INFORMATION: CDR3H 7444

<400> SEQUENCE: 155

Asp Thr Gly Gln Ser Trp Ser Asn Tyr Tyr His Ala Phe Asp Tyr
1               5                   10                  15
```